United States Patent
Choi et al.

(10) Patent No.: US 11,566,055 B2
(45) Date of Patent: Jan. 31, 2023

(54) COMPOSITION FOR PREVENTING OR TREATING AUTOIMMUNE DISEASE BASED ON LRR DOMAIN OF NLRX1 PROTEIN

(71) Applicant: IUCF-HYU (INDUSTRY-UNIVERSITY COOPERATION FOUNDATION HANYANG UNIVERSITY), Seoul (KR)

(72) Inventors: Je-Min Choi, Seoul (KR); Ja-Hyun Koo, Cheonan-si (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 0 days.

(21) Appl. No.: 17/205,538

(22) Filed: Mar. 18, 2021

(65) Prior Publication Data
US 2022/0009978 A1 Jan. 13, 2022

(30) Foreign Application Priority Data
Jul. 9, 2020 (KR) .................. 10-2020-0084628

(51) Int. Cl.
C07K 14/47 (2006.01)
A61P 37/06 (2006.01)
C07K 14/00 (2006.01)
A61K 38/00 (2006.01)

(52) U.S. Cl.
CPC .......... *C07K 14/4702* (2013.01); *A61P 37/06* (2018.01); *C07K 14/001* (2013.01); *A61K 38/00* (2013.01)

(58) Field of Classification Search
CPC ... C07K 14/4702; C07K 14/001; A61P 37/06; A61K 38/00
See application file for complete search history.

(56) References Cited

U.S. PATENT DOCUMENTS

2004/0253615 A1* 12/2004 Inohara .................. C07K 14/47
435/325
2016/0263183 A1* 9/2016 Elias .................. G01N 33/6872
2018/0086788 A1* 3/2018 Kim ........................ A23L 33/40

FOREIGN PATENT DOCUMENTS

WO WO 2017/034244 * 2/2017 .......... C07K 14/435

OTHER PUBLICATIONS

The MGC Project Team, 2004, The Status, Quality, and Expansion of the NIH Full-Length cDNA Project: The Mammalian Gene Collection (MGC), Genome Res, 14: 2121-2127.*
Lim et al., 2015, dNP2 is a blood-brain barrier-permeable peptide enabling ctCTLA-4 protein delivery to ameliorate experimental autoimmune encephalomyelitis, Nature Communications, 6: 8244 (13 pages).*
Nagai-Singer et al, 2019, NLRX1 is a Multifaceted and Enigmatic Regulator of Immune System Function, Frontiers in Immunology, 10: 2419 (8 pages).*
Xia et al., 2011, NLRX1 Negatively Regulates TLR-Induced NF-kappaB Signaling by Targeting TRAF6 and IKK, Immunity, 34: 843-853.*
Oksenberg et al., "Limited heterogeneity of rearranged T-cell receptor Valpha transcripts in brains of multiple sclerosis patients", NATURE, vol. 345, May 24, 1990, pp. 344-346.
Oksenberg et al., "Selection for T-cell receptor Vbeta-Dbeta-Jbeta gene rearrangements with specificity for a myelin basic protein peptide in brain lesions of multiple sclerosis", NATURE, vol. 362, Mar. 4, 1993, pp. 68-70.

* cited by examiner

*Primary Examiner* — Amber D Steele
(74) *Attorney, Agent, or Firm* — Sughrue Mion, PLLC

(57) ABSTRACT

The present disclosure relates to a fusion protein including a cell-penetrating peptide and an LRR domain derived from the NLRX1 protein. Since the fusion protein can effectively inhibit and alleviate the disease severity of autoimmune diseases and directly regulates T cell functions, it can be usefully used to treat or prevent autoimmune diseases.

7 Claims, 37 Drawing Sheets

Specification includes a Sequence Listing.

1 : dNP2-LRR (39 kDa)
2 : dNP2-NBD (61 kDa)
3 : dNP2-EGFP (31 kDa)
4 : LRR (35 kDa)

| Group | Disease Incidence | Day of Onset |
|---|---|---|
| dNP2-EGFP | 11/11 (100%) | 9.18 ± 1.75 |
| dNP2-NBD | 11/11 (100%) | 10 ± 1.48 |
| dNP2-LRR | 8/11 (73%) | 11.5 ± 1.58* |

FIG. 28
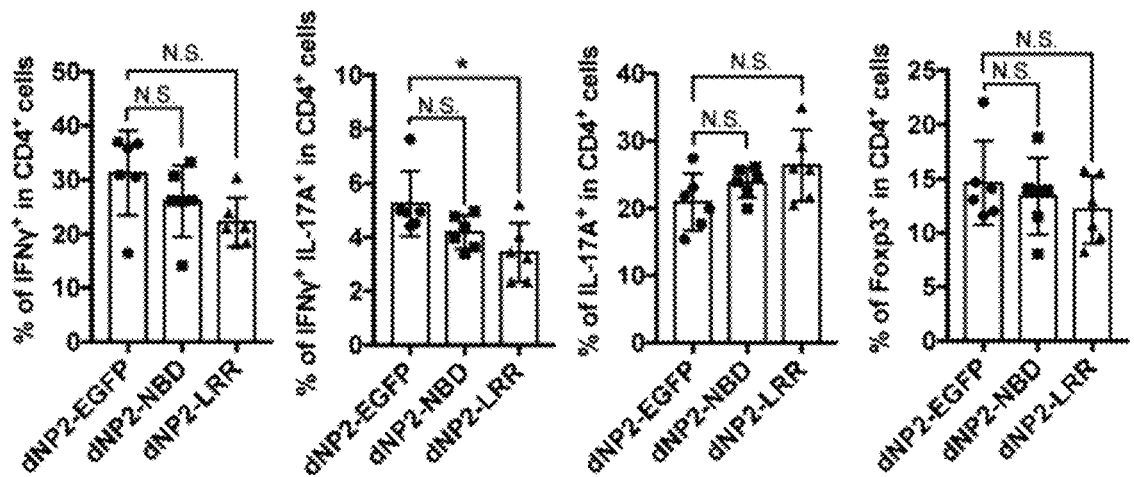
FIG. 29
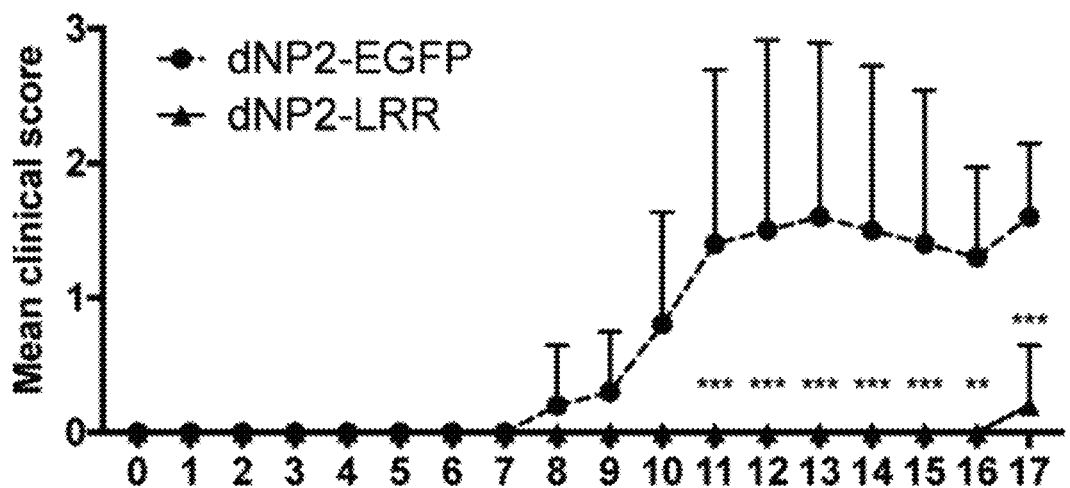
FIG. 30
| Group | Disease Incidence | Day of Onset |
|---|---|---|
| dNP2-EGFP | 5/5 (100%) | 11.2 ± 2.93 |
| dNP2-LRR | 1/5 (20%) | 17 ± 0 |

COMPOSITION FOR PREVENTING OR TREATING AUTOIMMUNE DISEASE BASED ON LRR DOMAIN OF NLRX1 PROTEIN

CROSS-REFERENCE TO RELATED APPLICATIONS

This application claims priority under 35 U.S.C. § 119 to Korean Patent Application No. 10-2020-0084628 filed on Jul. 9, 2020 in the Korean Intellectual Property Office, the disclosure of which is incorporated herein by reference in its entirety.

TECHNICAL FIELD

The present disclosure relates to a composition for preventing or treating a autoimmune disease based on a LRR domain of the NLRX1 protein. More specifically, a fusion protein formed from the fusion of the LRR domain of the NLRX1 protein and a cell-penetrating peptide can prevent or treat an autoimmune disease by inhibiting T cell functions.

BACKGROUND

Multiple sclerosis (MS) is the most representative neurological autoimmune disease. Multiple sclerosis is an autoimmune disease caused by inflammation in the central nervous system due to recognition of proteins expressed on neurons as antigens. Of the various immune cells involved in disease progression including macrophages, microglia and B cells, Th1 and Th17 cells in particular are known to be the key cells involved in MS pathogenesis. Currently, MS treatment focuses on relieving various symptoms and neurological disorders since no curative medicine has been developed yet.

For example, systemic treatment for treating neurological autoimmune disease with anti-inflammatory drugs has been known to have limited efficacy for central nervous system (CNS) inflammations due to the difficulty of these drugs in penetrating the blood-brain barrier (BBB).

Although various BBB-penetrating methods such as viral vectors, non-viral nanoparticles, exosomes and enhancers have been developed to overcome this limitation, these methods show high recurrence rate and are limited in preventing relapse.

Experimental autoimmune encephalomyelitis (EAE) is another type of autoimmune disease. It is induced by autoimmunizing animals against myelin basic protein (MBP, a constituent of the white matter of the brain and the spinal cord) and causes the same clinical symptoms observed in neurological autoimmune diseases: demyelination and paralysis. The EAE animal model is an animal model suitable for the study of neurological autoimmune diseases including multiple sclerosis because the cause of clinical symptoms is the same as multiple sclerosis in human. Steinman et al. showed that the predominant cell type found in the brain lesions of multiple sclerosis patients is CD4+ T cells (Oksenberg et al., 1990, *Nature* 345: 344-345) and that the T-cell receptor (the molecule responsible for antigen recognition) associated with the cells in these brain lesions has the same three amino acid binding motifs for antigen recognition as on the CD4+ T cells responsible for causing EAE (Oksenberg et al., 1993, *Nature* 362: 68-70).

Because neurological autoimmune diseases are caused by uncontrolled activation of myelin antigen-specific T cells, the main target for controlling inflammation should be focused on effective delivery of a drug into the CNS and the drug should be able to be delivered to T cells in the CNS to suppress immunity.

Because drug delivery to the CNS in vivo is very limited, there has been limitation in treating neurological autoimmune diseases with existing drugs.

NLRX1 (nucleotide-binding, leucine-rich repeat containing X1) is a mitochondrial protein identified as a negative regulator of antiviral responses by regulating MAVS (mitochondrial antiviral-signaling protein)-IRF (interferon regulatory factor) and STING (stimulator of interferon genes)-IRF signaling. It is also known to play an important role in the regulation of autophagy by interacting with TuFM (Tu translation elongation factor). However, nothing is known about its protective mechanism against autoimmune diseases.

At present, the necessity for development of protein-based therapeutic agents for autoimmune diseases with few risks is increasing. The existing therapeutic agents for autoimmune diseases merely alleviate symptoms and do not provide complete prevention or treatment. Accordingly, the development of a novel therapeutic agent for autoimmune diseases, which can be delivered effectively into cells, has little cytotoxicity, has direct therapeutic effect beyond merely alleviating the symptoms of autoimmune diseases, and can be stably used for clinical treatment and cell therapy, is keenly needed.

SUMMARY

The present disclosure is directed to providing a fusion protein including, at one end of (a) a cell-penetrating peptide represented by SEQ ID NO 1, (b) a peptide composed of a LRR domain derived from the NLRX1 protein represented by SEQ ID NO 2.

The present disclosure is also directed to providing a gene encoding the fusion protein, a recombinant vector including the same, and a transformant transformed thereby.

The present disclosure is also directed to providing a pharmaceutical composition for preventing or treating an autoimmune disease, which contains the fusion protein or a recombinant protein isolated from the transformant as an active ingredient.

In an aspect, the present disclosure provides a fusion protein including, at one end of (a) a cell-penetrating peptide represented by SEQ ID NO 1, (b) a peptide composed of a LRR domain derived from the NLRX1 protein represented by SEQ ID NO 2.

The LRR domain may be composed of an amino acid sequence represented by SEQ ID NO 3.

The fusion protein may be composed of an amino acid sequence represented by SEQ ID NO 4.

In another aspect, the present disclosure provides a gene encoding the fusion protein.

In another aspect, the present disclosure provides a recombinant vector including the gene.

In another aspect, the present disclosure provides a transformant transformed with the recombinant vector.

In another aspect, the present disclosure provides a pharmaceutical composition containing the fusion protein or a recombinant protein isolated from the transformant as an active ingredient.

The pharmaceutical composition may be a pharmaceutical composition for preventing or treating an autoimmune disease.

The autoimmune disease may be any one selected from a group consisting of rheumatoid arthritis, psoriatic arthritis, osteoarthritis, Still's disease, juvenile arthritis, lupus, diabetes mellitus, Hashimoto's thyroiditis, Graves' disease, Sjogren's syndrome, Addison's disease, ocular hepatocellular seizure-epileptic syndrome, ankylosing spondylitis, antiphospholipid antibody syndrome, aplastic anemia, autoimmune hepatitis, chronic digestive dysfunction, Goodpasture syndrome, idiopathic thrombocytopenic purpura, optic neuritis, scleroderma, primary dysplasia cirrhosis, Takayasu arteritis, temporal arteritis, autoimmune hemolytic anemia, Wegener's granulomatosis, psoriasis, systemic alopecia, Behcet's disease, chronic fatigue, autonomic nystagmus, endometriosis, interstitial cystitis, neuromuscular dystrophy, scleroderma, vulvar pain, multiple sclerosis, neuromyelitis optica, myasthenia gravis, Guillain-Barre syndrome, autoimmune uveitis, acute disseminated encephalomyelitis, autoimmune encephalomyelitis, acute transverse myelitis, autoimmune encephalopathy and chronic inflammatory demyelinating polyneuropathy.

The pharmaceutical composition may be a pharmaceutical composition for preventing or treating a neurological autoimmune disease.

The neurological autoimmune disease may be any one selected from a group consisting of multiple sclerosis, neuromyelitis optica, myasthenia gravis, Guillain-Barre syndrome, autoimmune uveitis, acute disseminated encephalomyelitis, autoimmune encephalomyelitis, acute transverse myelitis, autoimmune encephalopathy and chronic inflammatory demyelinating polyneuropathy.

In another aspect, the present disclosure provides a method for treating an autoimmune disease, more specially a neurological autoimmune disease, which includes administering the pharmaceutical composition to a patient with an autoimmune disease.

The present disclosure relates to a fusion protein including a cell-penetrating peptide and a LRR domain derived from the NLRX1 protein. Since the fusion protein is capable of effectively preventing and alleviating autoimmune diseases and regulates T cell functions directly, it may be usefully used to treat or prevent autoimmune diseases.

BRIEF DESCRIPTION OF DRAWINGS

FIG. 1 shows the structure of DNA constructs of dNP2-LRR, dNP2-NBD, dNP2-EGFP and LRR.

FIG. 28 shows a result of treating a prevention scheme model with a dNP2-LRR fusion protein of Example 1, a dNP2-NBD fusion protein of Comparative Example 1 or a dNP2-EGFP fusion protein of Comparative Example 2 and analyzing the frequency of IFN$\gamma^+$, IFN$\gamma^+$IL-17A$^+$, IL-17A$^+$ and Foxp3$^+$ CD4 T cells in the spinal cord tissues obtained from each group by flow cytometry. n=11 and error bars indicate S.D. *P<0.05, P<0.01 and *P<0.001. N.S.: not significant.

FIG. 29 shows a result of treating a semi-therapeutic animal model with a dNP2-LRR fusion protein of Example 1 or a dNP2-EGFP fusion protein of Comparative Example 2 and analyzing clinical scores every day. n=5 and error bars indicate S.D. *P<0.05, P<0.01 and *P<0.001. N.S.: not significant.

FIG. 30 shows a result of treating a semi-therapeutic animal model with a dNP2-LRR fusion protein of Example 1 or a dNP2-EGFP fusion protein of Comparative Example 2 and analyzing disease incidence rate.

DETAILED DESCRIPTION OF EMBODIMENTS

Figure 1:
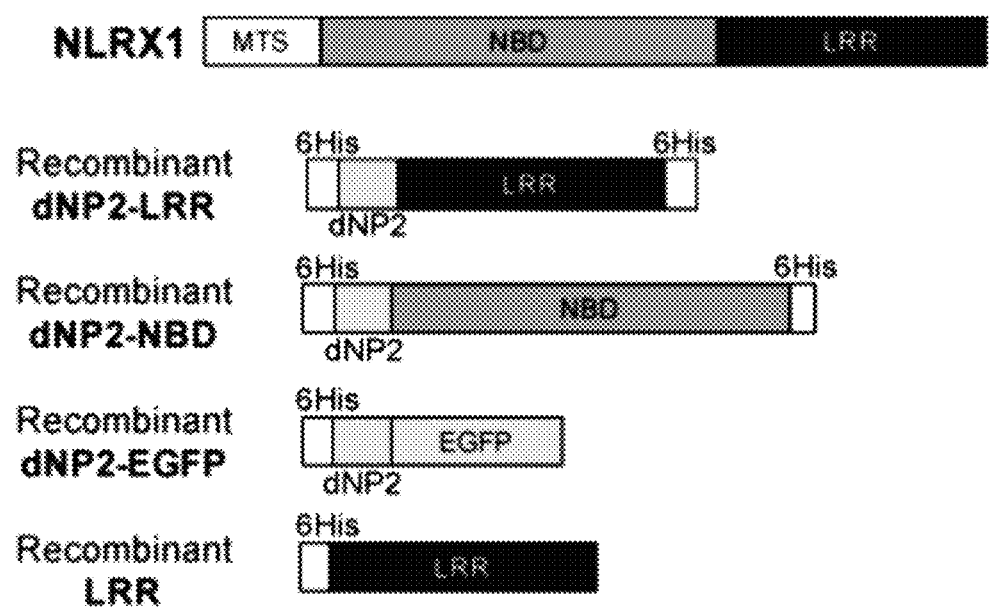
FIG. 1 schematically shows the structure of genes encoding various fusion proteins. Specifically.

The inventors of the present disclosure have made efforts to develop a substance capable of overcoming and replacing the existing agents for preventing or treating autoimmune diseases, more specially neurological autoimmune diseases. As a result, they have elucidated the function of a domain present in the NLRX1 protein, devised a therapeutic strategy utilizing a cell-penetrating peptide for effective delivery thereof into cells, identified that a fusion protein using the same obviously has a preventive or therapeutic effect, and completed the present disclosure.

An aspect of the present disclosure relates to a fusion protein including, at one end of (a) a cell-penetrating peptide represented by SEQ ID NO 1, (b) a peptide composed of a LRR domain derived from the NLRX1 protein represented by SEQ ID NO 2.

NLRX1 (NLR family member X1), nucleotide-binding oligomerization domain, leucine-rich repeat containing X1, is a protein that in humans is encoded by the NLRX1 gene. It is also known as NOD-like receptor X1, NLR family X1, etc. It is composed of an N-terminal effector domain containing a mitochondrion localization signal, a NACHT domain (NBD) and a C-terminal leucine-rich repeat (LRR) domain. The NLRX1 protein plays a very important role in the immune system. Specifically, it has been reported to affect the innate immunity to viruses by interfering with the mitochondrial antiviral signaling protein (MAVS)/retinoic acid-inducible gene I (RIG-I) mitochondrial antiviral pathway. In addition, NLRX1 is involved in host immunity during bacterial infections, such as *Chlamydia trachomatis* and *Helicobacter pylori*, by regulating bacterial burden and inflammation in mononuclear phagocytes. Mechanisms underlying the NLRX1 protein have not been elucidated well yet, however computational modeling predictions suggest that the expression of the NLRX1 protein may be controlled by negative feedback circuits induced early after infection.

The inventors of the present disclosure have elucidated the function of each domain of NLRX1 and have identified that the LRR domain of the NLRX1 protein has not only preventive effect but also therapeutic effect for neurological autoimmune diseases. Furthermore, they have prepared a fusion protein in which, at one end of the LRR domain derived from the NLRX1 protein, a dNP2 cell-penetrating peptide represented by SEQ ID NO 1 is fused.

Specifically, in an example of the present disclosure, the LRR domain sequence from the NLRX1 protein was identified, and a fusion protein in which the dNP2 peptide is linked to the LRR domain was prepared by designing a plasmid DNA in which the dNP2 peptide is bound to the LRR domain, introducing the same into an expression vector and then transducing the same into host bacteria.

The present disclosure relates to a fusion protein formed from the binding between the LRR domain derived from the NLRX1 protein, the function of which has not been known in detail previously, and a cell-penetrating peptide. In a test example to be described later, it was confirmed that the LRR domain derived from the NLRX1 protein represented by SEQ ID NO 2 of the present disclosure cannot exhibit the effect of preventing, treating or alleviating autoimmune diseases when it is bound to cell-penetrating peptides other than the dNP2 cell-penetrating peptide.

The information about the NLRX1 protein or its gene can be obtained from public databases such as GenBank of the National Center for Biotechnology Information (NCBI). Specifically, the NLRX1 protein may be the NLRX1 protein represented by SEQ ID NO 2. In addition, the LRR domain derived from the NLRX1 protein may be a fragment of the NLRX1 protein represented by SEQ ID NO 2 and may be composed of an amino acid sequence represented by SEQ ID NO 3. More specifically, it may be composed of the amino acid sequence represented by SEQ ID NO 3 or one having homology while retaining the activity of the sequence. In addition, the LRR domain derived from the NLRX1 protein may have a sequence identity to SEQ ID NO 3 of at least 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99%, although not being limited thereto.

The LRR domain may be composed of an amino acid sequence represented by SEQ ID NO 3.

When a cell-penetrating peptide other than the dNP2 cell-penetrating peptide having an amino acid sequence represented by SEQ ID NO 1 used in the present disclosure is used, the fusion protein cannot achieve the effect of preventing, treating or alleviating autoimmune diseases. Therefore, most specifically, the cell-penetrating peptide may be composed of an amino acid sequence represented by SEQ ID NO 1.

The fusion protein may be composed of amino acid sequence represented by SEQ ID NO 4.

It was identified that the fusion protein according to the present disclosure is effectively delivered into cells, particularly into activated T cells, directly inhibits the function of effector T cells and improves disease severity of EAE through reduced T cell infiltration and IFNγ production.

The fusion protein or a nucleic acid encoding the same may further include a nuclear localization signal (NLS) for localizing the fusion protein in the cell nucleus.

The fusion protein may be a connected to a tag favorable for isolation and/or purification. Examples include small peptide tags such as a His tag, a Flag tag, an S tag, etc., a GST (glutathione S-transferase) tag, an MBP (maltose-binding protein) tag, etc., although not being limited thereto.

Another aspect of the present disclosure relates to a gene encoding a fusion protein. Specifically, it relates to a gene encoding a fusion protein including (a) cell-penetrating peptide represented by SEQ ID NO 1 and a peptide composed of a LRR domain derived from the NLRX1 protein represented by SEQ ID NO 2.

The fusion protein is the same as described above. The gene may be one in which one or more codon sequence has been modified with a codon suitable for expression in a host cell. The host cell may be *E. coli*, yeast or a combination thereof. The gene may encode each of the cell-penetrating peptide represented by SEQ ID NO 1 and the LRR domain represented by SEQ ID NO 3, or may encode the entire fusion protein having an amino acid sequence represented by SEQ ID NO 4. For example, the gene may have a base sequence represented by SEQ ID NO 6.

In an example of the present disclosure, after preparing a gene encoding the fusion protein amplified through gene amplification and introducing the same into a pET-28a expression vector, followed by transforming into host cells, it was investigated through gene base sequencing whether it was properly inserted into the expression vector. As a result, it was confirmed to have the base sequence of SEQ ID NO 6.

In the present disclosure, the term "recombinant" refers to a cell which replicates a heterologous nucleic acid, expresses the nucleic acid, or expresses a protein encoded by a peptide, a heterologous peptide or a heterologous nucleic acid. A recombinant cell can express a gene or a gene fragment that is not found in the natural form in either the sense or antisense form. The recombinant cell can also express a gene not found in natural cells, wherein the gene is modified and reintroduced into the cell by artificial means.

In the present disclosure, the term "vector" refers to any carrier for cloning and/or transferring a nucleotide into a host cell. The vector may be a replicon which allows for the replication of fragments combined with other DNA fragments. The "replicon" refers to any genetic unit acting as a self-replicating unit for DNA replication in vivo, that is, replicable by self-regulation (e.g., a plasmid, a phage, a cosmid, a chromosome or a virus).

In the present disclosure, the term "vector" includes viral and non-viral carriers for introducing a nucleotide into a host cell in vitro, ex vivo or in vivo.

The recombinant vector of the present disclosure may include a gene encoding a fusion protein including, at one end of (a) a cell-penetrating peptide represented by SEQ ID NO 1, (b) a peptide composed of a LRR domain derived from the NLRX1 protein represented by SEQ ID NO 2. More specifically, it may include a gene encoding the amino acid sequence of SEQ ID NO 4. Alternatively, it may include a gene composed of the base sequence of SEQ ID NO 6.

If a peptide other than the cell-penetrating peptide represented by SEQ ID NO 1 is linked, intracellular delivery efficiency is hardly achieved and, if any, the effect of preventing or treating autoimmune diseases may decrease significantly, as can be seen from a test example to be described later.

Another aspect of the present disclosure relates to a transformant transformed with the recombinant vector.

In the present disclosure, the term "transformation" refers to change in the genetic characteristics of an organism caused by a foreign DNA. That is to say, it refers to the change in genetic characteristics occurring when a DNA isolated from an organism of a certain lineage is introduced into live cells of another lineage.

In the present disclosure, the term "transformant" refers to a transformed plant, a transformed animal, etc. produced through transformation, and includes a gene recombination product wherein modification or alternation of a specific gene has been induced using the gene recombination technology. The transformant of the present disclosure may be adequately selected by those skilled in the art from any known cells that can be used for transformation without limitation. It may be a non-human transformant, specifically a transformant derived from microorganisms.

Another aspect of the present disclosure relates to a pharmaceutical composition for preventing or treating an autoimmune disease, which contains the fusion protein or a recombinant protein isolated from the transformant as an active ingredient.

The pharmaceutical composition of the present disclosure may further contain a pharmaceutically acceptable carrier. The pharmaceutically acceptable carrier may be one commonly used for preparations, and includes lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, etc., although not being limited thereto. The pharmaceutical composition of the present disclosure may further include, in addition to the above-described ingredients, a lubricant, a wetting agent, a sweetener, a flavorant, an emulsifier, a suspending agent, a preservative, etc. Suitable pharmaceutically acceptable carriers and preparations are described in detail in Remington's Pharmaceutical Sciences (19th ed., 1995).

In the present disclosure, the term "prevention" refers to any action of preventing or delaying an autoimmune disease by administering a composition containing the fusion protein of the present disclosure or a protein or recombinant protein isolated from the transformant as an active ingredient.

In the present disclosure, the term "treatment" refers to any action of improving or favorably changing an autoimmune disease by administering a composition containing the fusion protein of the present disclosure or a protein or recombinant protein isolated from the transformant as an active ingredient.

The autoimmune disease may be any one selected from a group consisting of rheumatoid arthritis, psoriatic arthritis, osteoarthritis, Still's disease, juvenile arthritis, lupus, diabetes mellitus, Hashimoto's thyroiditis, Graves' disease, Sjogren's syndrome, Addison's disease, ocular hepatocellular seizure-epileptic syndrome, ankylosing spondylitis, antiphospholipid antibody syndrome, aplastic anemia, autoimmune hepatitis, chronic digestive dysfunction, Goodpasture syndrome, idiopathic thrombocytopenic purpura, optic neuritis, scleroderma, primary dysplasia cirrhosis, Takayasu arteritis, temporal arteritis, autoimmune hemolytic anemia, Wegener's granulomatosis, psoriasis, systemic alopecia, Behcet's disease, chronic fatigue, autonomic nystagmus, endometriosis, interstitial cystitis, neuromuscular dystrophy, scleroderma, vulvar pain, multiple sclerosis, neuromyelitis optica, myasthenia gravis, Guillain-Barre syndrome, autoimmune uveitis, acute disseminated encephalomyelitis, autoimmune encephalomyelitis, acute transverse myelitis, autoimmune encephalopathy and chronic inflammatory demyelinating polyneuropathy.

The autoimmune disease may be a neurological autoimmune disease, and the neurological autoimmune disease may be a central nervous system autoimmune disease, although not being particularly limited thereto. For example, it may be any one selected from a group consisting of multiple sclerosis, neuromyelitis optica, myasthenia gravis, Guillain-Barre syndrome, autoimmune uveitis, acute disseminated encephalomyelitis, autoimmune encephalomyelitis, acute transverse myelitis, autoimmune encephalopathy and chronic inflammatory demyelinating polyneuropathy. More specifically, the neurological autoimmune disease may be any one selected from a group consisting of multiple sclerosis, Guillain-Barre syndrome, acute disseminated encephalomyelitis, autoimmune encephalomyelitis, autoimmune encephalopathy and chronic inflammatory demyelinating polyneuropathy. Most specifically, it may be any one selected from a group consisting of multiple sclerosis, autoimmune encephalomyelitis and autoimmune encephalopathy.

Since the neurological autoimmune disease is a disease arising from an abnormal immune response to autologous cells, drugs that suppresses autoimmunity are mainly used for treatment. However, they are limited in that continued is difficult due to many side effects and recurrence cannot be prevented effectively. Although several immunotherapies are available, no sure therapeutic effect has been proven thus far. There are various animal models of human autoimmune diseases, which are used to test possible therapeutic strategies.

Inflammatory responses are one of the main cause of secondary damage occurring after spinal cord injury and play a central role in regulating the pathogenesis of acute and chronic spinal cord injury. After spinal cord injury, inflammatory responses occur due to increased expression or activity of inflammation-related genes and proteins. Particularly, pro-inflammatory cytokines such as TNF-$\alpha$, IL-1$\beta$, IL-6, etc. and inflammatory mediators such as cyclooxygenase 2 (COX-2), inducible nitric oxide synthase (iNOS), prostaglandin synthase 2, etc. are known to be involved. These substances are secreted by blood cells that have flown in after injury or microglia present in the spinal cord and exhibit cytotoxicity and also affect the progression of axonal degeneration or demyelination. In addition, particularly among the blood cells that have flown in after spinal cord injury, neutrophils, macrophages, etc. are known to be involved in apoptosis and glial scar formation by inducing inflammatory responses and cause continuous inflammatory response by inducing additional activation of nearby cells. Therefore, prevention of their inflow is estimated as one of important therapeutic strategies.

Neuromyelitis optica is an inflammatory demyelinating disease of the central nervous system mainly invading the spinal cord and the optic nerve, and has been previously considered a different form of multiple sclerosis. The main symptoms of neuromyelitis optica are unilateral or bilateral optic neuritis and myelitis caused by autoantibodies. Although the disease has been confused with multiple sclerosis due to similar clinical symptoms, a lot has been known about the onset mechanism and clinical characteristics of neuromyelitis optica as autoantibodies to aquaporin-4 (AQP-4), a water channel protein in the central nervous system, are found. Neuromyelitis optica has been diagnosed when bilateral optic neuritis and myelitis occur simultaneously or successively with a short interval. But, recently, a new diagnostic criterion has been established as the AQP-4 antibody and characteristic brain imaging features are known. It is known that neuromyelitis optica shows worse prognosis and exhibits lower effect of preventing recurrence than multiple sclerosis because it recurs more frequently in the early stage and is aggravated faster.

Chronic inflammatory demyelinating polyneuropathy is a nervous system disease characterized by progressive weakness and impaired sensory function in the legs and arms. This disease is caused by damage to the myelin of the peripheral nervous system. The swelling of the nerve root is another characteristic of this disease. Symptoms include numbness (beginning from toes and fingers), weakness of the arms and legs, muscular pain, loss of deep tendon reflexes, fatigue and abnormal sensations. Untreated chronic inflammatory demyelinating polyneuropathy is characterized by accumulating disability that requires physical and occupational therapy, orthotic devices and long-term treatment.

Multiple sclerosis is a disease of the central nervous system (the brain and the spinal cord) that damages the fatty layer that surrounds the nerves (the myelin sheath) causing it to become scarred with plaques of hardened tissue. If the thickness of the myelin sheath is decreased due to damage to the myelin, the efficiency of neurotransmission is decreased and normal neurotransmission is interrupted. To put it simply, the transmission of signals between nerve cells becomes slow just as the conduction of electricity becomes slow if the insulating material covering an electrical wire is damaged. Although the symptom is alleviated in the early stage as the myelin is repaired, the damage becomes permanent as attacks are repeated. The myelin damage leads to symptoms such as vision impairment, loss of balance, etc. and can cause paralysis in some patients.

Representative therapeutic agents for alleviating the disease include beta-interferon and glatiramer acetate. However, these medications are merely for alleviating symptoms and they cannot surely prevent recurrence.

Experimental autoimmune encephalomyelitis (EAE) is induced by autoimmunizing animals against myelin basic protein (MBP, a constituent of the white matter of the brain and the spinal cord) and causes the same clinical symptoms observed in neurological autoimmune diseases: demyelination and paralysis. The EAE animal model is an animal model suitable for the study of neurological autoimmune diseases including multiple sclerosis because the cause of clinical symptoms is the same as multiple sclerosis in human. Steinman et al. showed that the predominant cell type found in the brain lesions of multiple sclerosis patients is CD4+ T cells (Oksenberg et al., 1990, Nature 345: 344-345) and that the T-cell receptor (the molecule responsible for antigen recognition) associated with the cells in these brain lesions has the same three amino acid binding motifs for antigen recognition as on the CD4+ T cells responsible for causing EAE (Oksenberg et al., 1993, Nature 362: 68-70).

The inventors of the present disclosure have researched to develop an agent for preventing and treating autoimmune diseases. In doing so, they have identified that the fusion protein of the present disclosure improves neurological clinical symptoms of a disease, reduces demyelination of the spinal cord and infiltration of inflammatory cells, inhibits the expression of cytokines, suppresses the proliferation of splenocytes, and reduces T cell activation and Th1 cell differentiation in an EAE animal model without exhibiting cytotoxicity, and that, accordingly, the fusion protein of the present disclosure can be usefully used as an active ingredient of a pharmaceutical composition for preventing or treating an autoimmune disease.

In the present disclosure, the terms "fusion protein" and "transformant" are the same as described above.

The pharmaceutical composition of the present disclosure may be administered orally or parenterally. Specifically, it may be administered parenterally, e.g., intravenously, topically, intraperitoneally, etc.

The appropriate administration dosage of the pharmaceutical composition of the present disclosure varies depending on such factors as the preparation method, the mode of administration, the age, body weight, sex, pathological condition and diet of a patient, administration time, administration route, excretion rate and response sensitivity. An ordinarily trained physician may easily determine and describe an administration dosage effective for the desired treatment or prevention. According to a specific exemplary embodiment of the present disclosure, a daily administration dosage of the pharmaceutical composition of the present disclosure is 0.0001-100 mg/kg.

The pharmaceutical composition of the present disclosure may be prepared according to a method that can be easily carried out by those having ordinary knowledge in the art to which the present disclosure belongs in single-dose forms or in multi-dose packages using a pharmaceutically acceptable carrier and/or excipient. A formulation of the pharmaceutical composition may be a solution in an oily or aqueous medium, a suspension, an emulsion, an extract, a powder, a granule, a tablet or a capsule, and may further contain a dispersant or a stabilizer.

The present disclosure provides a method for preventing or treating an autoimmune disease, more specially a neurological autoimmune disease, which includes a step of administering the pharmaceutical composition.

In the method of the present disclosure, the animal may be any animal such as chicken, pig, monkey, dog, cat, rabbit, guinea pig, rat, mouse, cow, sheep, goat, etc. without limitation. Specifically, it may be a non-human animal.

In the present disclosure, the administration may be made by any means for administration known in the art. For example, the administration may be made intravenously, intramuscularly, intraperitoneally, orally, transdermally, intramucosally, intranasally, intratracheally or subcutaneously. The administration may be made systemically or topically.

In the method of the present disclosure, the composition of the present disclosure may be administered with a therapeutically or prophylactically effective amount. The "therapeutically or prophylactically effective amount" may be selected adequately by those skilled in the art in consideration of the severity of a symptom and the sex, age, body weight, etc. of a subject. For example, a therapeutically or prophylactically effective amount of the fusion protein, or the protein extract or recombinant protein isolated from the transformant may be 0.0001-100 mg based on 1 kg body weight of a subject.

Hereinafter, the present disclosure will be described in more detail through examples. The following examples are for illustrative purposes only and it will be apparent to those having ordinary knowledge in the art that the scope of the present disclosure is not limited by the examples.

Preparation Example

Preparation Example 1 Amplification of LRR Domain Derived from NLRX1 Protein by PCR A plasmid including a full-length gene encoding the NLRX1 protein (amino acid sequence of SEQ ID NO 2) and a plasmid including a gene with 2022 bp at the N-terminal deleted (903 bp; LRR) were prepared, respectively.

For amplification of a sequence encoding the full-length NLRX1, a forward primer (5'-CTA GTCGAC ATG AGG TGG GGC TGC CAT-3'; SEQ ID NO 9) and a reverse primer (5'-CCG GAATTC GTGTCCAGAACCT-3'; SEQ ID NO 10) were used. PCR was conducted by repeating a total of 30 cycles of denaturation (95° C., 30 seconds), annealing (60° C., 30 seconds) and extension (72° C., 30 seconds). For amplification of a sequence encoding dNP2-LRR (insert; SEQ ID NO 6), PCR was conducted once using a first forward primer (5'-CGGCTAGC AAAATTAAAAAAGT-CAAGAAGAAAGGAAGAAAAGTCGACCTTCTTGAC-CATCTC-3'; SEQ ID NO 11) and a reverse primer (5'-CCGGAATTC GTGTCCAGAACCT-3'; SEQ ID NO 12) and then PCR was conducted again using the product using a second forward primer (5'-CTAGTCGAC AAGAT-CAAGAAGGT-TAAAAAAAAGGGTCGCAAGGGCTCTAAAAT-TAAAAAAGTC AAG-3'; SEQ ID NO 13) and a reverse primer (5'-CCGGAATTC GTGTCCAGAACCT-3'; SEQ ID NO 12). For LRR, PCR was repeated for 30 cycles of denaturation (95° C., 30 seconds), annealing (65° C., 30 seconds) and extension (72° C., 1 minute) and the PCR product was used as an insert.

EXAMPLES

Example 1 Isolation and Purification of dNP2-LRR Fusion Protein

1) Preparation of pET28a Vector

An insert DNA was prepared from a plasmid DNA (SEQ ID NO 5) for expressing a dNP2-LRR fusion protein (SEQ ID NO 4). Specifically, after preparing a plasmid DNA encoding dNP2-LRR represented by SEQ ID NO 5 using an insert DNA of a dNP2-LRR fusion protein represented by SEQ ID NO 6 and pET28a DNA (vector), the protein represented by SEQ ID NO 4 was purified using the same. For cloning, the protein pET28a expression vector was excised with NheI and EcoRI restriction enzymes and then the insert DNA of the dNP2-LRR fusion protein represented by SEQ ID NO 6 was inserted into the pET28a expression vector by a ligase. After transforming each prepared plasmid DNA into DH5alpha, the obtained colony was inoculated to an LB medium and then incubated for 12 hours in a shaking incubator under the condition of 37° C. and 200 rpm. After the incubation was completed, E. coli was recovered. After isolating the DNA (SEQ ID NO 5) encoding the dNP2-LRR fusion protein therefrom, the preparation of the vector was confirmed by DNA sequencing (Cosmo Genetech).

2) Expression and Purification of dNP2-LRR Fusion Protein in BL-21 Rosetta

1) In order to express the dNP2-LRR fusion protein from the transformed BL-21 Rosetta, each colony was inoculated to 50 mL of an LB liquid medium containing chloramphenicol (34 µg/mL) and ampicillin (50 µg/mL) antibiotics, cultured at 37° C. for 10 hours and then transferred to 500 mL of a fresh LB liquid medium. The culturing was performed until the O.D. value measured at 600 nm with a spectrophotometer reached 0.4-0.6. After adding IPTG to a concentration of 0.2 mM, temperature was lowered to 20° C. and culturing was performed further at 150 rpm for 14 hours. After the culturing was completed, the culture was recovered and centrifuged. After discarding the supernatant, the remaining pellet was resuspended by adding a lysis buffer (8 M urea, 100 mM NaH$_2$PO$_4$, 10 mM Tris, pH 8.0). The resuspended solution was treated with an ultrasonic cell disruptor (VCX-130; Sonics & Materials) for 2 minutes. After centrifugation, the separated supernatant was filtered through a 0.45-µm filter and then incubated with Ni-NTA agarose beads (Qiagen, Hilden, Germany) for 30 minutes. The beads were washed with a denaturing washing buffer (8 M urea, 100 mM NaH$_2$PO$_4$, 10 mM Tris, 80 mM imidazole, pH 8.0) and then the dNP2-LRR fusion protein was eluted using an elution buffer (8 M urea, 100 mM NaH$_2$PO$_4$, 10 mM Tris, 250 mM imidazole, pH 8.0). The isolated dNP2-LRR fusion protein was desalted using a PD-10 Sephadex G-25 column (GE Healthcare, Chicago, Ill., USA). To eliminate bacterial endotoxin contamination in the purified dNP2-LRR fusion protein, the purified dNP2-LRR fusion protein was incubated in a medium containing 1% Triton X-114 for 30 minutes at 4° C. The recovered medium was centrifuged to separate an aggregate. The dNP2-LRR fusion protein was isolated and purified by repeating this process 4 times. The dNP2-LRR fusion protein recovered through the process described above was finally desalted using a PD-10 Sephadex G-25 column (GE Healthcare, Chicago, Ill., USA) and stored at −80° C. in HBSS (Hank's balanced salt solution) containing 10% glycerol after quantification of protein concentration by the Bradford assay (Bio-Rad, Hercules, Calif., USA).

Comparative Example 1 Purification and Isolation of dNP2-NBD Fusion Protein

A dNP2-NBD fusion protein was prepared in the same manner as in Example 1, except that an insert DNA of dNP2-NBD (SEQ ID NO 7) was inserted into the pET28a vector.

Comparative Example 2 Purification and Isolation of dNP2-EGFP Fusion Protein

A dNP2-EGFP fusion protein was prepared in the same manner as in Example 1, except that an insert DNA of dNP2-EGFP was inserted into the pET28a vector.

Comparative Example 3 Purification and Isolation of TAT-LRR Fusion Protein

A TAT-LRR fusion protein was prepared in the same manner as in Example 1, except that an insert DNA of TAT-LRR (SEQ ID NO 8) was inserted into the pET28a vector.

The experimental data were statistically analyzed using the Prism 7 software (GraphPad, San Diego, Calif., USA). Tests for statistical significance were performed using two-tailed Student's t-test, one-way ANOVA or two-way ANOVA. Results with P-values less than 0.05 were considered statistically significant.

Test Example 1 Size Analysis of dNP2 Peptide-Bound Fusion Protein

The NLRX1 protein is composed of an LRR domain, an NBD domain and an N-terminal mitochondrial targeting sequence (MTS). Therefore, functional motifs that can elucidate the function and structure of the regions of the NLRX1 protein and allow its use as a therapeutic agent were presented, and DNA constructs that can express them were designed and prepared (FIG. 1).

Figure 2:
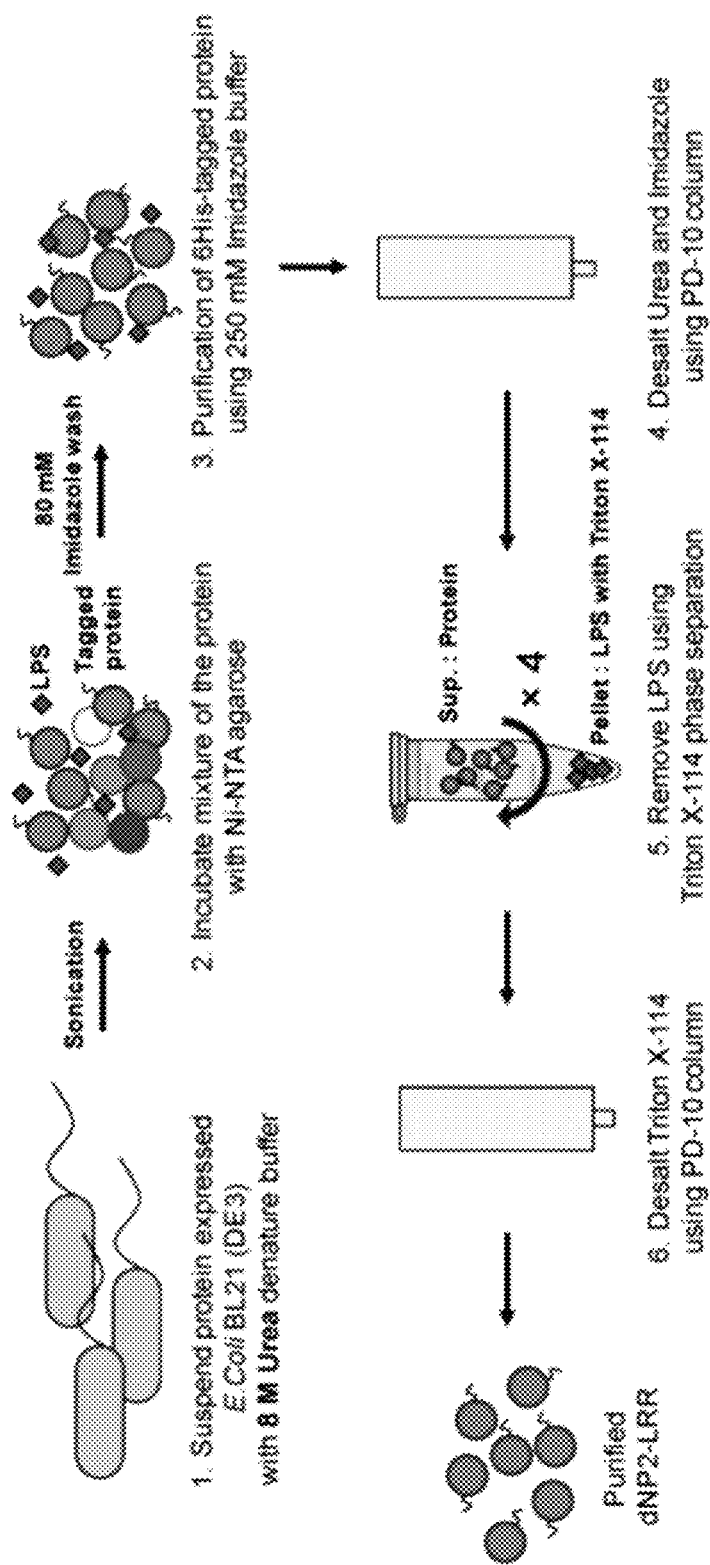
FIG. 2 shows a procedure of isolating and purifying a dNP2-LRR fusion protein with high purity.

The dNP2-LRR (Example 1), dNP2-NBD (Comparative Example 1) and dNP2-EGFP (Comparative Example 2) fusion proteins were expressed in E. coli and the 6His-tagged proteins were purified by affinity chromatography under denaturing conditions and the bacterial LPS was removed by Triton X-114 phase separation (performed 4 times) (FIG. 2).

The dNP2-LRR fusion protein of Example 1, dNP2-NBD of Comparative Example 1, dNP2-EGFP of Comparative Example 2 and a control group (LRR) were analyzed by SDS-PAGE. The result is shown in FIG. 3.

Figure 3:
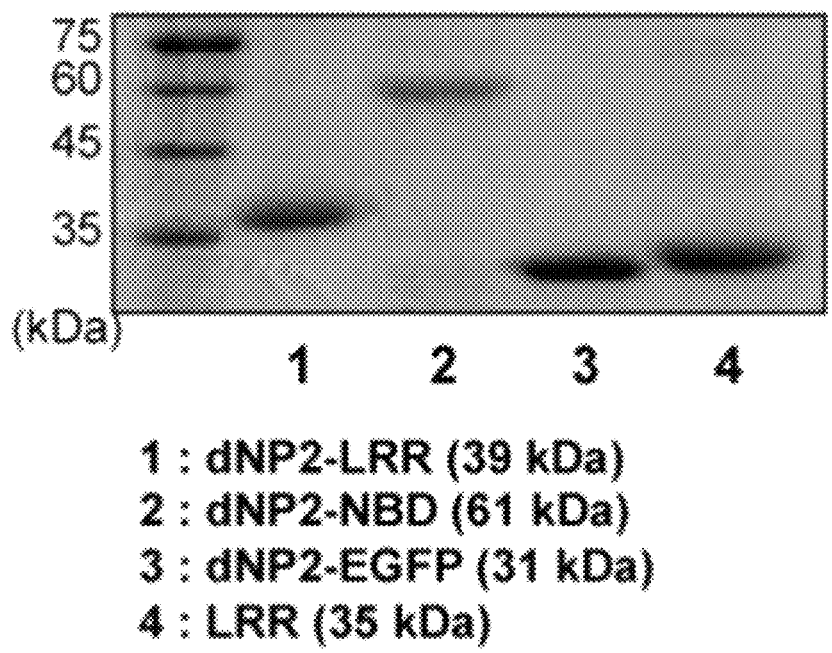
FIG. 3 shows a result of analyzing a dNP2-LRR fusion protein of Example 1, dNP2-NBD of Comparative Example 1, dNP2-EGFP of Comparative Example 2 and a control group (LRR) on 12% SDS-PAGE gel.

As seen from FIG. 3, the dNP2-LRR fusion protein of Example 1 was identified as 39 kDa, the dNP2-NBD fusion protein of Comparative Example 1 as 61 kDa, the dNP2-EGFP fusion protein of Comparative Example 2 as 31 kDa, and the control group (LRR) as 35 kDa.

Test Example 2 Evaluation of Cytotoxic Effect of Fusion Protein

The degree of endotoxin contamination when RAW264.7 cells were treated with the dNP2-LRR fusion protein of Example 1 was analyzed. For this, after preparing a dNP2-LRR fusion protein (Tripton) not treating with Triton X-114 as a comparison group and treating RAW264.7 macrophages with the same, the concentration of expressed IL-6 was measured by ELISA 12 hours later. The result is shown in FIG. 4.

Figure 4:
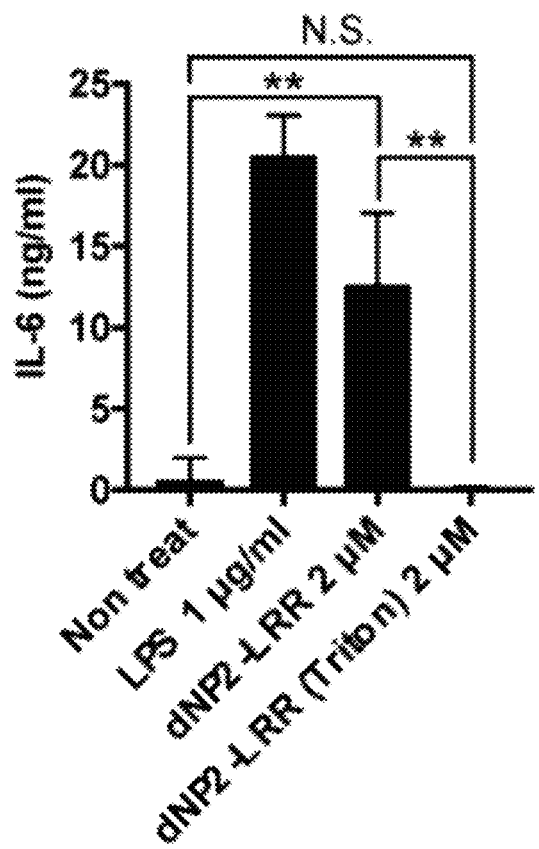
FIG. 4 shows a result of analyzing the degree of endotoxin contamination when RAW264.7 cells were treated with a dNP2-LRR fusion protein of Example 1. Specifically, after treating RAW264.7 cells with LPS, a dNP2-LRR fusion protein of Example 1 or a dNP2-LRR fusion protein of Example 1 (Tripton) and then culturing for 12 hours, the concentration of expressed IL-6 was measured by ELISA. n=2 per each group, and error bars indicate S.D. **$P<0.01$, N.S.: not significant.

FIG. 4 shows a result of treating the RAW264.7 cells with the dNP2-LRR fusion protein of Example 1 and analyzing the degree of endotoxin contamination. Specifically, after treating the RAW264.7 cells with LPS, the dNP2-LRR fusion protein of Example 1 or the dNP2-LRR fusion protein of Example 1 (Tripton) and culturing for 12 hours, the concentration of expressed IL-6 was measured by ELISA. n=2 and error bars indicate S.D. **P<0.01, N.S.: not significant.

As shown in FIG. 4, for the dNP2-LRR fusion protein of Example 1, the IL-6 concentration in the RAW264.7 cells was not increased because LPS was removed completely. In contrast, for the dNP2-LRR fusion protein (Tripton), IL-6 was increased significantly in the RAW264.7 cells. This suggests that endotoxin contamination still remains.

Test Example 3 Analysis of 3D Structure of dNP2-LRR Fusion Protein of Example 1

The structure of the dNP2-LRR fusion protein of Example 1 was predicted using SparksX. (available online: sparks-lab.org/yueyang/server/SPARKS-X/).

Figure 5:
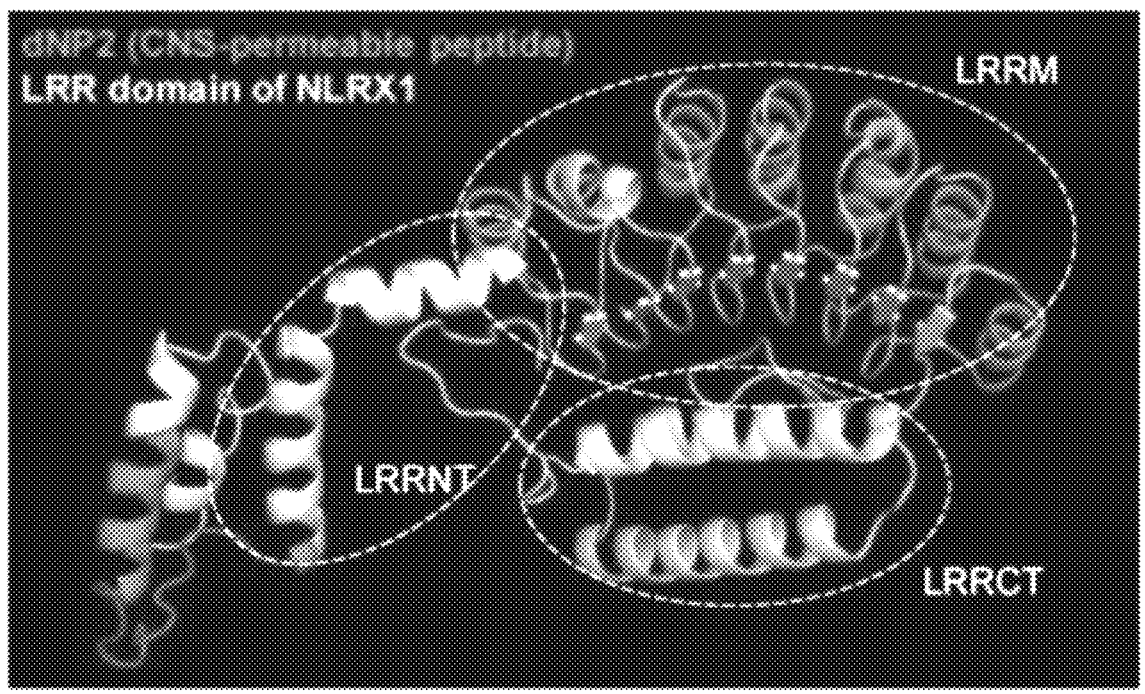
FIG. 5 shows the 3D structure of a dNP2-LRR fusion protein of Example 1.

FIG. 5 shows the 3D structure of the dNP2-LRR fusion protein of Example 1. The alpha-helical structure of the dNP2 peptide has been highlighted in red, with the LRR domain of NLRX1 in green. It was confirmed from the 3D structure of the dNP2-LRR fusion protein of Example 1 of the present disclosure that the LRR domain structure matches with the previously reported LRR structure.

Test Example 4 Effect of Delivery of dNP2-LRR Fusion Protein of Example 1 into T Cells-1

1) Methods

Jurkat cells ($4 \times 10^5$ cells per well) were seeded into a 96-well plate and incubated with fusion proteins at various concentrations (0.5 μM, 1 μM or 2 μM) for 1 hour or at 2 μM concentration different times (10 minutes, 30 minutes, 1 hour, 2 hours, 6 hours or 12 hours). The fusion proteins were the dNP2-LRR fusion protein of Example 1, the TAT-LRR fusion protein of Comparative Example 3 and a control group (LRR).

After the incubation was completed, the cells were harvested and washed once with PBS. To remove membrane-bound fusion proteins from the cells, they were treated with trypsin at 37° C. for 5 minutes. After washing again with PBS, the washed cells were fixed and permeabilized with a BD fix/perm kit and intracellular proteins were stained with α-6His rabbit monoclonal antibody (Abcam, Cambridge, UK) and α-rabbit IgG Alexa Fluor 647 antibody (Invitrogen, Carlsbad, Calif., USA). Intracellular fluorescence was analyzed by flow cytometry.

For western blotting, Jurkat cells were lysed with a RIPA buffer (Cell Signaling Technology, Danvers, Mass., USA) containing 1 mM PMSF and NaF on ice for 30 minutes. Total protein concentration was analyzed with a Pierce BCA protein assay kit (Thermo Fisher Scientific, Waltham, Mass., USA). After conducing electrophoresis (SDS-PAGE) using the cell lysate, the proteins were transferred onto a PVDF membrane (Bio-Rad, Hercules, Calif., USA). Next, the PVDF membrane was blocked with 5% skim milk in Tris-buffered saline containing 0.1% Tween-20 and incubated with α-6His rabbit monoclonal antibody (Abcam) and α-rabbit IgG-HRP (Cell Signaling Technology, MA, USA, MA). After washing and treating with an EZ-Western Lumi Pico or Femto reagent (DoGen, Seoul, Republic of Korea), band intensity was measured with Fusion-Solo (Vilber, Collégien, France).

2) Results

It was investigated whether the fusion protein according to the present disclosure is delivered effectively into T cells. Jurkat T cells were treated with the dNP2-LRR fusion protein of Example 1, the dNP2-EGFP of Comparative Example 2 or a control group (LRR) at various concentrations (0.5-2 μM). Jurkat T cells are human T lymphocytes. The intracellular protein level was analyzed by flow cytometry and western blot using anti-6His primary antibody and Alexa Fluor 647-labeled anti-rabbit secondary antibody. The result is as follows.

Figure 6:
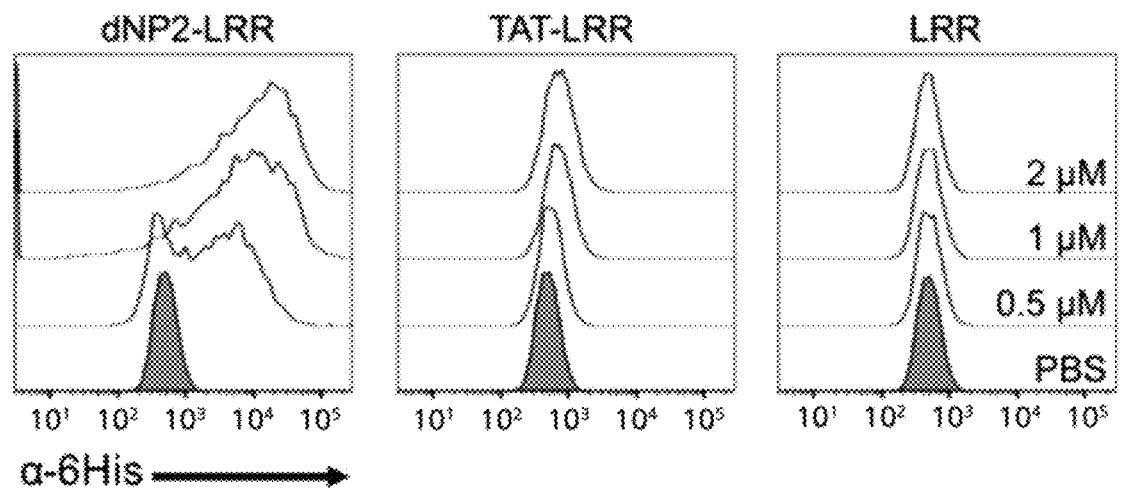
FIGS. 6 and 7 show a result of incubating Jurkat T cells with a dNP2-LRR fusion protein of Example 1, a TAT-LRR fusion protein of Comparative Example 3 or a control group (LRR) at 0.5, 1 and 2 μM, respectively, for 1 hour and conducting flow cytometry.
Figure 7:
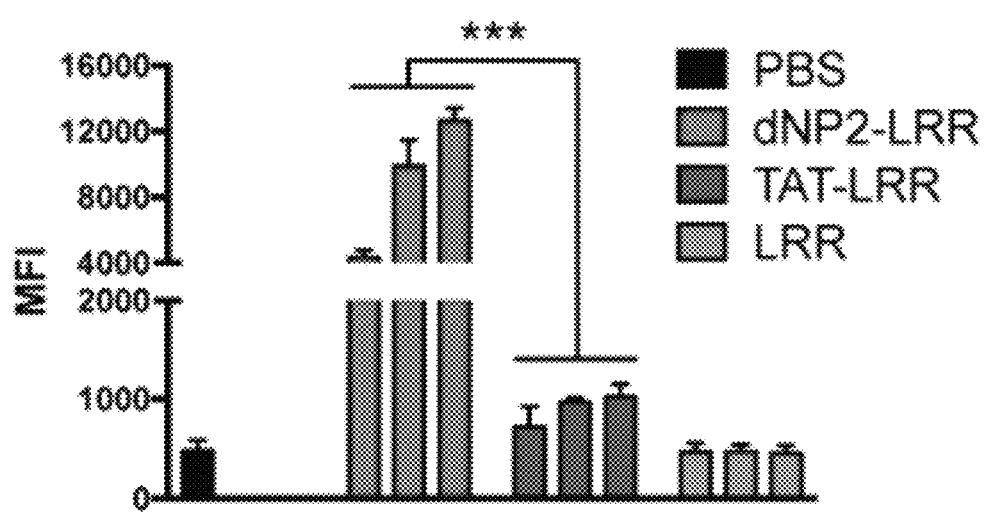

FIGS. 6 and 7 show the result of incubating Jurkat T cells with the dNP2-LRR fusion protein of Example 1, the TAT-LRR fusion protein of Comparative Example 3 or the control group (LRR) at 0.5, 1 and 2 μM, respectively, for 1 hour and conducting flow cytometry. The excrement was repeated 3 times (n=3) and error bars indicate S.D. ***P<0.001. MFI means mean fluorescence intensity.

From FIGS. 6 and 7, it was confirmed that intracellular delivery efficiency is increased as the concentration of the fusion protein of a LRR domain derived from the NLRX1 protein and a dNP2 peptide (Example 1) is increased. The efficiency was remarkably higher than those of the TAT-LRR fusion protein of Comparative Example 3 and the control group (LRR).

Figure 8:
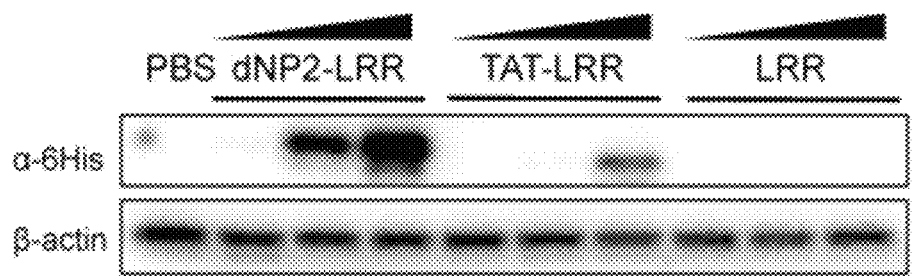
FIG. 8 shows a result of incubating Jurkat T cells with a dNP2-LRR fusion protein of Example 1, a TAT-LRR fusion protein of Comparative Example 3 or a control group (LRR) for 1 hour and then analyzing the LRR protein existing in the cells by western blot.

FIG. 8 shows the result of incubating Jurkat T cells with the dNP2-LRR fusion protein of Example 1, the TAT-LRR fusion protein of Comparative Example 3 or the control group (LRR) for 1 hour and then analyzing the LRR protein existing in the cells by western blot.

From FIG. 8, it was confirmed that the intracellular delivery efficiency is increased as the concentration of the fusion protein of a LRR domain derived from the NLRX1 protein and a dNP2 peptide (Example 1) is increased. The efficiency was remarkably higher than those of the TAT-LRR fusion protein of Comparative Example 3 and the control group (LRR).

Figure 9:
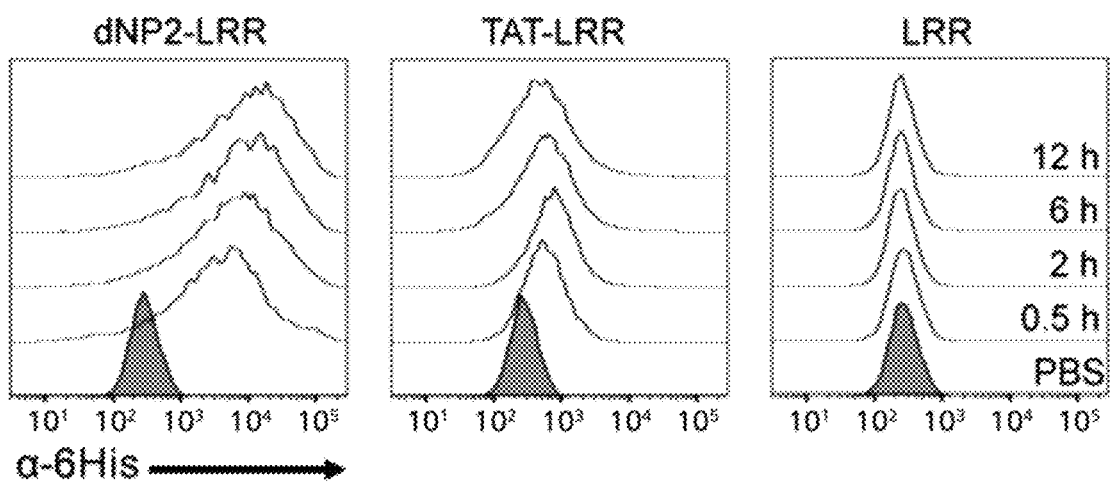
FIG. 9 and FIG. 10 show a result of incubating Jurkat T cells with a dNP2-LRR fusion protein of Example 1, a TAT-LRR fusion protein of Comparative Example 3 or a control group (LRR) for different times (0, 0.5, 2, 6 and 12 hours) and then analyzing intracellular fluorescence by flow cytometry.
Figure 10:
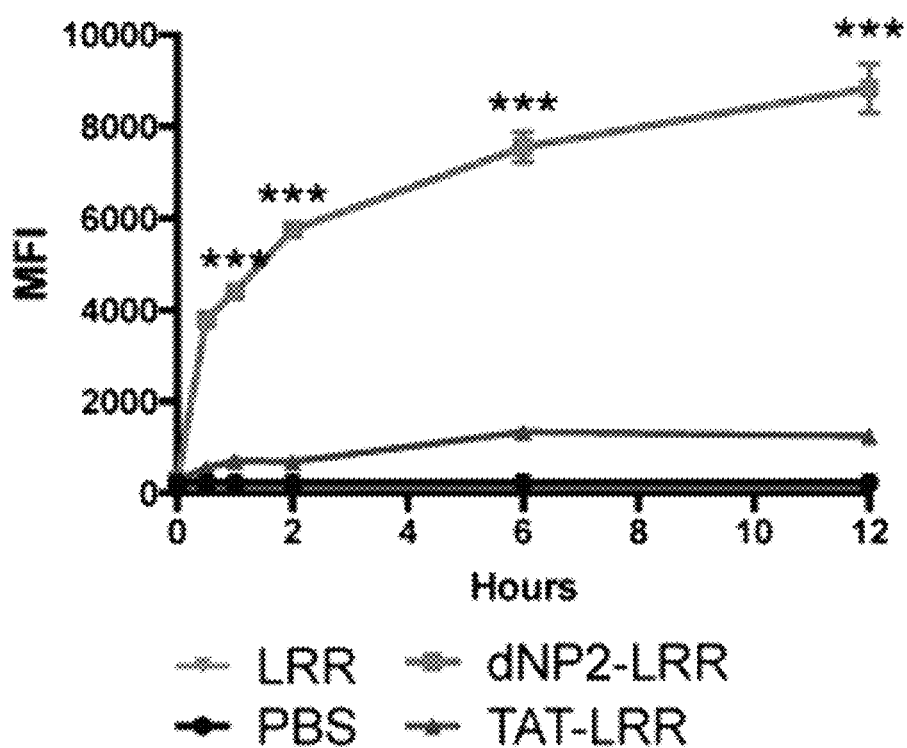

FIG. 9 and FIG. 10 show the result of incubating Jurkat T cells with the dNP2-LRR fusion protein of Example 1, the TAT-LRR fusion protein of Comparative Example 3 or the control group (LRR) for different times (0, 0.5, 2, 6 and 12 hours) and then analyzing intracellular fluorescence by flow cytometry. The excrement was repeated 3 times (n=3) and error bars indicate S.D. ***P<0.001. MFI means mean fluorescence intensity.

From FIG. 9 and FIG. 10, it was confirmed that the most significant effect is achieved when the dNP2-LRR fusion protein of Example 1 was treated for 0.5 hour and the effect is increased as the incubation time is increased. In contrast, for the TAT-LRR fusion protein of Comparative Example 3, delivery effect was observed vaguely from 2 hours. A significant effect was observed from 6 hours and no significant change was observed with time. In particular, the effect was decreased greatly from 12 hours.

This suggests that the dNP2-LRR fusion protein of Example 1 has stronger intracellular protein transduction ability than the TAT-LRR fusion protein of Comparative Example 3 in T cells. That is to say, whereas the LRR domain derived from the LNRX1 protein is not delivered into cells when bound to the existing cell-penetrating peptide, it has remarkably superior intracellular protein transduction ability when bound to the dNP2 peptide.

Test Example 5 Effect of Delivery of dNP2-LRR Fusion Protein of Example 1 into T Cells-2

1) Methods

For analyzing the localization of the dNP2-LRR fusion protein in HeLa cells, $1 \times 10^5$ cells per well were incubated with 0.2 μM of the fusion protein at 37° C. for 1 hour. The cells were then washed 3 times with PBS and mitochondria were stained with 400 nM of Mitotracker cmsROX (Thermo Fisher Scientific, Waltham, Mass., USA) at 37° C. for 15 minutes. The cells were washed 3 times with PBS and fixed with 4% paraformaldehyde. Then, the cells were permeabilized by 0.25% Triton X-100 and intracellular proteins were stained with α-6His rabbit monoclonal antibody (Abcam, Cambridge, UK) and α-rabbit IgG Alexa Fluor 488 antibody (Invitrogen, Carlsbad, Calif., USA). The fluorescence in the cytoplasm and the nucleus was analyzed with a C2si confocal microscope (Nikon, Tokyo, Japan). As the fusion proteins, the dNP2-LRR fusion protein of Example 1, the TAT-LRR fusion protein of Comparative Example 3 and a control group (LRR) were used.

2) Conclusion

Figure 11:
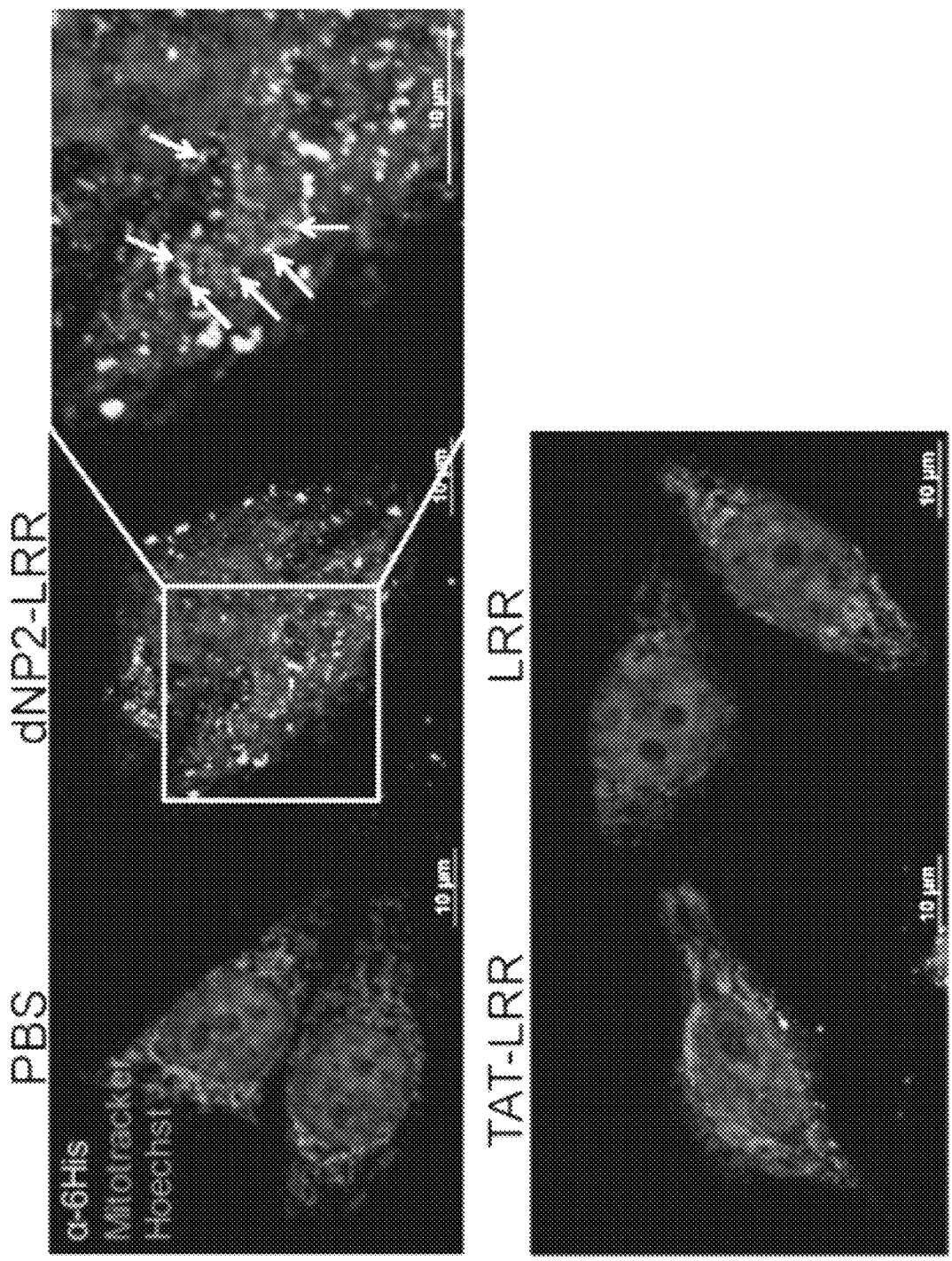
FIG. 11 shows confocal microscopic images obtained after treating HeLa cells with a dNP2-LRR fusion protein of Example 1, a TAT-LRR fusion protein of Comparative Example 3 or a control group (LRR).

FIG. 11 shows the confocal microscopic images obtained after treating the HeLa cells with the dNP2-LRR fusion protein of Example 1, the TAT-LRR fusion protein of Comparative Example 3 or the control group (LRR). In the HeLa cells, the dNP2-LRR fusion protein of Example 1 was observed in both the cytoplasm and the nucleus and a small portion was observed also in the mitochondria. In contrast, the TAT-LRR fusion protein of Comparative Example 3 and the control group (LRR) were detected only on the surface of the HeLa cells and were hardly detected inside the cells. Through this, it can be seen that the LRR domain can be effectively delivered into cells only by the dNP2 peptide.

Test Example 6 Effect of Delivery of dNP2-LRR Fusion Protein of Example 1 into T Cells-3

1) Methods

Mouse splenocytes (1×10$^6$ cells per well) were seeded into a 24-well plate and incubated with a fusion protein at a concentration of 2 μM for 1 hour. As the fusion protein, the dNP2-LRR fusion protein of Example 1, the TAT-LRR fusion protein of Comparative Example 3 and a control group (LRR) were used.

After the incubation was completed, the cells were harvested and washed once with PBS. To remove membrane-bound fusion proteins from the cells, they were trypsinized at 37° C. for 5 minutes. After washing again with PBS, the washed cells were fixed and permeabilized by a BD fix/perm kit and intracellular proteins were stained with α-6His rabbit monoclonal antibody (Abcam, Cambridge, UK) and α-rabbit IgG Alexa Fluor 647 antibody (Invitrogen, Carlsbad, Calif., USA). Intracellular fluorescence was measured by flow cytometry.

Figure 12:
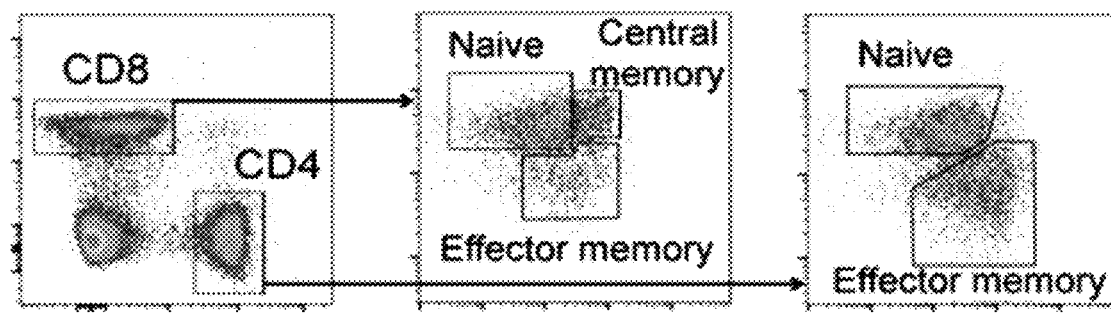
FIG. 12 shows the gating strategy of T cells in splenocytes. Specifically, after incubating splenocytes with a dNP2-LRR fusion protein of Example 1, a TAT-LRR fusion protein of Comparative Example 3 or a control group (LRR) at 2 μM for 1 hour, intracellular delivery efficiency was analyzed by flow cytometry after staining with specific markers.

In this experiment, the T cell population was classified as $CD62L^{high}CD44^{low}$ naive CD4$^+$ T cells, $CD62L^{high}CD44^{low}$ effector/memory CD4$^+$ T cells, CD8$^+$ T cell subsets as $CD62L^{high}CD44^{low}$ naive CD8$^+$ T cells, $CD62L^{low}CD44^{high}$ effector/memory CD8$^+$ T cells and $CD62L^{high}CD44^{high}$ central memory CD8$^+$ T cells (FIG. 12).

2) Conclusion

Figure 13:
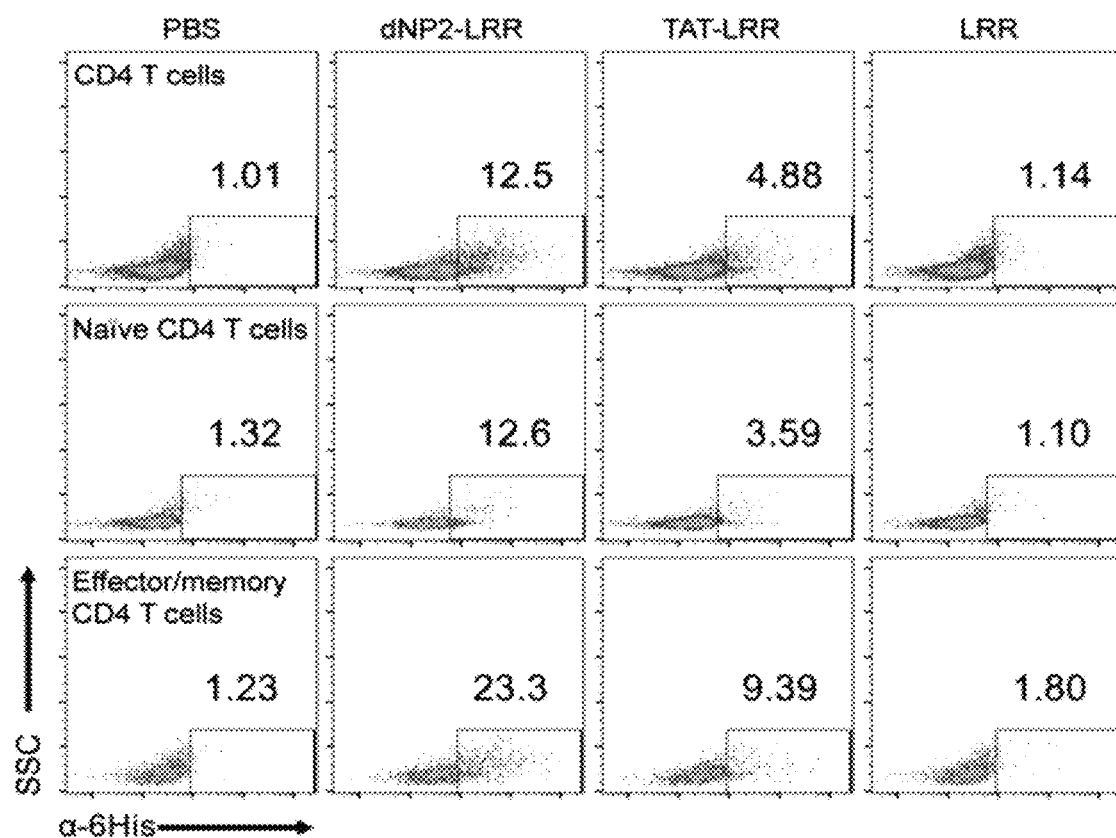
FIG. 13 shows a result of incubating CD4 T cells with a dNP2-LRR fusion protein of Example 1, a TAT-LRR fusion protein of Comparative Example 3 or a control group (LRR) and conducting analysis according to the gating strategy of FIG. 12.
Figure 14:
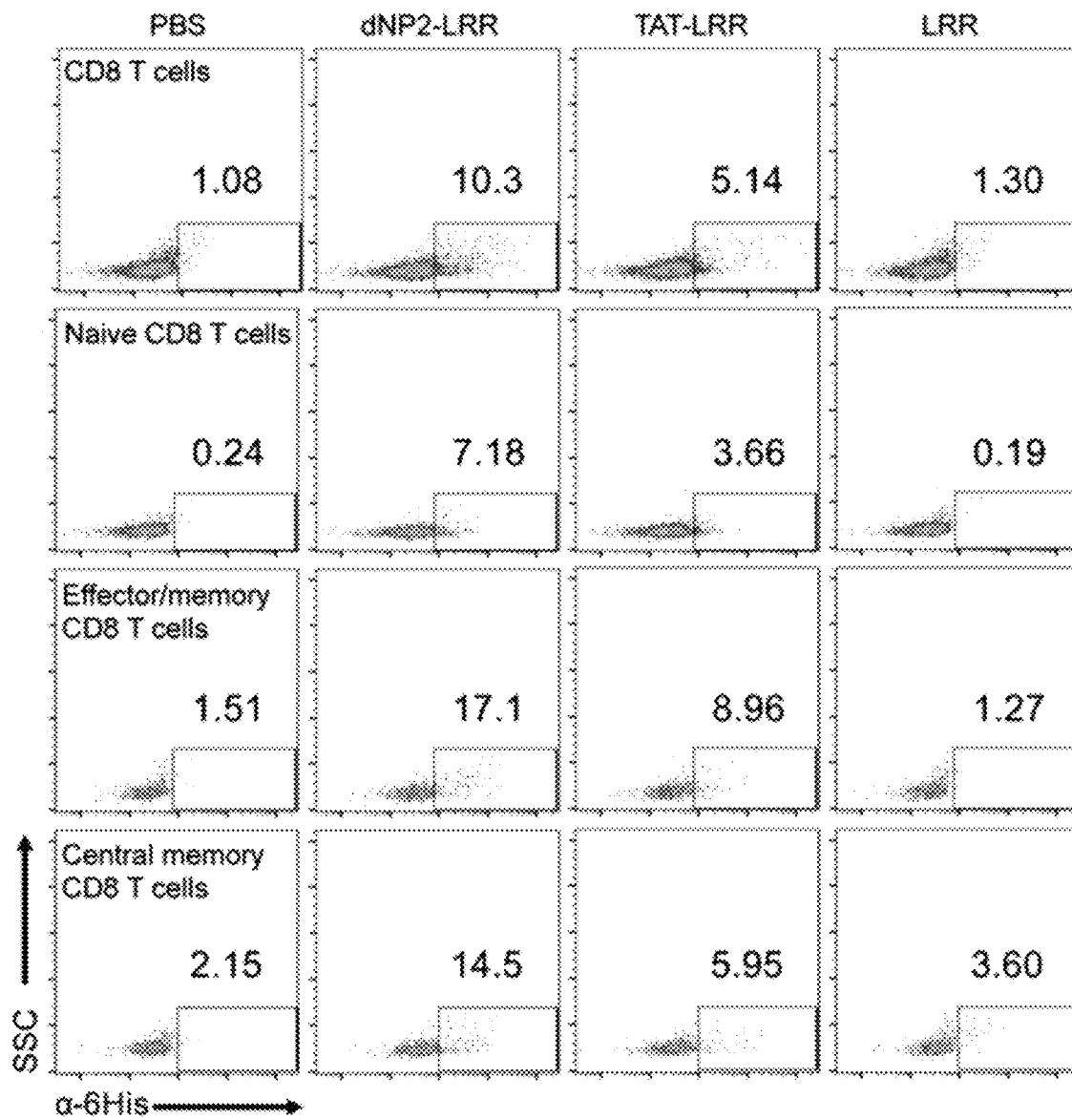
FIG. 14 shows a result of incubating CD8 T cells with a dNP2-LRR fusion protein of Example 1, a TAT-LRR fusion protein of Comparative Example 3 or a control group (LRR) and conducting analysis according to the gating strategy of FIG. 12.
Figure 15:
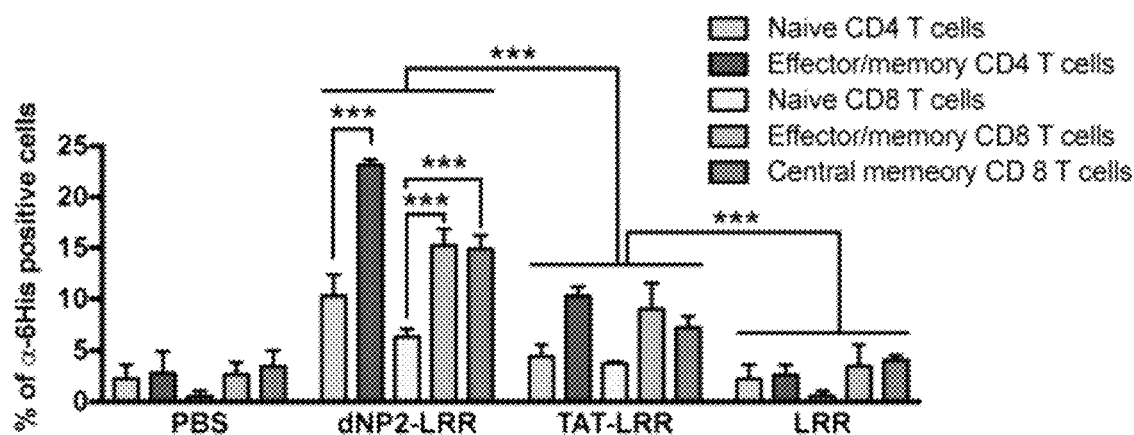
FIG. 15 shows a result of quantifying the results of FIG. 13 and FIG. 14. n=3 per each group and error bars indicate S.D. ***$P<0.001$. MFI means mean fluorescence intensity.

FIG. 12 shows the gating strategy of T cells in splenocytes. Specifically, after incubating splenocytes with the dNP2-LRR fusion protein of Example 1, the TAT-LRR fusion protein of Comparative Example 3 or a control group (LRR) at 2 μM for 1 hour, intracellular delivery efficiency was analyzed by flow cytometry after staining with specific markers. FIG. 13 shows the result of incubating CD4 T cells with the dNP2-LRR fusion protein of Example 1, the TAT-LRR fusion protein of Comparative Example 3 or the control group (LRR) and conducting analysis according to the gating strategy of FIG. 12. FIG. 14 shows the result of incubating CD8 T cells with the dNP2-LRR fusion protein of Example 1, the TAT-LRR fusion protein of Comparative Example 3 or the control group (LRR) and conducting analysis according to the gating strategy of FIG. 12. FIG. 15 shows a result of quantifying the results of FIG. 13 and FIG. 14. The experiment was repeated 3 times (n=3) and error bars indicate S.D. ***P<0.001.

From FIG. 13, FIG. 14 and FIG. 15, it can be seen that, in total CD4$^+$ T cells, the dNP2-LRR fusion protein of Example 1 showed remarkably higher proportion of intracellular LRR proteins than the proportion of the TAT-LRR fusion protein of Comparative Example 3 or the control group (LRR).

The delivery effect in effector/memory cells was significantly higher than in naive cells. Similarly to CD4$^+$ T cells, the dNP2-LRR fusion protein of Example 1 also had higher delivery effect than the TAT-LRR fusion protein of Comparative Example 3 also in CD8$^+$ T cells. The intracellular delivery effect was significantly high both in effector/memory cells and naive cells. Through this, it was confirmed that the dNP2-LRR fusion protein of Example 1 is delivered into T cells very effectively.

Test Example 7 Effect of Preventing Neurological Autoimmune Disease of dNP2-LRR Fusion Protein of Example 1-1

1) Animal Model

All mice (C57BL/6J) were maintained in a pathogen-free facility at Hanyang University. The animal experiment protocol used in this study was approved by the Animal Experimentation Ethics Committee of Hanyang University, and all experiments were performed according to the guidelines of the Institutional Animal Care and Use Committee of Hanyang University.

10-week-old female C57BL/6 mice were purchased from Orient Bio. An experimental autoimmune encephalitis (EAE) animal model was induced by immunization with $MOG_{35-55}$ antigen (Hooke Labs, Lawrence, Mass., USA) and 100 ng injection of pertussis toxin (PT).

Figure 16A:
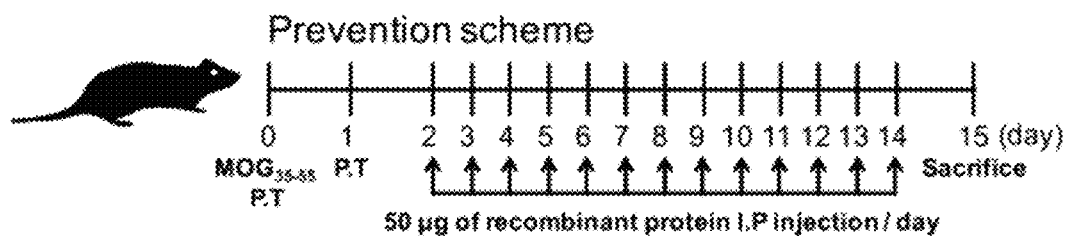
FIG. 16A describes an experimental scheme for analyzing the preventive effect of Test Example 7 and Test Example 8 for an EAE animal model of a neurological autoimmune disease.

For analysis of preventive effect, a prevention scheme model was designed as follows. After immunization, 50 μg of a fusion protein was intraperitoneally injected to the mice every day, from day 2 to until they were sacrificed. Then, the animals were scored every day for the signs of clinical disease (Stromnes I M, Goverman J M. Active induction of experimental allergic encephalomyelitis. Nat Protoc. 2006; 1: 1810-9). Spinal cord tissues were harvested from the animal model and analyzed by histology, flow cytometry and real-time polymerase chain reaction (RT-PCR) (FIG. 16A).

As the fusion protein, the dNP2-LRR fusion protein of Example 1, the TAT-LRR fusion protein of Comparative Example 3 and a control group (LRR) were used.

2) RT-PCR

The spinal cord tissues obtained from each group were disrupted with a homogenizer equipped with RNAiso plus (Takara, Kusatsu, Japan) and total RNA was extracted. cDNA was synthesized with ReverTra Ace qPCR RT master mix (Toyobo, Osaka, Japan). RT-PCR was performed on a CFX Connect RT-PCR detection system (Bio-Rad, Hercules, Calif., USA) using iQ SYBR Green Supermix (Bio-Rad, CA, USA). The following primers were used:

```
<mIl6>
Forward (SEQ ID NO 14):
5'-AGGATACCACTCCCAACAGACCT-3'

Reverse (SEQ ID NO 15):
3'-CAAGTGCATCATCGTTGTTACTAC-5'
```

-continued

```
<mTnfa>
Forward (SEQ ID NO 16):
5'-CATCTTCTCAAAATTCGAGTGACAA-3'

Reverse (SEQ ID NO 17):
3'-CCCAACATGGAACAGATGAGGGT-5'

<mIl1b>
Forward (SEQ ID NO 18):
5'-GAAATGCCACCTTTTGACAGTG-3'

Reverse (SEQ ID NO 19):
3'-TGGATGCTCTCATCAGGACAG-5'

<mIfng>
Forward (SEQ ID NO 20):
5'-ATGAACGCTACACACTGCATC-3'

Reverse (SEQ ID NO 21):
3'-CCATCCTTTTGCCAGTTCCTC-5'

<ml717a>
Forward (SEQ ID NO 22):
5'-TTTAACTCCCTTGGCGCAAAA-3'

Reverse (SEQ ID NO 23):
3'-CTTTCCCTCCGCATTGACAC-5'

<mGmcsf>
Forward (SEQ ID NO 24):
5'-GGCCTTGGAAGCATGTAGAGG-3'

Reverse (SEQ ID NO 25):
3'-GGAGAACTCGTTAGAGACGACTT-5'

<mActb>
Forward (SEQ ID NO 26):
5'-TGTCCCTGTATGCCTCTGGT-3'

Reverse (SEQ ID NO 27):
3'-CACGCACGATTTCCCTCTC-5'
```

3) Conclusion

For the groups prepared by treating the animal model with the dNP2-LRR fusion protein of Example 1, the dNP2-NBD fusion protein of Comparative Example 1 and the dNP2-EGFP fusion protein of Comparative Example 2, the signs of clinical disease were scored every day (Stromnes I M, Goverman J M. Active induction of experimental allergic encephalomyelitis. *Nat Protoc.* 2006; 1: 1810-9). Spinal cord tissues were harvested from the animal model and analyzed by histology. The result is shown in FIG. 17.

Figures 17, 18:
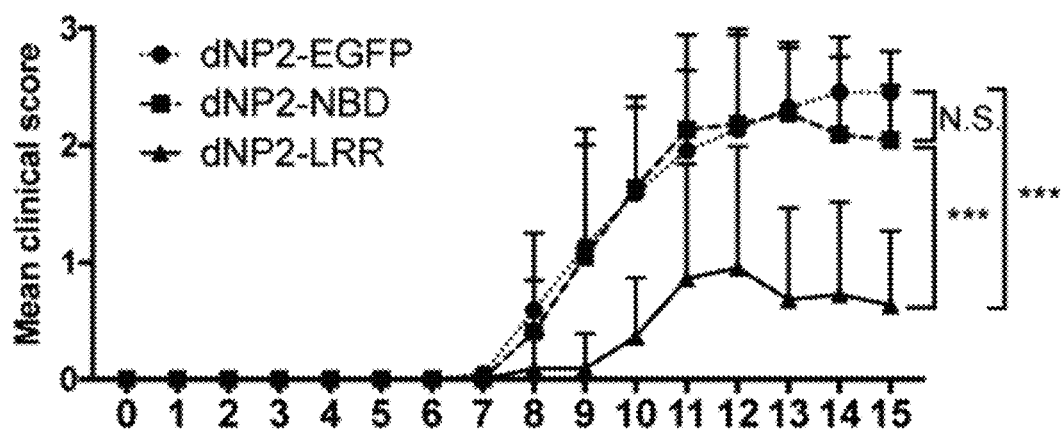
FIG. 17 shows a result of treating a prevention scheme model with a dNP2-LRR fusion protein of Example 1, a dNP2-NBD fusion protein of Comparative Example 1 or a dNP2-EGFP fusion protein of Comparative Example 2 and analyzing clinical scores every day. n=11 and error bars indicate S.D. *$P<0.05$, $P<0.01$ and *$P<0.001$. N.S.: not significant.
FIG. 18 shows a result of treating a prevention scheme model with a dNP2-LRR fusion protein of Example 1, a dNP2-NBD fusion protein of Comparative Example 1 or a dNP2-EGFP fusion protein of Comparative Example 2 and analyzing disease incidence rate and day of onset for each group.

FIG. 17 shows the result of treating the prevention scheme model with the dNP2-LRR fusion protein of Example 1, the dNP2-NBD fusion protein of Comparative Example 1 or the dNP2-EGFP fusion protein of Comparative Example 2 and analyzing clinical scores every day. n=11 and error bars indicate S.D. *$P<0.05$, $P<0.01$ and *$P<0.001$. N.S.: not significant.

FIG. 18 shows the result of treating the prevention scheme model with the dNP2-LRR fusion protein of Example 1, the dNP2-NBD fusion protein of Comparative Example 1 or the dNP2-EGFP fusion protein of Comparative Example 2 and analyzing disease incidence rate and day of onset for each group.

From FIG. 17 and FIG. 18, it was confirmed that, when the dNP2-LRR fusion protein of Example 1, the dNP2-NBD fusion protein of Comparative Example 1 or the dNP2-EGFP fusion protein of Comparative Example 2 was intraperitoneally administered every day to the $MOG_{35-55}$ immunization animal model from day 2 and clinical symptoms were monitored until the day of sacrifice, i.e., day 15, the clinical score and the incidence were reduced significantly by the treatment with the dNP2-LRR fusion protein of Example 1. In contrast, no disease prevention effect was observed with the dNP2-NBD fusion protein of Comparative Example 1 or the dNP2-EGFP fusion protein of Comparative Example 2.

After isolating spinal cord tissues from the groups prepared by treating the animal model with the dNP2-LRR fusion protein of Example 1, the dNP2-NBD fusion protein of Comparative Example 1 or the dNP2-EGFP fusion protein of Comparative Example 2, they were analyzed by histology. Detailed procedures are as follows. The spinal cord tissues isolated from each group were embedded in paraffin blocks and subsequently fixed with 4% paraformaldehyde. The paraffin blocks were sliced and stained with Luxol fast blue (LFB) and hematoxylin. The stained tissues were analyzed using a DMi8 microscope (Leica, Wetzlar, Germany). The result is shown in FIG. 19.

Figure 19:
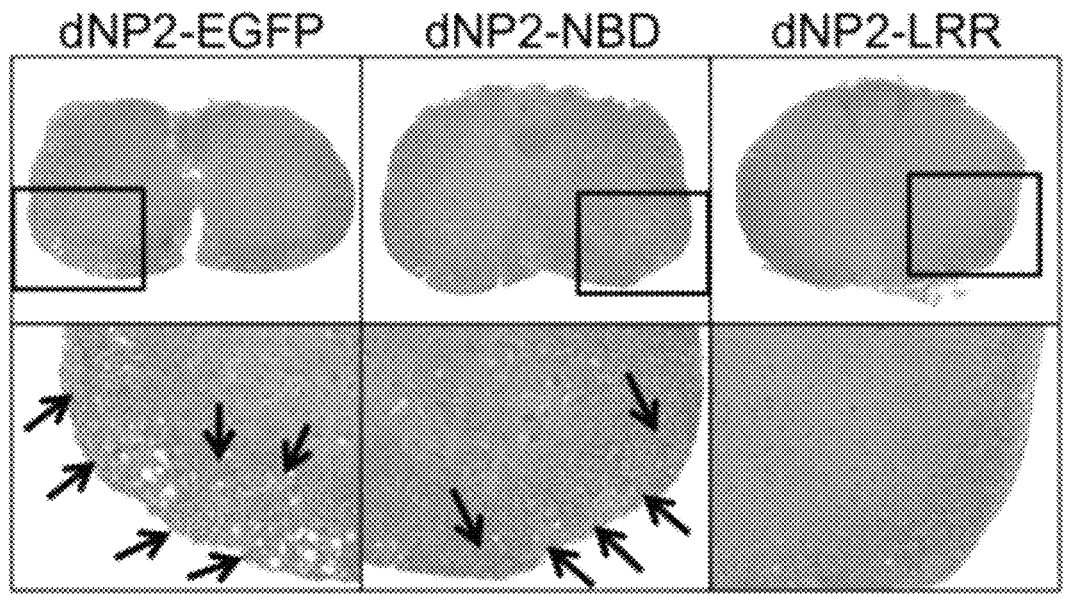
FIG. 19 shows a result of treating a prevention scheme model with a dNP2-LRR fusion protein of Example 1, a dNP2-NBD fusion protein of Comparative Example 1 or a dNP2-EGFP fusion protein of Comparative Example 2 and staining the spinal cord tissues obtained from each group with LFB and hematoxylin.

FIG. 19 shows a result of treating the prevention scheme model with the dNP2-LRR fusion protein of Example 1, the dNP2-NBD fusion protein of Comparative Example 1 or the dNP2-EGFP fusion protein of Comparative Example 2 and staining the spinal cord tissues obtained from each group with LFB and hematoxylin.

Figure 20:
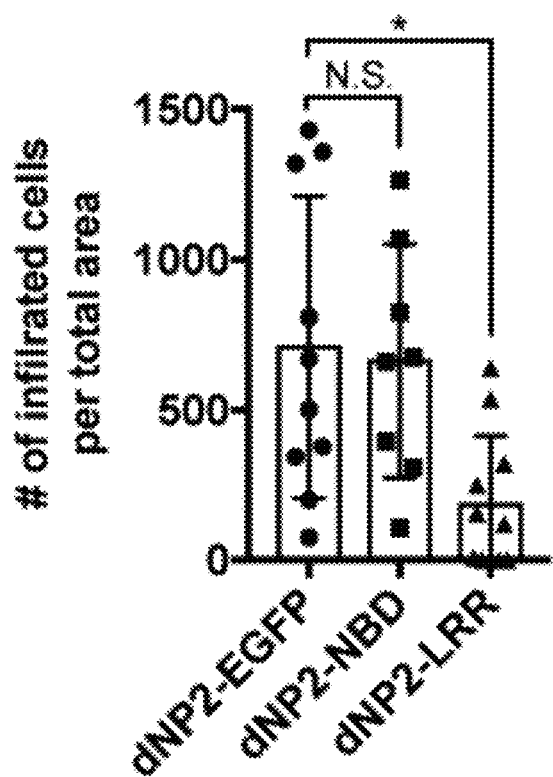
FIG. 20 shows a result of treating a prevention scheme model with a dNP2-LRR fusion protein of Example 1, a dNP2-NBD fusion protein of Comparative Example 1 or a dNP2-EGFP fusion protein of Comparative Example 2 and counting the number of infiltrated cells from the spinal cord tissues of each group. n=11 and error bars indicate S.D. *P<0.05, P<0.01 and *P<0.001. N.S.: not significant.

FIG. 20 shows a result of treating the prevention scheme model with the dNP2-LRR fusion protein of Example 1, the dNP2-NBD fusion protein of Comparative Example 1 or the dNP2-EGFP fusion protein of Comparative Example 2 and counting the number of infiltrated cells from the spinal cord tissues of each group. n=11 and error bars indicate S.D. *$P<0.05$, $P<0.01$ and *$P<0.001$. N.S.: not significant.

From FIG. 19 and FIG. 20, it can be seen that the treatment with the dNP2-LRR fusion protein of Example 1 significantly reduced demyelination and cell infiltration. In contrast, demyelination and cell infiltration were remarkably increased for the dNP2-NBD fusion protein of Comparative Example 1 and the dNP2-EGFP fusion protein of Comparative Example 2, suggesting that they exhibited no disease-preventing effect at all.

Through this, it was confirmed that the dNP2-LRR fusion protein of Example 1, not the dNP2-NBD fusion protein of Comparative Example 1, has a regulatory function in the progression of experimental autoimmune encephalomyelitis (EAE).

Test Example 8 Effect of Preventing Neurological Autoimmune Disease of dNP2-LRR Fusion Protein of Example 1-2

1) Animal Model

All mice (C57BL/6J) were maintained in a pathogen-free facility at Hanyang University. The animal experiment protocol used in this study was approved by the Animal Experimentation Ethics Committee of Hanyang University, and all experiments were performed according to the guidelines of the Institutional Animal Care and Use Committee of Hanyang University.

10-week-old female C57BL/6 mice were purchased from Orient Bio. An experimental autoimmune encephalitis (EAE) animal model was induced by immunization with $MOG_{35-55}$ antigen (Hooke Labs, Lawrence, Mass., USA) and 100 ng injection of pertussis toxin (PT).

For analysis of preventive effect, a prevention scheme model was designed as follows. After immunization, 50 μg of a fusion protein was intraperitoneally injected to the mice every day, from day 2 to until they were sacrificed. Then, the animals were scored every day for the signs of clinical disease (Stromnes I M, Goverman J M. Active induction of experimental allergic encephalomyelitis. *Nat Protoc.* 2006; 1: 1810-9). Spinal cord tissues were harvested from the animal model and analyzed by histology, flow cytometry and real-time polymerase chain reaction (RT-PCR) (FIG. 16A).

As the fusion protein, the dNP2-LRR fusion protein of Example 1, the dNP2-NBD fusion protein of Comparative Example 1 and the dNP2-EGFP fusion protein of Comparative Example 2 were used.

2) Flow Cytometry

After recovering spinal cord tissues from each group, lymphocytes were isolated from the spinal cord tissues by Percoll (GE Healthcare, IL, USA, USA) density-gradient centrifugation. Cells were stained with fluorochrome-conjugated monoclonal antibodies: mouse anti-CD45-Pacific blue (1:1000 diluted), anti-CD4-PE-Cy7 (1:1000 diluted), anti-CD8-PerCP-Cy5.5 (1:1000 diluted), anti-CD25-PE (1:1000 diluted), anti-CD69-FITC (1:1000 diluted), anti-CD44-APC-Cy7 (1:1000 diluted), anti-CXCR3-FITC (1:200 diluted), anti-CCR6-PE-Cy7 (1:200 diluted, BioLegend, San Diego, Calif., USA), anti-IFNγ-FITC (1:100 diluted), anti-IL-17A-PE (1:200 diluted), anti-FOXP3-APC (1:400 diluted, eBioscience, San Diego, Calif., USA) and anti-T-bet-PE (3 μL per sample, BD, Franklin Lakes, N.J., USA). Intracellular cytokine staining was performed using an Intracellular Fixation and Permeabilization kit (eBioscience, San Diego, Calif., USA) according to the manufacturer's instructions. The samples were run on a BD Canto II cytometer (BD Biosciences, San Jose, Calif., USA) and the results were analyzed using the FlowJo software version 10.1 (BD, Franklin Lakes, N.J., USA).

3) Conclusion

Figure 21:
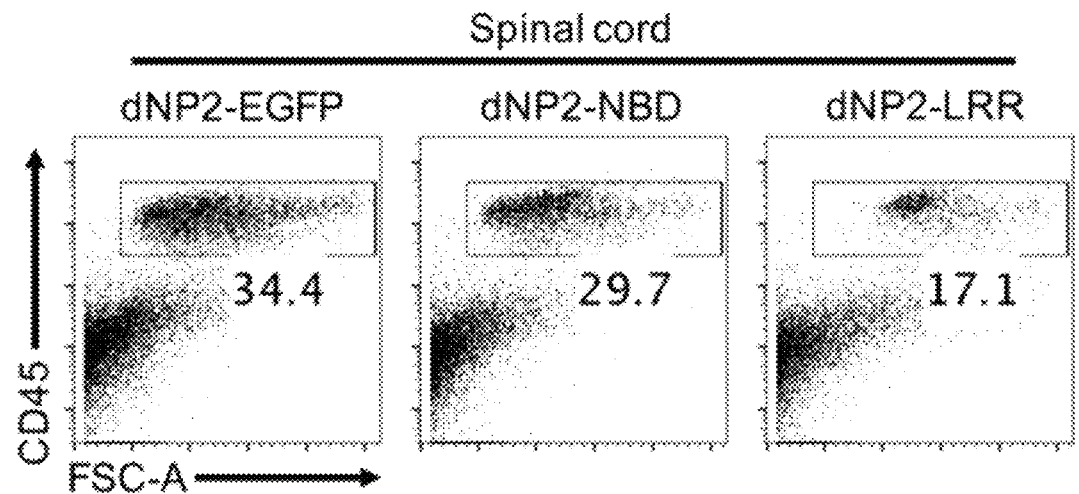
FIG. 21 shows a result of treating a prevention scheme model with a dNP2-LRR fusion protein of Example 1, a dNP2-NBD fusion protein of Comparative Example 1 or a dNP2-EGFP fusion protein of Comparative Example 2 and analyzing Percoll-isolated total cells from the spinal cord tissues of each group by flow cytometry.

FIG. 21 shows a result of treating the prevention scheme model the dNP2-LRR fusion protein of Example 1, the dNP2-NBD fusion protein of Comparative Example 1 or the dNP2-EGFP fusion protein of Comparative Example 2 and analyzing Percoll-isolated total cells from the spinal cord tissues of each group by flow cytometry.

Figure 22:
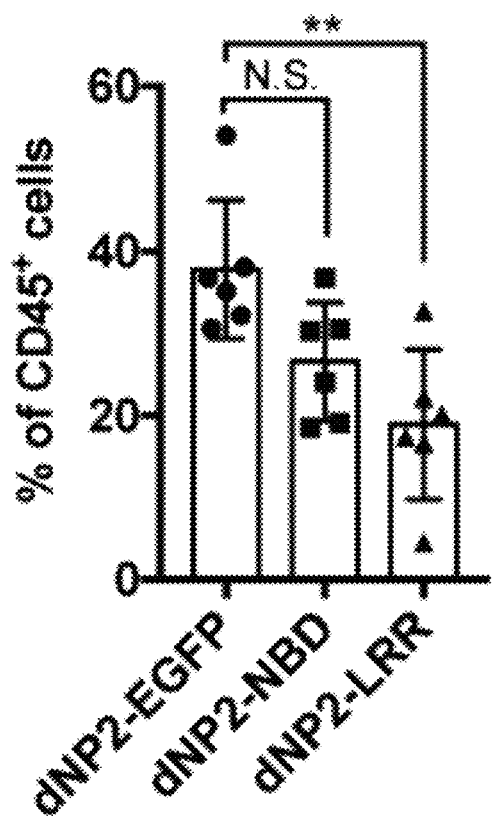
FIG. 22 and FIG. 23 show a result of treating a prevention scheme model with a dNP2-LRR fusion protein of Example 1, a dNP2-NBD fusion protein of Comparative Example 1 or a dNP2-EGFP fusion protein of Comparative Example 2 and analyzing the frequency (FIG. 22) and absolute number (FIG. 23) of CD45+ cells in Percoll-isolated total cells from the spinal cord tissues of each group by flow cytometry. n=11 and error bars indicate S.D. *P<0.05, P<0.01 and *P<0.001. N.S.: not significant.
Figure 23:
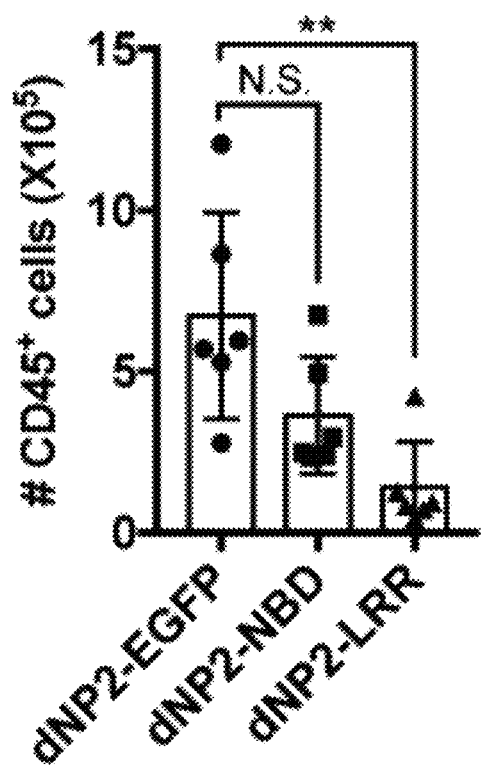

FIG. 22 and FIG. 23 show a result of treating the prevention scheme model with the dNP2-LRR fusion protein of Example 1, the dNP2-NBD fusion protein of Comparative Example 1 or the dNP2-EGFP fusion protein of Comparative Example 2 and analyzing the frequency (FIG. 22) and absolute number (FIG. 23) of CD45$^+$ cells in Percoll-isolated total cells from the spinal cord tissues of each group by flow cytometry. n=11 and error bars indicate S.D. *P<0.05, P<0.01 and *P<0.001. N.S.: not significant.

From FIGS. 21-23, it was confirmed that the number of CD45$^+$ immune cells was significantly reduced in the prevention scheme model treated with the dNP2-LRR fusion protein of Example 1.

Figure 24:
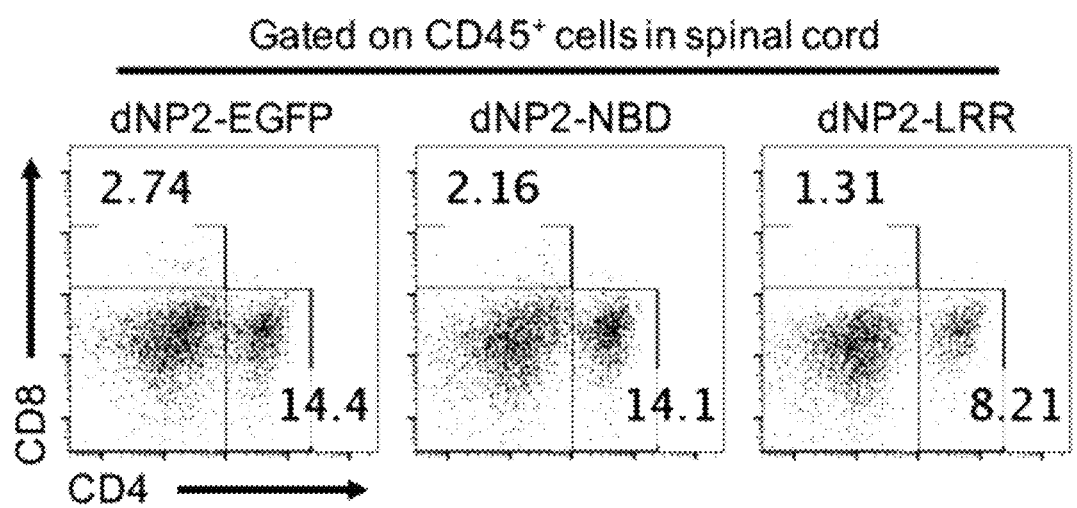
FIG. 24 shows a result of treating a prevention scheme model with a dNP2-LRR fusion protein of Example 1, a dNP2-NBD fusion protein of Comparative Example 1 or a dNP2-EGFP fusion protein of Comparative Example 2 and analyzing the spinal cord tissues obtained from each group by flow cytometry.

FIG. 24 shows a result of treating the prevention scheme model with the dNP2-LRR fusion protein of Example 1, the dNP2-NBD fusion protein of Comparative Example 1 or the dNP2-EGFP fusion protein of Comparative Example 2 and analyzing the spinal cord tissues obtained from each group by flow cytometry.

Figure 25:
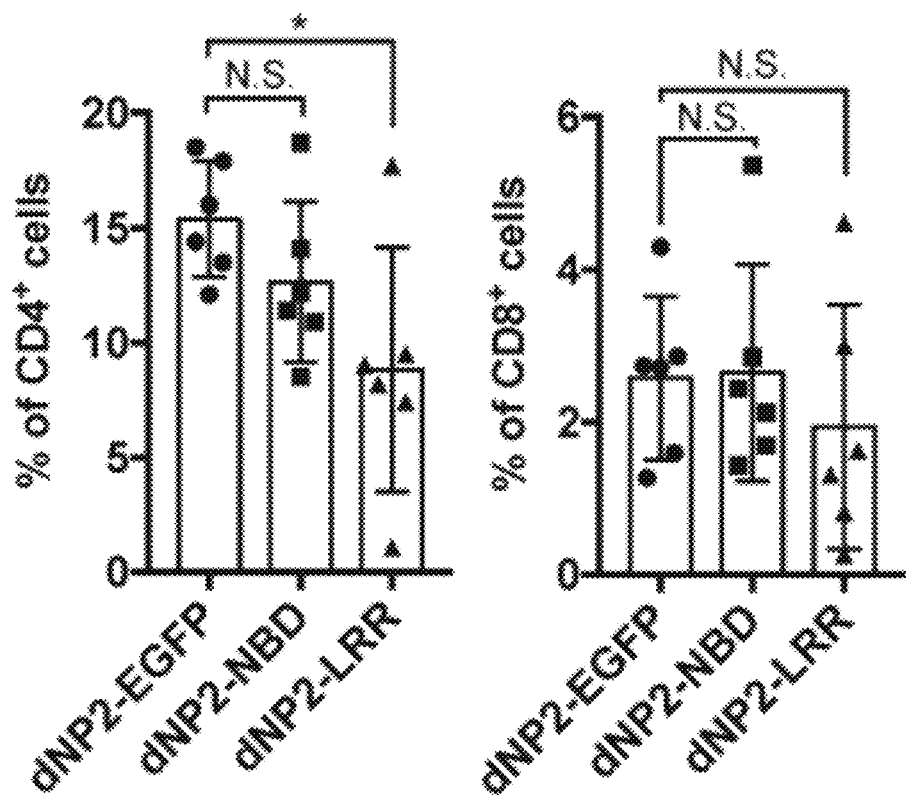
FIG. 25 and FIG. 26 show a result of treating a prevention scheme model with a dNP2-LRR fusion protein of Example 1, a dNP2-NBD fusion protein of Comparative Example 1 or a dNP2-EGFP fusion protein of Comparative Example 2 and analyzing the frequency (FIG. 25) and absolute number (FIG. 26) of CD4$^+$ and CD8$^+$ cells in the spinal cord tissues obtained from each group by flow cytometry. n=11 and error bars indicate S.D. *P<0.05, P<0.01 and *P<0.001. N.S.: not significant.
Figure 26:
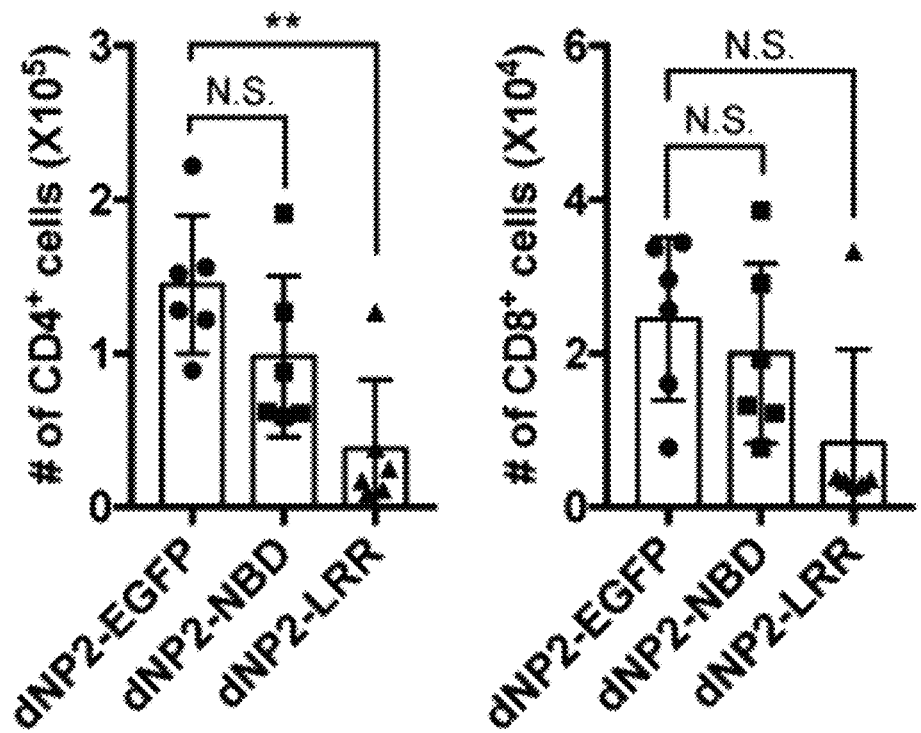

FIG. 25 and FIG. 26 show a result of treating the prevention scheme model with the dNP2-LRR fusion protein of Example 1, the dNP2-NBD fusion protein of Comparative Example 1 or the dNP2-EGFP fusion protein of Comparative Example 2 and analyzing the frequency (FIG. 25) and absolute number (FIG. 26) of CD4$^+$ and CD8$^+$ cells in the spinal cord tissues obtained from each group by flow cytometry. n=11 and error bars indicate S.D. *P<0.05, P<0.01 and *P<0.001. N.S.: not significant.

From FIGS. 24-26, it can be seen that the proportion and absolute number of CD4$^+$ T cells were significantly decreased in the prevention scheme model treated with the dNP2-LRR fusion protein of Example 1. In contrast, no significant change was observed in the prevention scheme model treated with the dNP2-NBD fusion protein of Comparative Example 1.

Figure 27:
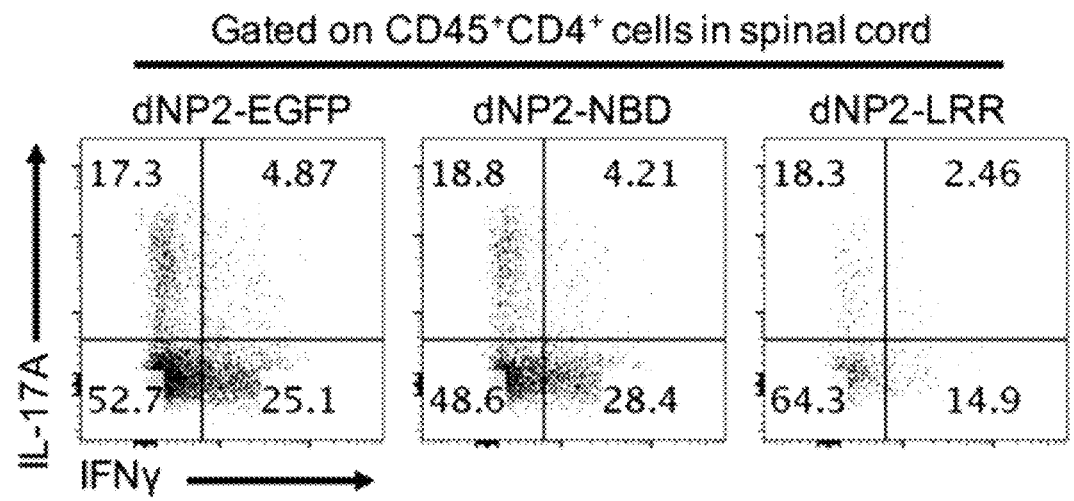
FIG. 27 shows a result of treating a prevention scheme model with a dNP2-LRR fusion protein of Example 1, a dNP2-NBD fusion protein of Comparative Example 1 or a dNP2-EGFP fusion protein of Comparative Example 2 and analyzing the spinal cord tissues obtained from each group by flow cytometry.

FIG. 27 shows a result of treating the prevention scheme model with the dNP2-LRR fusion protein of Example 1, the dNP2-NBD fusion protein of Comparative Example 1 or the dNP2-EGFP fusion protein of Comparative Example 2 and analyzing the spinal cord tissues obtained from each group by flow cytometry.

FIG. 28 shows a result of treating the prevention scheme model with the dNP2-LRR fusion protein of Example 1, the dNP2-NBD fusion protein of Comparative Example 1 or the dNP2-EGFP fusion protein of Comparative Example 2 and analyzing the frequency of IFNγ$^+$, IFNγ$^+$IL-17A$^+$, IL-17A$^+$ and Foxp3$^+$ CD4 T cells in the spinal cord tissues obtained from each group by flow cytometry. n=11 and error bars indicate S.D. *P<0.05, P<0.01 and *P<0.001. N.S.: not significant.

As seen from FIG. 27 and FIG. 28, the proportion of IFNγ-producing cells was decreased significantly in CD4$^+$ T cells for the prevention scheme model treated with the dNP2-LRR fusion protein of Example 1. This implies a possible in vivo mechanism of inhibition of IFNγ production by the dNP2-LRR fusion protein of Example 1. Through this, it can be seen that neurological autoimmune diseases including experimental autoimmune encephalitis (EAE) can be controlled with the administration of the LRR domain together with the NLRX1 protein, whereas the NBD domain does not exhibit preventive or therapeutic effect for experimental autoimmune encephalitis (EAE) at all.

Test Example 9 Effect of Treating Neurological Autoimmune Disease of dNP2-LRR Fusion Protein of Example 1-1

1) Animal Model

All mice (C57BL/6J) were maintained in a pathogen-free facility at Hanyang University. The animal experiment protocol used in this study was approved by the Animal Experimentation Ethics Committee of Hanyang University, and all experiments were performed according to the guidelines of the Institutional Animal Care and Use Committee of Hanyang University.

10-week-old female C57BL/6 mice were purchased from Orient Bio. An experimental autoimmune encephalitis (EAE) animal model was induced by immunization with MOG$_{35-55}$ antigen (Hooke Labs, Lawrence, Mass., USA) and 100 ng injection of pertussis toxin (PT).

Figure 16B:
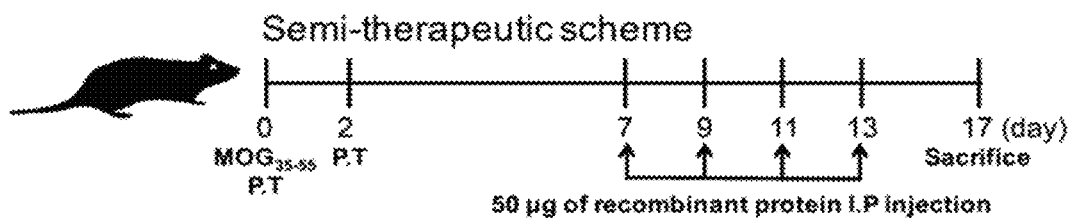
FIG. 16B describes an experimental scheme for analyzing the therapeutic or semi-therapeutic effect of Test Example 9 and Test Example 10 for an EAE animal model of a neurological autoimmune disease.

For analysis of therapeutic effect, a therapeutic scheme model was designed by intraperitoneally administering 100 μg of a fusion protein every day, from day 16 until the day of sacrifice (FIG. 16B).

A semi-therapeutic scheme model for analyzing semi-therapeutic effect was designed as follows. Experimental autoimmune encephalitis (EAE) was induced by subcutaneous injection of 100 μg of MOG$_{35-55}$ antigen (GenScript, Nanjing, China) in Freund's adjuvant emulsion (Chondrex, Redmond, Wash., USA). At day 0 and day 2 after immunization, 200 ng of pertussis toxin (PT) (List Biological Laboratories Inc., Campbell, Calif., USA) was injected intraperitoneally. The fusion protein (50 μg) was injected intraperitoneally on alternate days, from day 7 until day 13 (FIG. 16B).

For the therapeutic scheme model and the semi-therapeutic scheme model, the animals were scored every day for the signs of clinical disease (Stromnes I M, Goverman J M. Active induction of experimental allergic encephalomyelitis. *Nat Protoc.* 2006; 1: 1810-9). Spinal cord tissues were harvested from the animal model and analyzed by histology, flow cytometry and real-time polymerase chain reaction (RT-PCR).

As the fusion protein, the dNP2-LRR fusion protein of Example 1 and the dNP2-EGFP fusion protein of Comparative Example 2 were used.

2) Conclusion

Based on the effect of the dNP2-LRR fusion protein of Example 1 for the prevention scheme model, its therapeutic effect on immunized mouse was investigated. After treating the semi-therapeutic animal model with the dNP2-LRR fusion protein of Example 1 or the dNP2-EGFP fusion protein of Comparative Example 2, the animals were scored every day for the signs of clinical disease (Stromnes I M, Goverman J M. Active induction of experimental allergic encephalomyelitis. *Nat Protoc.* 2006; 1: 1810-9). Spinal cord tissues were harvested from the animal model and analyzed by histology. The result is shown in FIGS. 29 and 30.

FIG. 29 shows a result of treating the semi-therapeutic animal model with the dNP2-LRR fusion protein of Example 1 or the dNP2-EGFP fusion protein of Comparative Example 2 and analyzing clinical scores every day. n=5 and error bars indicate S.D. *P<0.05, P<0.01 and *P<0.001. N.S.: not significant.

FIG. 30 shows a result of treating the semi-therapeutic animal model with the dNP2-LRR fusion protein of Example 1 or the dNP2-EGFP fusion protein of Comparative Example 2 and analyzing disease incidence rate.

From FIG. 29 and FIG. 30, it can be seen that the semi-therapeutic animal model treated with the dNP2-EGFP fusion protein of Comparative Example 2 showed the onset of disease on day 8, which progressed rapidly by day 11, sustaining an average clinical score of 1.5 or higher until day 17. In contrast, the semi-therapeutic animal model treated with the dNP2-LRR fusion protein of Example 1 showed the onset of experimental autoimmune encephalitis (EAE) in only 1 out of 5 mice by the end of the experiment on day 17. Through this, it was confirmed that the dNP2-LRR fusion protein of Example 1 can significantly inhibit the onset of neurological autoimmune diseases including experimental autoimmune encephalitis (EAE).

Spinal cord tissues were isolated from each group prepared by treating the semi-therapeutic animal model with the dNP2-LRR fusion protein of Example 1 or the dNP2-EGFP fusion protein of Comparative Example 2 and analyzed by histology. Specific procedures are as follows. The spinal cord tissues isolated from each group were embedded in paraffin blocks and subsequently fixed with 4% paraformaldehyde. The paraffin blocks were sliced and stained with Luxol fast blue (LFB) and hematoxylin. The stained tissues were analyzed using a DMi8 microscope (Leica, Wetzlar, Germany). The result is shown in FIG. 31.

Figure 31:
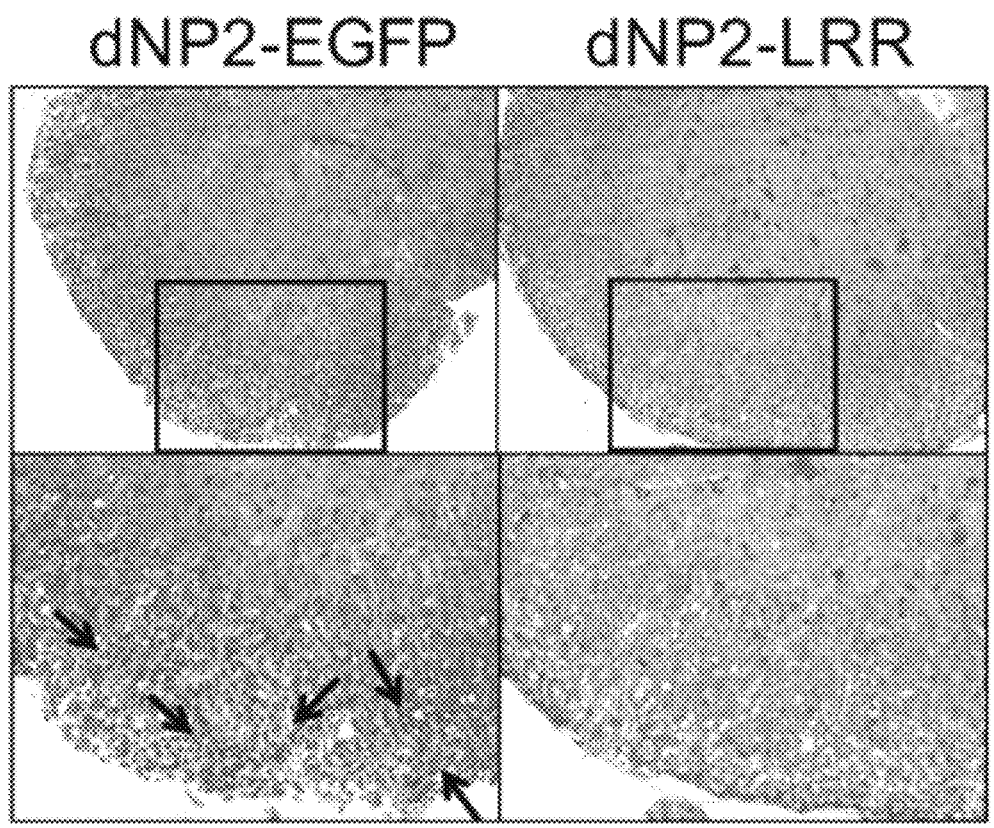
FIG. 31 shows a result of treating a semi-therapeutic animal model with a dNP2-LRR fusion protein of Example 1 or a dNP2-EGFP fusion protein of Comparative Example 2 and histologically analyzing the spinal cord tissues obtained from each group.

FIG. 31 shows a result of treating the semi-therapeutic animal model with the dNP2-LRR fusion protein of Example 1 or the dNP2-EGFP fusion protein of Comparative Example 2 and histologically analyzing the spinal cord tissues obtained from each group.

Figure 32:
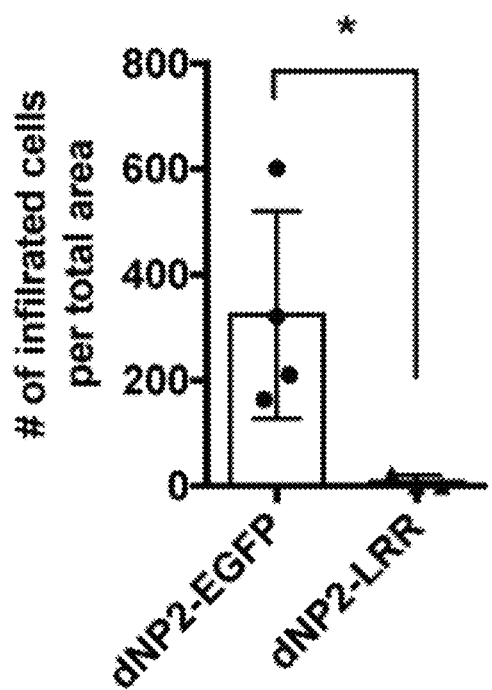
FIG. 32 shows a result of treating a semi-therapeutic animal model with a dNP2-LRR fusion protein of Example 1 or a dNP2-EGFP fusion protein of Comparative Example 2 and counting the number of infiltrated cells from the spinal cord tissues recovered from each group under a microscope. n=5 and error bars indicate S.D. *P<0.05, P<0.01 and *P<0.001. N.S.: not significant.

FIG. 32 shows a result of treating the semi-therapeutic animal model with the dNP2-LRR fusion protein of Example 1 or the dNP2-EGFP fusion protein of Comparative Example 2 and counting the number of infiltrated cells from the spinal cord tissues recovered from each group under a microscope. n=5 and error bars indicate S.D. *P<0.05, P<0.01 and *P<0.001. N.S.: not significant.

From FIG. 31 and FIG. 32, it can be seen that neuronal damage and cellular infiltration were significantly reduced for the dNP2-LRR fusion protein of Example 1. In contrast, for the semi-therapeutic animal model treated with the dNP2-EGFP fusion protein of Comparative Example 2, neuronal damage and cellular infiltration occurred at high levels.

Test Example 10 Effect of Treating Neurological Autoimmune Disease of dNP2-LRR Fusion Protein of Example 1-2

1) Animal Model

All mice (C57BL/6J) were maintained in a pathogen-free facility at Hanyang University. The animal experiment protocol used in this study was approved by the Animal Experimentation Ethics Committee of Hanyang University, and all experiments were performed according to the guidelines of the Institutional Animal Care and Use Committee of Hanyang University.

10-week-old female C57BL/6 mice were purchased from Orient Bio. An experimental autoimmune encephalitis (EAE) animal model was induced by immunization with $MOG_{35-55}$ antigen (Hooke Labs, Lawrence, Mass., USA) and 100 ng injection of pertussis toxin (PT).

For analysis of semi-therapeutic effect, a semi-therapeutic scheme model was designed as follows. Experimental autoimmune encephalitis (EAE) was induced by subcutaneous injection of 100 µg of $MOG_{35-55}$ antigen (GenScript, Nanjing, China) in Freund's adjuvant emulsion (Chondrex, Redmond, Wash., USA). At day 0 and day 2 after immunization, 200 ng of pertussis toxin (PT) (List Biological Laboratories Inc., Campbell, Calif., USA) was injected intraperitoneally. The fusion protein (50 µg) was injected intraperitoneally on alternate days, from day 7 until day 13 (FIG. 16B).

As the fusion protein, the dNP2-LRR fusion protein of Example 1 or the dNP2-EGFP fusion protein of Comparative Example 2 was used for each group.

2) Flow Cytometry

After recovering spinal cord tissues from each group, lymphocytes were isolated from the spinal cord tissues by Percoll (GE Healthcare, IL, USA, USA) density-gradient centrifugation. Cells were stained with fluorochrome-conjugated monoclonal antibodies: mouse anti-CD45-Pacific blue (1:1000 diluted), anti-CD4-PE-Cy7 (1:1000 diluted), anti-CD8-PerCP-Cy5.5 (1:1000 diluted), anti-CD25-PE (1:1000 diluted), anti-CD69-FITC (1:1000 diluted), anti-CD44-APC-Cy7 (1:1000 diluted), anti-CXCR3-FITC (1:200 diluted), anti-CCR6-PE-Cy7 (1:200 diluted, BioLegend, San Diego, Calif., USA), anti-IFNγ-FITC (1:100 diluted), anti-IL-17A-PE (1:200 diluted), anti-FOXP3-APC (1:400 diluted, eBioscience, San Diego, Calif., USA) and anti-T-bet-PE (3 µL per sample, BD, Franklin Lakes, N.J., USA). Intracellular cytokine staining was performed using an Intracellular Fixation and Permeabilization kit (eBioscience, San Diego, Calif., USA) according to the manufacturer's instructions. The samples were run on a BD Canto II cytometer (BD Biosciences, San Jose, Calif., USA) and the results were analyzed using the FlowJo software version 10.1 (BD, Franklin Lakes, N.J., USA).

3) Conclusion

Figure 33:
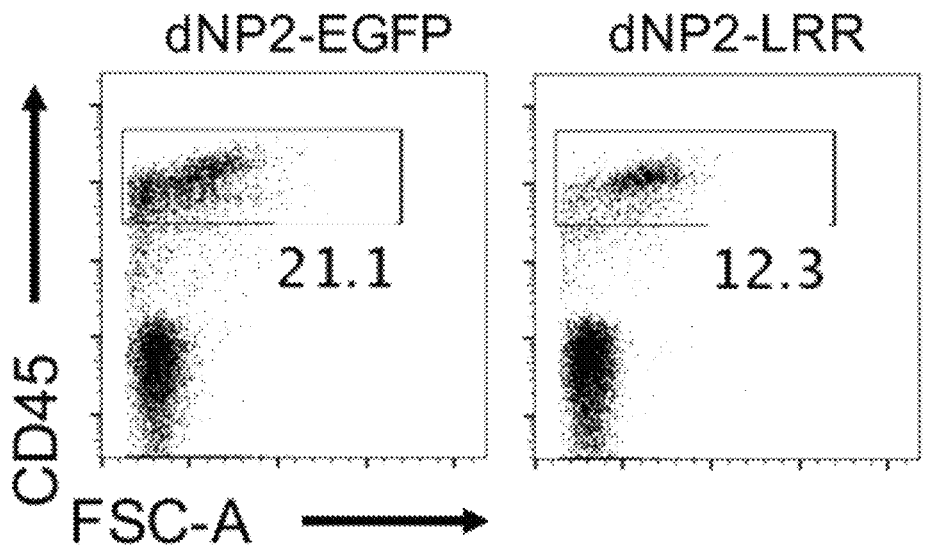
FIG. 33 shows a result of treating a semi-therapeutic animal model with a dNP2-LRR fusion protein of Example 1 or a dNP2-EGFP fusion protein of Comparative Example 2 and analyzing Percoll-isolated total cells from the spinal cord tissues of each group by flow cytometry.

FIG. 33 shows a result of treating the semi-therapeutic animal model with the dNP2-LRR fusion protein of Example 1 or the dNP2-EGFP fusion protein of Comparative Example 2 and analyzing Percoll-isolated total cells from the spinal cord tissues of each group by flow cytometry.

Figure 34:
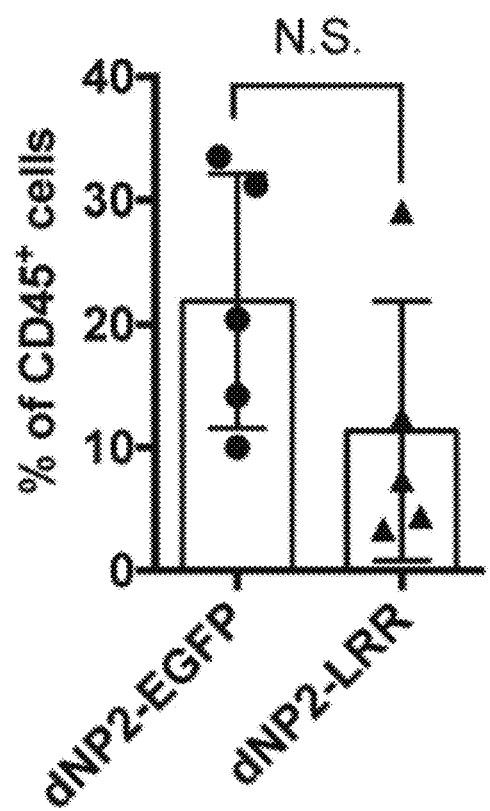
FIG. 34 and FIG. 35 show a result of treating a semi-therapeutic animal model with a dNP2-LRR fusion protein of Example 1 or a dNP2-EGFP fusion protein of Comparative Example 2 and analyzing the frequency (FIG. 34) and absolute number (FIG. 35) of CD45$^+$ cells in Percoll-isolated total cells from the spinal cord tissues of each group by flow cytometry. n=5 and error bars indicate S.D. *P<0.05, P<0.01 and *P<0.001. N.S.: not significant.
Figure 35:
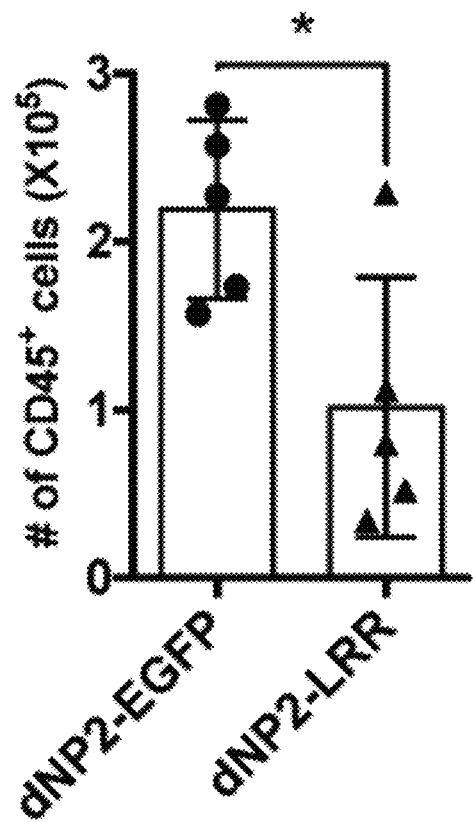

FIG. 34 and FIG. 35 show a result of treating the semi-therapeutic animal model with the dNP2-LRR fusion protein of Example 1 or the dNP2-EGFP fusion protein of Comparative Example 2 and analyzing the frequency (FIG. 34) and absolute number (FIG. 35) of CD45$^+$ cells in Percoll-isolated total cells from the spinal cord tissues of each group by flow cytometry. n=5 and error bars indicate S.D. *P<0.05, P<0.01 and *P<0.001. N.S.: not significant.

As seen from FIG. 33-35, the proportion (%) and absolute number of CD45$^+$ cells in the isolated spinal cord cells from each group were compared. Specifically, the proportion (%) and absolute number of CD45$^+$ cells were decreased significantly in the semi-therapeutic animal mode treated with the dNP2-LRR fusion protein of Example 1 as compared to the dNP2-EGFP fusion protein of Comparative Example 2.

Figure 36:
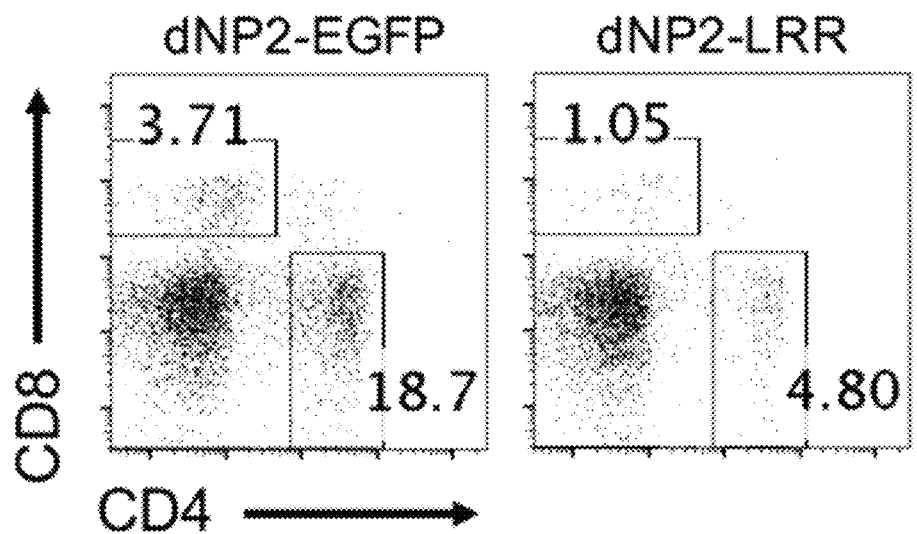
FIG. 36 shows a result of treating a semi-therapeutic animal model with a dNP2-LRR fusion protein of Example 1 or a dNP2-EGFP fusion protein of Comparative Example 2 and analyzing the spinal cord tissues recovered from each group by flow cytometry.

FIG. 36 shows a result of treating the semi-therapeutic animal model with the dNP2-LRR fusion protein of Example 1 or the dNP2-EGFP fusion protein of Comparative Example 2 and analyzing the spinal cord tissues recovered from each group by flow cytometry.

Figure 37:
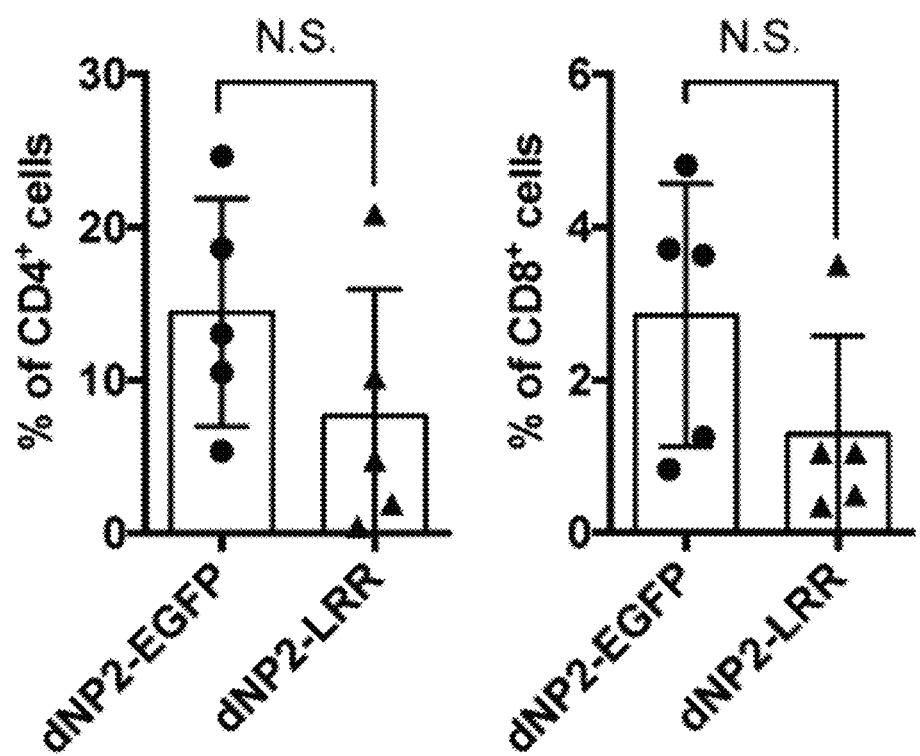
FIG. 37 and FIG. 38 show a result of treating a semi-therapeutic animal model with a dNP2-LRR fusion protein of Example 1 or a dNP2-EGFP fusion protein of Comparative Example 2 and analyzing the frequency (FIG. 37) and absolute number (FIG. 38) of CD4$^+$ or CD8$^+$ cells from the spinal cord tissues of each group by flow cytometry. n=5 and error bars indicate S.D. *P<0.05, P<0.01 and *P<0.001. N.S.: not significant.
Figure 38:
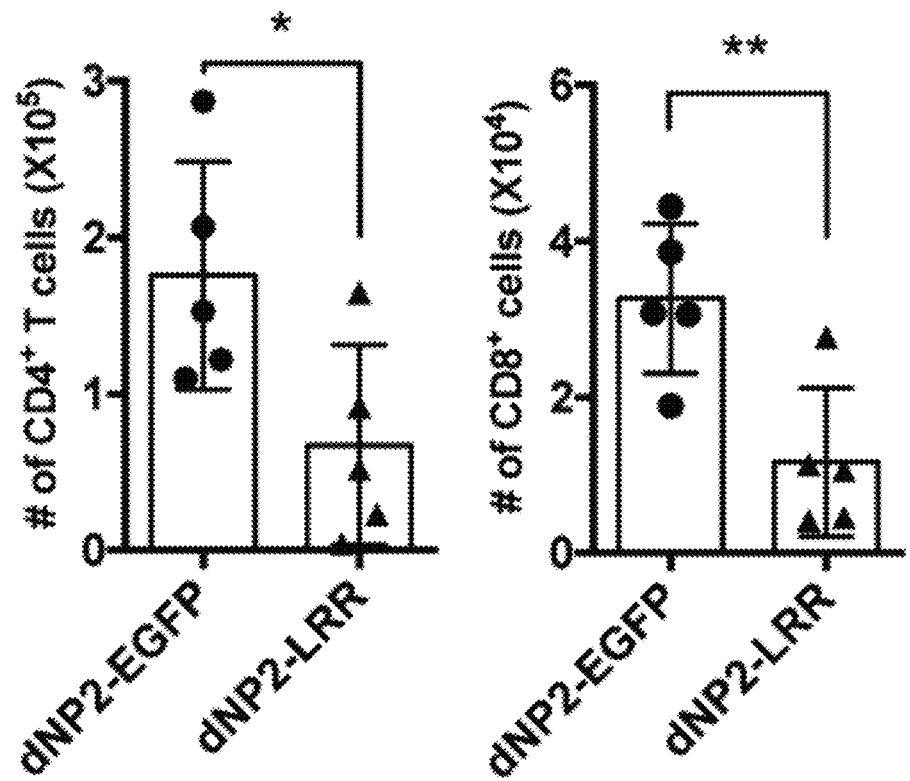

FIG. 37 and FIG. 38 show a result of treating the semi-therapeutic animal model with the dNP2-LRR fusion protein of Example 1 or the dNP2-EGFP fusion protein of Comparative Example 2 and analyzing the frequency (FIG. 37) and absolute number (FIG. 38) of CD4$^+$ or CD8$^+$ cells from the spinal cord tissues of each group by flow cytometry. n=5 and error bars indicate S.D. *P<0.05, P<0.01 and *P<0.001. N.S.: not significant.

From FIGS. 36-38, it can be seen that, whereas the number of infiltrating CD4$^+$ and CD8$^+$ T cells was increased in the semi-therapeutic animal model treated with the dNP2-EGFP fusion protein of Comparative Example 2, it was significantly decreased by the treatment with the dNP2-LRR fusion protein of Example 1.

Figure 39:
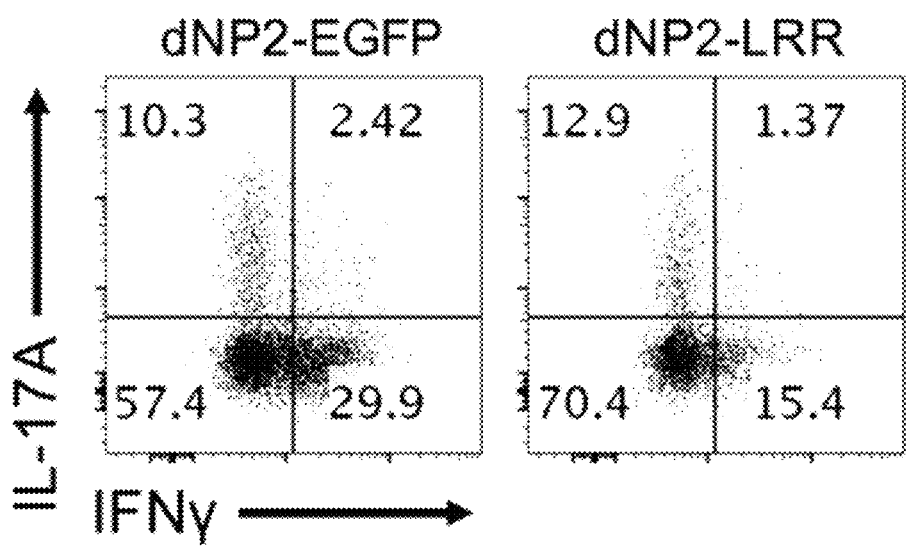
FIG. 39 shows a result of treating a semi-therapeutic animal model with a dNP2-LRR fusion protein of Example 1 or a dNP2-EGFP fusion protein of Comparative Example 2 and analyzing the spinal cord tissues recovered from each group by flow cytometry.

FIG. 39 shows a result of treating the semi-therapeutic animal model with the dNP2-LRR fusion protein of Example 1 or the dNP2-EGFP fusion protein of Comparative Example 2 and analyzing the spinal cord tissues recovered from each group by flow cytometry.

Figure 40:
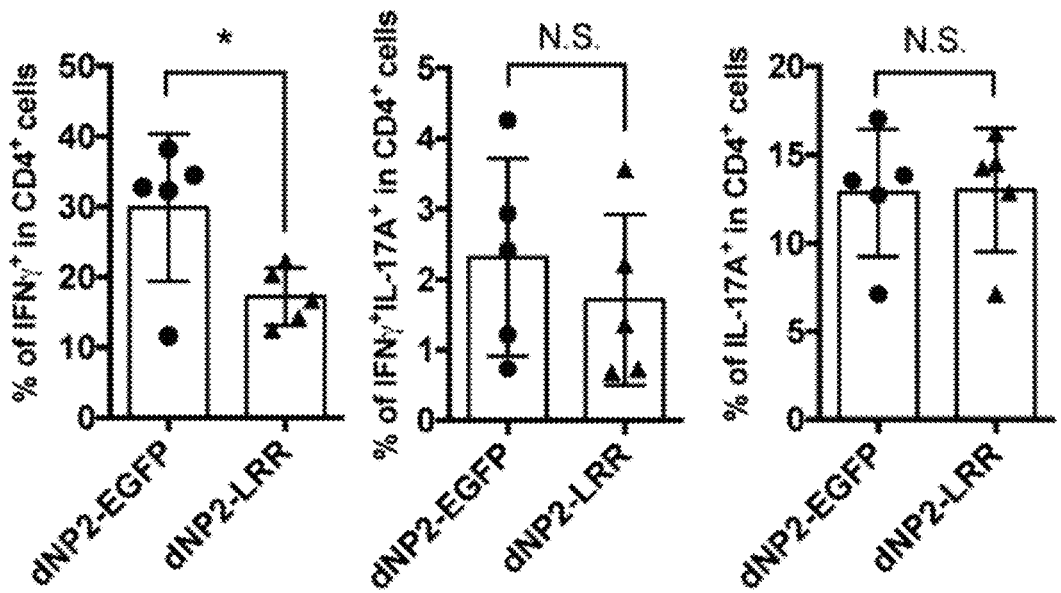
FIG. 40 and FIG. 41 show a result of treating a semi-therapeutic animal model with a dNP2-LRR fusion protein of Example 1 or a dNP2-EGFP fusion protein of Comparative Example 2 and analyzing the frequency (FIG. 40) and absolute number (FIG. 41) of γ- or IL-17A-producing cells from the spinal cord tissues of each group by flow cytometry. n=5 and error bars indicate S.D. *P<0.05, P<0.01 and *P<0.001. N.S.: not significant.
Figure 41:
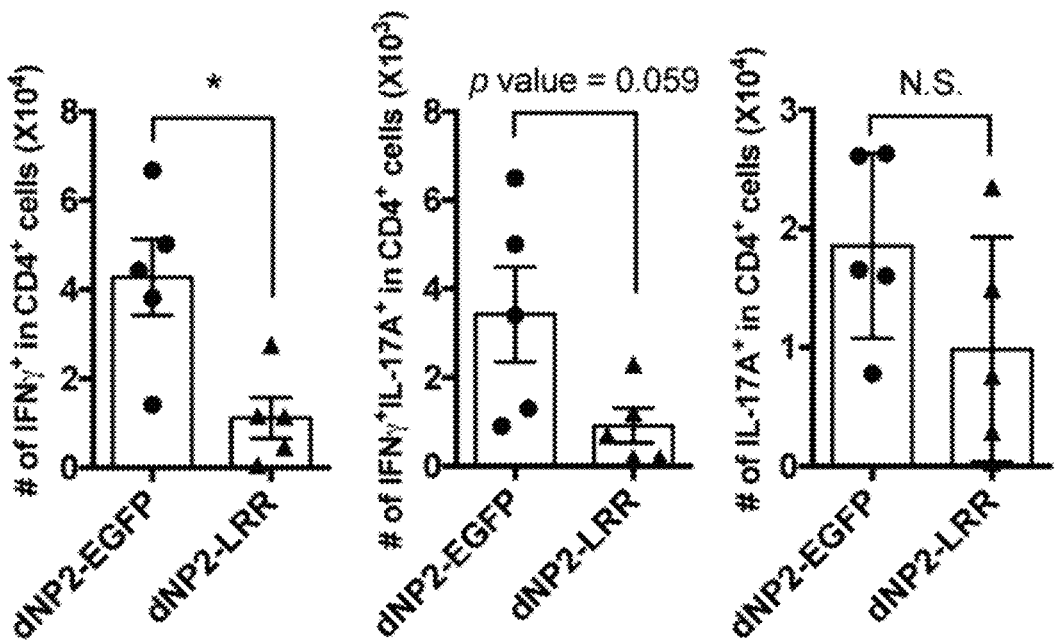

FIG. 40 and FIG. 41 show a result of treating the semi-therapeutic animal model with the dNP2-LRR fusion protein of Example 1 or the dNP2-EGFP fusion protein of Comparative Example 2 and analyzing the frequency (FIG. 40) and absolute number (FIG. 41) of γ- or IL-17A-producing cells from the spinal cord tissues of each group by flow cytometry. n=5 and error bars indicate S.D. *P<0.05, P<0.01 and *P<0.001. N.S.: not significant.

From FIGS. 39-41, it can be seen that the number of IFNγ- and IL-17A-producing cells was significantly decreased in infiltrating CD4$^+$ T cells for the semi-therapeutic animal mode treated with the dNP2-LRR fusion protein of Example 1. This result suggests that the dNP2-LRR fusion protein of Example 1 can prevent or treat neurological autoimmune diseases such as experimental autoimmune encephalitis (EAE) even after adaptive immune activation.

That is to say, it can be seen that the dNP2-LRR fusion protein of Example 1 can prevent or treat neurological autoimmune diseases such as experimental autoimmune encephalitis (EAE) by reducing IFNγ-producing ability or inducing Th1 cell infiltration, in the spinal cord.

Test Example 11 Evaluation of Inhibition of T Cell Activation and Regulation of Th1 Differentiation by dNP2-LRR Fusion Protein of Example 1

1) In-Vitro T Cell Activation

Naive CD4$^+$ T cells were isolated using a mouse naive CD4$^+$ T-cell isolation kit (Miltenyi Biotec, Bergisch Gladbach, Germany) according to the manufacturer's protocol. The purified naive CD4$^+$ T cells were activated with 1:5 of anti-CD3/CD28 Dynabeads (Gibco, Co Dublin, Ireland) and were incubated with a fusion protein at 37° C. for 1 day or 2 days. After the incubation, the supernatant was analyzed by ELISA and the cells were stained with fluorochrome-conjugated monoclonal antibodies: mouse anti-CD4, CD62L, CD25, CD69 and CD44 (BioLegend, San Diego, Calif., USA). The recovered sample was treated with BD Canto II cytometer (BD Biosciences, San Jose, Calif., USA) and the result was analyzed with FlowJo software version 10.1 (BD, Franklin Lakes, N.J., USA).

The dNP2-LRR (Example 1) or the dNP2-EGFP (Comparative Example 2) was used as the fusion protein, and PBS was used as a control group.

2) In-Vitro T Cell Differentiation

Naive CD4$^+$ T cells were isolated using a mouse naive CD4$^+$ T-cell isolation kit (Miltenyi Biotec, Bergisch Gladbach, Germany) according to the manufacturer's protocol. The purified naive CD4$^+$ T cells were cultured with 2 μg/mL plate-bound anti-CD3 (BD Biosciences, CA, USA, Jose Bios) and anti-CD28 (BD Biosciences, San Jose, Calif., USA) under Th1, Th17 or Treg-Skewing condition along with a fusion protein at various concentrations (0.2 μM, 0.5 μM, 1 μM). dNP2-LRR (Example 1) or dNP2-EGFP (Comparative Example 2) was used as the fusion protein, and PBS was used as a control group.

Th1 condition: treatment for 4 days with IL-2 (50 U/mL, Peprotech, Rocky Hill, N.J., USA), IL-12 (2 ng/mL, Peprotech, Rocky Hill, N.J., USA) and anti-IL-4 antibody (5 μg/mL, BD Biosciences, San Jose, Calif., USA).

Th17 condition: treatment for 4 days with IL-6 (30 ng/mL, BD Biosciences, San Jose, Calif., USA), TGFβ (0.5 ng/mL, R&D Systems, Minneapolis, Minn., USA), IL-23 (20 ng/mL, BD Biosciences, San Jose, Calif., USA), anti-IFNγ (5 μg/mL, BD Biosciences, San Jose, Calif., USA) and anti-IL-4 (5 μg/mL, BD Biosciences, San Jose, Calif., USA).

Treg-Skewing condition: treatment for 3 days with IL-2 (100 U/mL, Peprotech, Rocky Hill, N.J., USA) and TGFβ (5 ng/mL, R&D Systems, Minneapolis, Minn., USA).

After the incubation, the cells were stained with fluorochrome-conjugated monoclonal antibodies (mouse anti-CD4, IFNγ, IL-17A and FoxP3) (eBioscience, San Diego, Calif., USA). Intracellular cytokines were stained using an intracellular fixation and permeabilization kit (eBioscience, San Diego, Calif., USA) according to the manufacturer's instructions. The obtained sample was run on a BD Canto II cytometer (BD Biosciences, San Jose, Calif., USA) and the result was analyzed using the FlowJo software version 10.1 (BD, Franklin Lakes, N.J., USA).

3) Conclusion

Given the significant inhibition of experimental autoimmune encephalomyelitis (EAE) disease with reduced infiltration of T cells, especially IFNγ-producing CD4 T cells, in the spinal cord, it was hypothesized that the dNP2-NRR fusion protein of Example 1 according to the present disclosure is directly involved in T cell functions. To address this, MACS (magnetic activated cell sorting)-purified naive CD4 T cells (CD4⁺CD44⁻) stimulated with anti-CD3/28 antibody were used in this experiment. The result is as follows.

Figure 42:
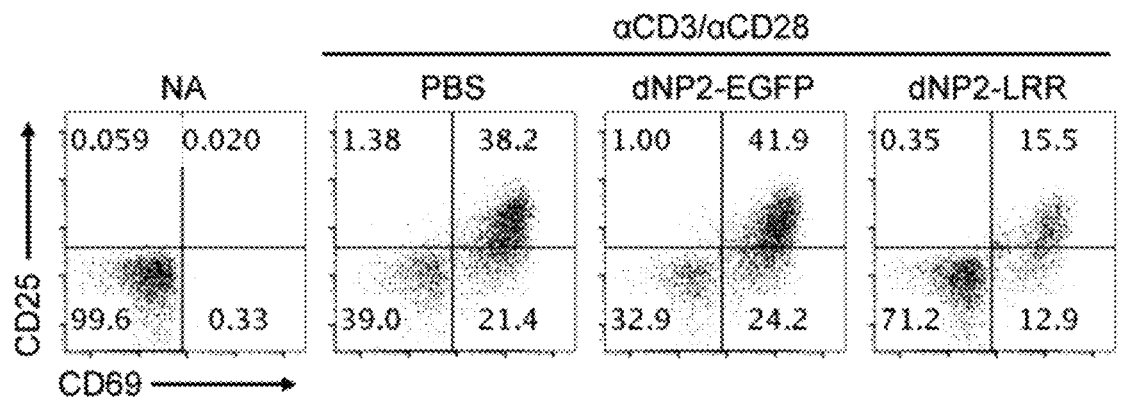
FIG. 42 shows a result of measuring the surface expression level of CD25 and CD69 in activated CD4 T cells by flow cytometry after incubation with 1 μM dNP2-LRR (Example 1) or dNP2-EGFP (Comparative Example 2) or PBS.

FIG. 42 shows a result of measuring the surface expression level of CD25 and CD69 in activated CD4 T cells by flow cytometry after incubation with 1 μM dNP2-LRR (Example 1) or dNP2-EGFP (Comparative Example 2) or PBS.

Figure 43:
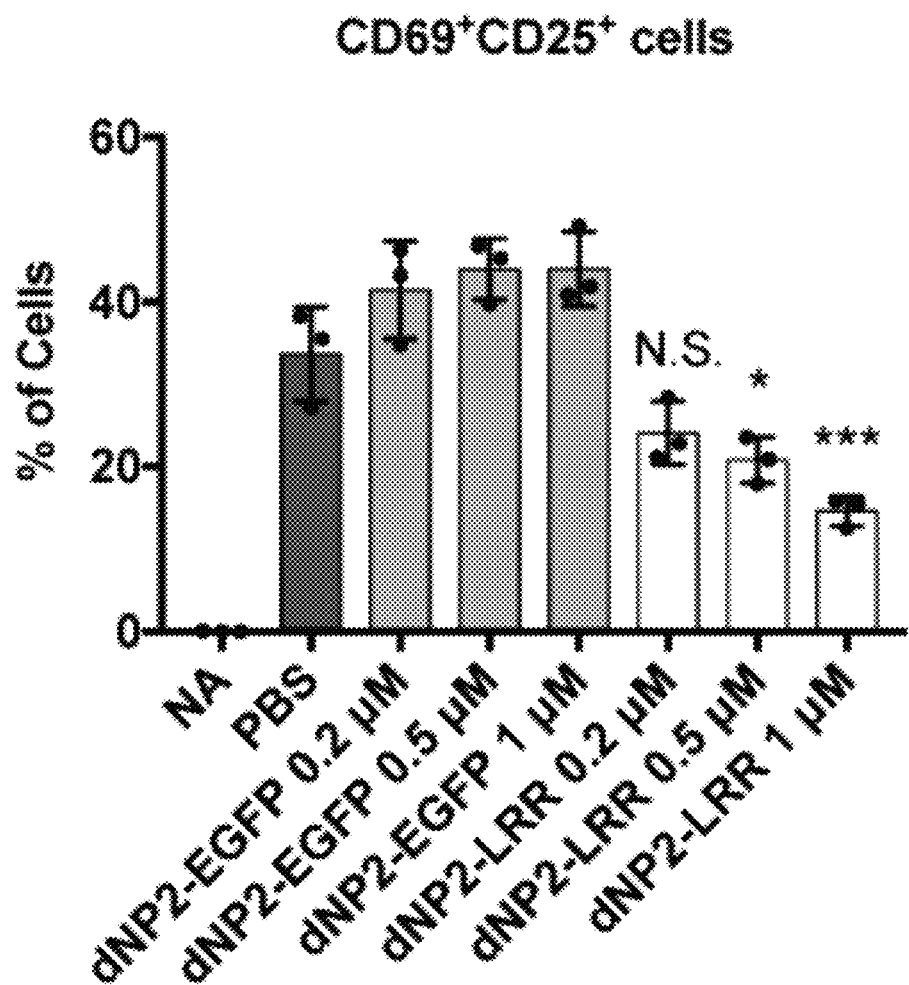
FIG. 43 shows a result of measuring the surface expression level of CD25 and CD69 in activated CD4 T cells after incubation with dNP2-LRR (Example 1) or dNP2-EGFP (Comparative Example 2) at various concentrations (0.2 μM, 0.5 μM, 1 μM) or PBS by measuring the frequency of CD69$^+$CD25$^+$ activated cells. n=3-6 and error bars indicate S.D. *P<0.05, P<0.01 and *P<0.001. N.A.: not activated, N.S.: not significant.
Figure 44:
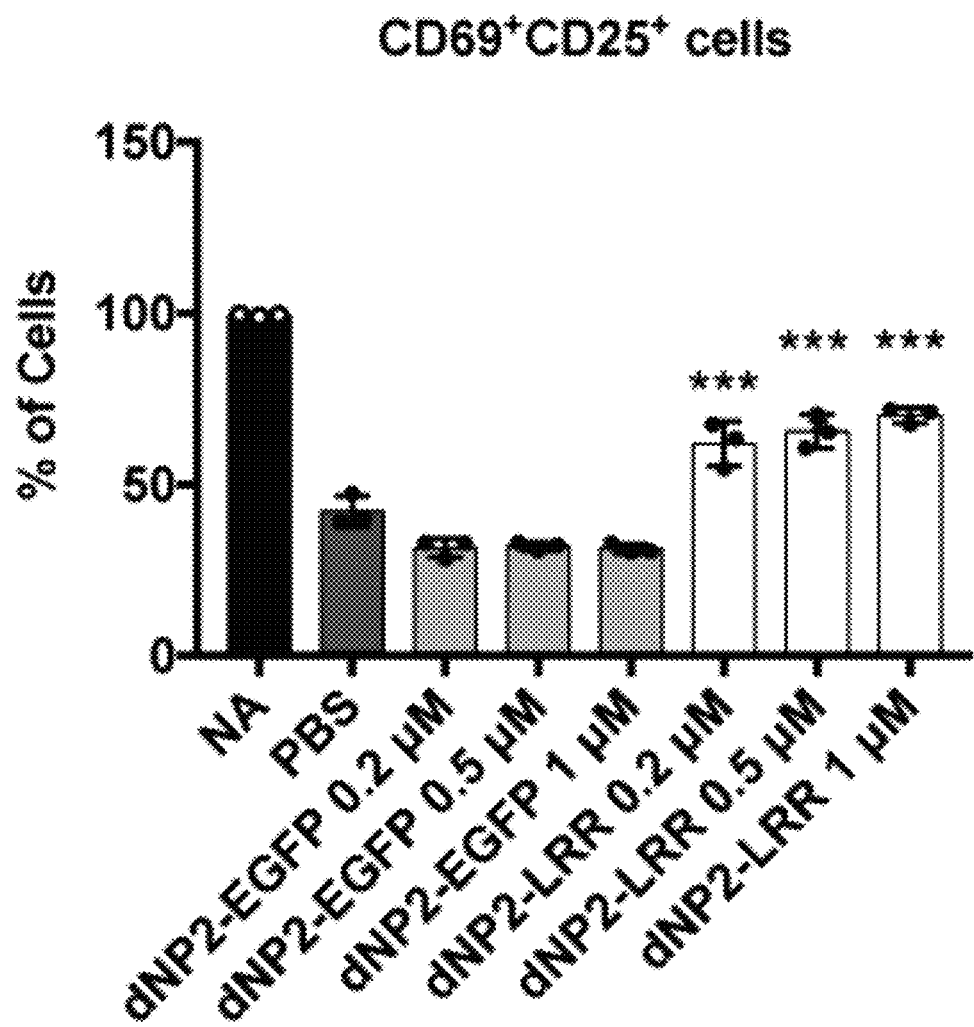
FIG. 44 shows a result of measuring the surface expression level of CD25 and CD69 in activated CD4 T cells after incubation with dNP2-LRR (Example 1) or dNP2-EGFP (Comparative Example 2) at various concentrations (0.2 μM, 0.5 μM, 1 μM) or PBS by measuring the frequency of CD69$^-$CD25$^-$ non-activated cells. n=3-6 and error bars indicate S.D. *P<0.05, P<0.01 and *P<0.001. N.A.: not activated, N.S.: not significant.

FIG. 43 shows a result of measuring the surface expression level of CD25 and CD69 in activated CD4 T cells after incubation with dNP2-LRR (Example 1) or dNP2-EGFP (Comparative Example 2) at various concentrations (0.2 μM, 0.5 μM, 1 μM) or PBS by measuring the frequency of CD69⁺CD25⁺ activated cells, and FIG. 44 shows a result of measuring the surface expression level of CD25 and CD69 in activated CD4 T cells after incubation with dNP2-LRR (Example 1) or dNP2-EGFP (Comparative Example 2) at various concentrations (0.2 μM, 0.5 μM, 1 μM) or PBS by measuring the frequency of CD69⁻CD25⁻ non-activated cells. n=3-6 and error bars indicate S.D. *P<0.05, P<0.01 and *P<0.001. N.A.: not activated, N.S.: not significant.

From FIGS. 42-44, it was confirmed that the surface expression level of T-cell activation markers including CD69 and CD25 was significantly reduced and the frequency of inactivated CD69⁻CD25⁻ populations was increased in the cells treated with the dNP2-LRR fusion protein of Example 1. In contrast, the group treated with the dNP2-EGFP fusion protein of Comparative Example 2 showed higher surface expression level of T-cell activation markers including CD69 and CD25 and lower frequency of inactivated CD69⁻CD25⁻ populations as compared to the control group treated with PBS only. Through this, it can be seen that the dNP2-LRR fusion protein of Example 1 inhibits T cell activation.

Figure 45:
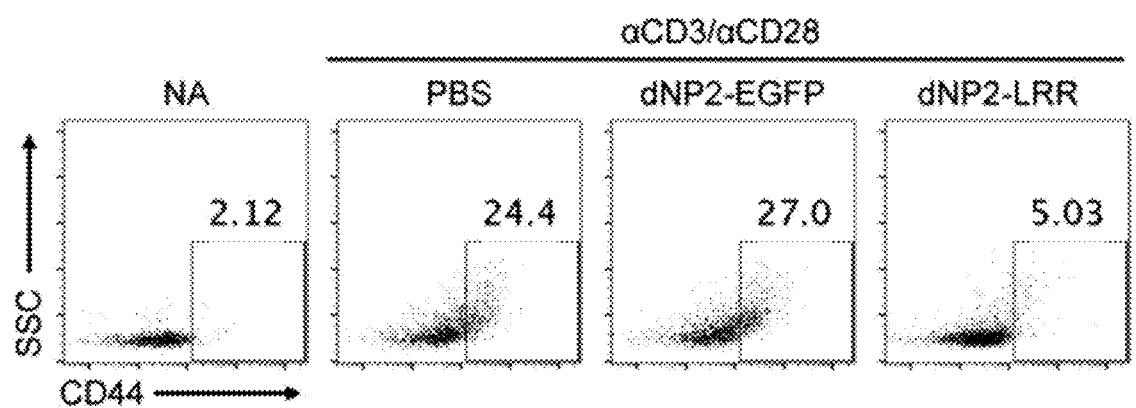
FIG. 45 shows a result of measuring the surface expression level of CD44 in activated CD4 T cells by flow cytometry after incubation with 1 μM dNP2-LRR (Example 1) or dNP2-EGFP (Comparative Example 2) or PBS.

FIG. 45 shows a result of measuring the surface expression level of CD44 in activated CD4 T cells by flow cytometry after incubation with 1 μM dNP2-LRR (Example 1) or dNP2-EGFP (Comparative Example 2) or PBS.

Figure 46:
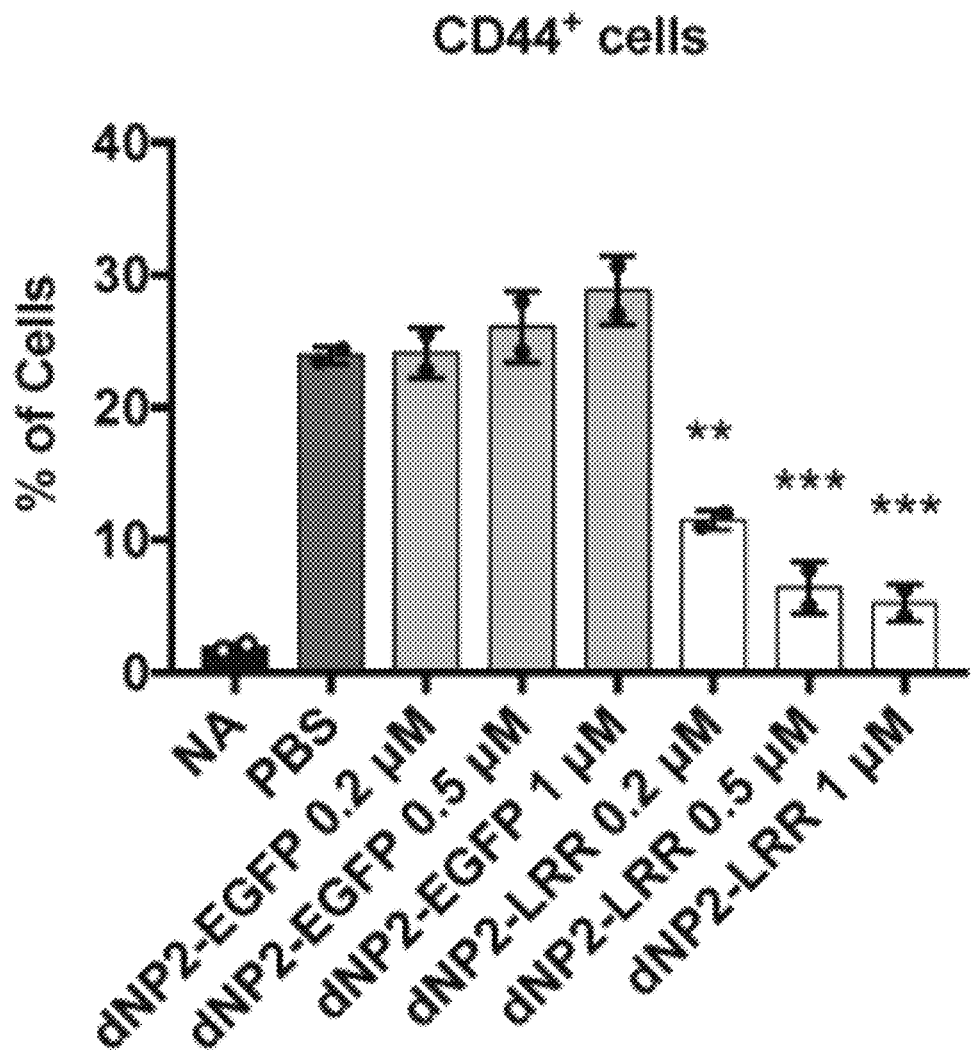
FIG. 46 shows a result of measuring the surface expression level of CD44 in activated CD4 T cells after incubation with dNP2-LRR (Example 1) or dNP2-EGFP (Comparative Example 2) at various concentrations (0.2 μM, 0.5 μM, 1 μM) or PBS by measuring the frequency of CD44+ activated cells. n=3-6 and error bars indicate S.D. *P<0.05, P<0.01 and *P<0.001. N.A.: not activated, N.S.: not significant.
Figure 47:
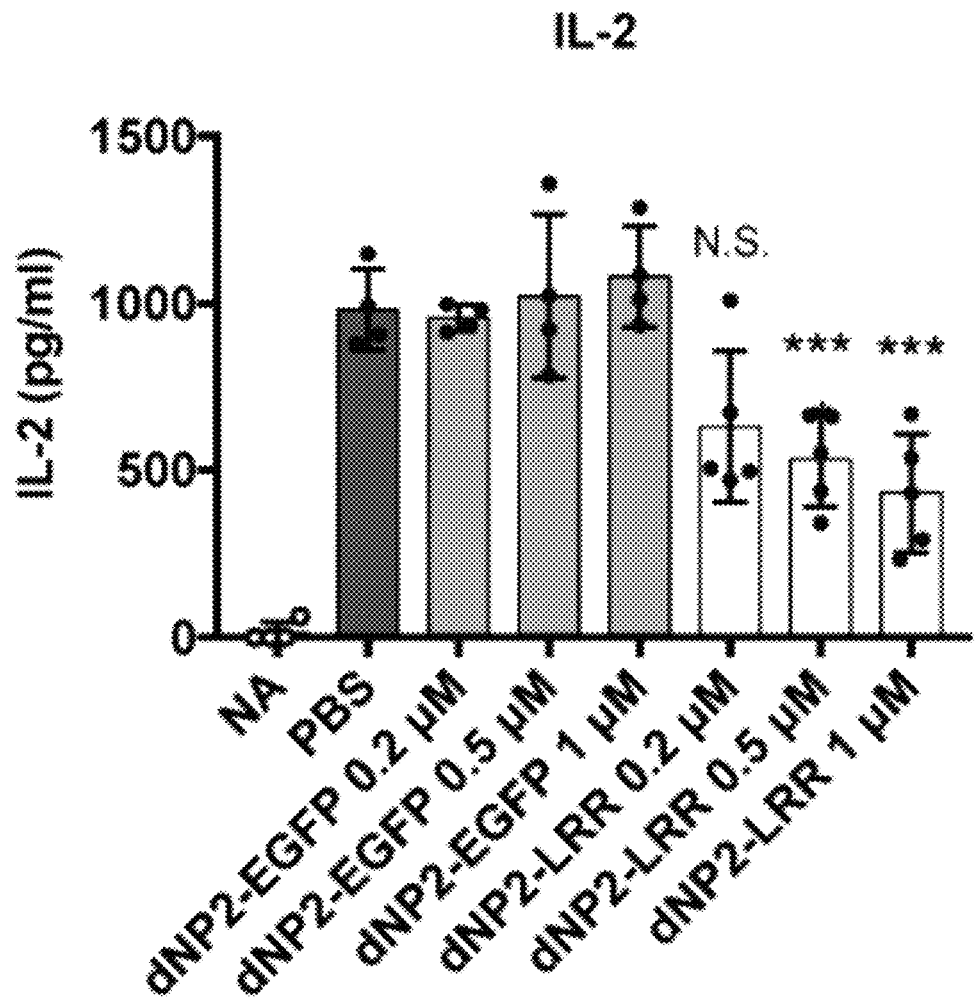
FIG. 47 shows a result of measuring IL-2 production in a culture supernatant by ELISA after incubation of activated CD4 T cells with dNP2-LRR (Example 1) or dNP2-EGFP (Comparative Example 2) at various concentrations (0.2 μM, 0.5 μM, 1 μM) or PBS. n=3-6 and error bars indicate S.D. *P<0.05, P<0.01 and *P<0.001. N.A.: not activated, N.S.: not significant.

FIG. 46 shows a result of measuring the surface expression level of CD44 in activated CD4 T cells after incubation with dNP2-LRR (Example 1) or dNP2-EGFP (Comparative Example 2) at various concentrations (0.2 μM, 0.5 μM, 1 μM) or PBS by measuring the frequency of CD44⁺ activated cells, and FIG. 47 shows a result of measuring IL-2 production in a culture supernatant by ELISA after incubation of activated CD4 T cells with dNP2-LRR (Example 1) or dNP2-EGFP (Comparative Example 2) at various concentrations (0.2 μM, 0.5 μM, 1 μM) or PBS. n=3-6 and error bars indicate S.D. *P<0.05, P<0.01 and *P<0.001. N.A.: not activated, N.S.: not significant.

From FIG. 45 and FIG. 46, it was confirmed that the expression of CD44 in T cells was decreased by treatment with the dNP2-LRR fusion protein of Example 1.

From FIG. 47, it was confirmed that the expression of IL-2 in the culture supernatant was significantly decreased by treatment with the dNP2-LRR fusion protein of Example 1. Through this, it can be seen that the dNP2-LRR fusion protein of Example 1 directly inhibits T cell activation and cytokine production.

The effect of the dNP2-LRR fusion protein of Example 1 on the differentiation of effector T cells such as Th1, Th17 and Treg cells, which play an important role in experimental autoimmune encephalomyelitis (EAE) disease, was examined. Specifically, naive CD4⁺ T cells were treated with the fusion protein at various concentrations and differentiated into Th1, Th17 or Treg cells in vitro.

Figure 48:
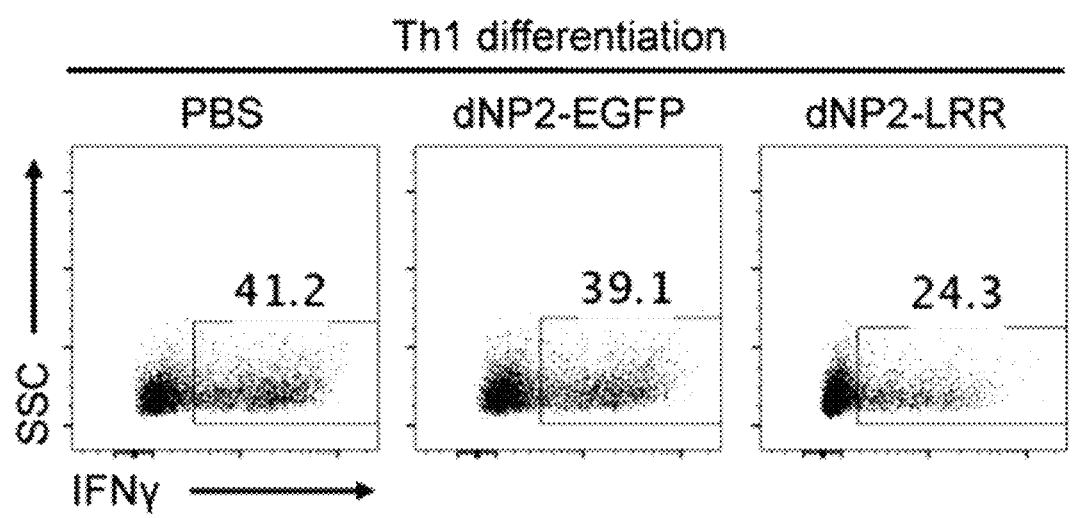
FIG. 48 shows a result of differentiating naive CD4+ T cells under Th1 condition with dNP2-LRR (Example 1) or dNP2-EGFP (Comparative Example 2) at various concentrations (0.2 μM, 0.5 μM, 1 μM) or PBS and analyzing the result by flow cytometry.

FIG. 48 shows a result of differentiating naive CD4⁺ T cells under Th1 condition with dNP2-LRR (Example 1) or dNP2-EGFP (Comparative Example 2) at various concentrations (0.2 μM, 0.5 μM, 1 μM) or PBS and analyzing the result by flow cytometry.

Figure 49:
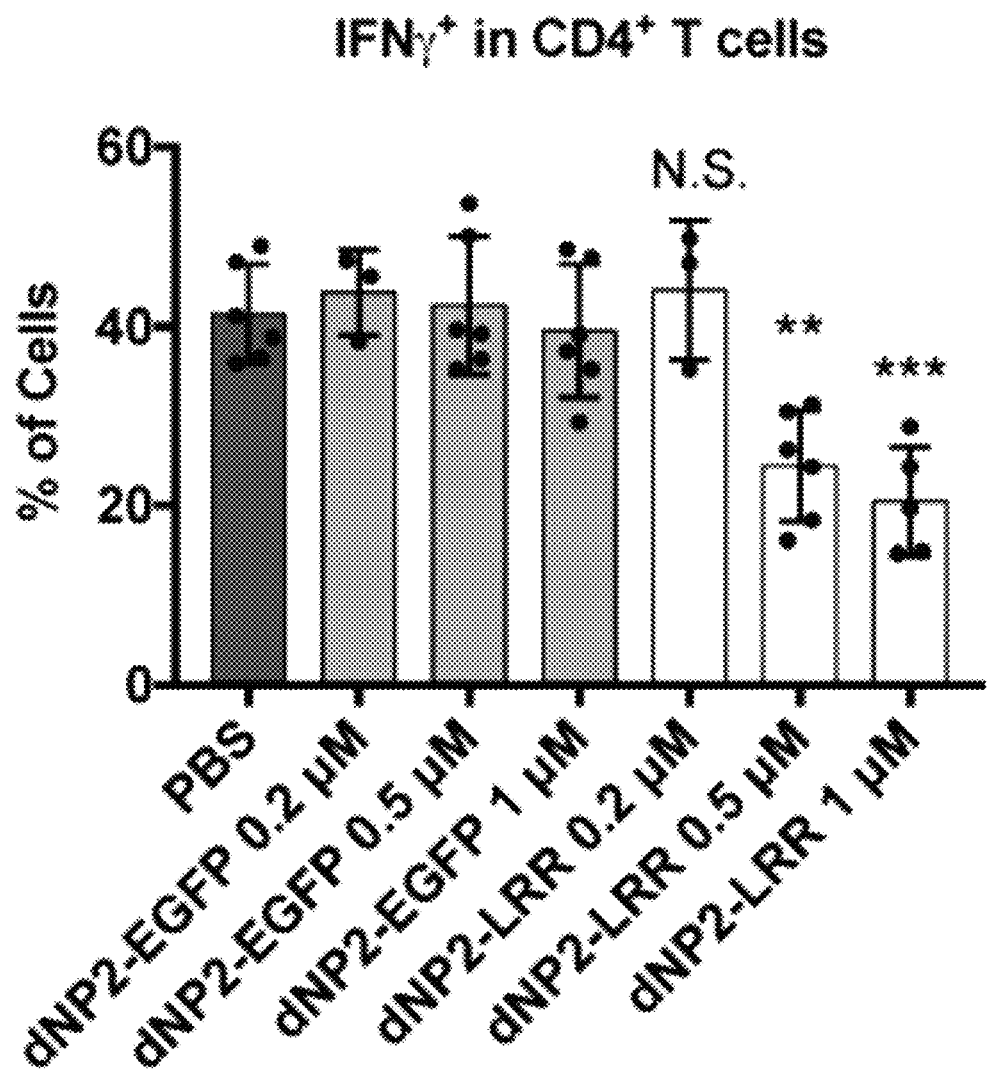
FIG. 49 shows a result of differentiating naive CD4+ T cells under Th1 condition with dNP2-LRR (Example 1) or dNP2-EGFP (Comparative Example 2) at various concentrations (0.2 μM, 0.5 μM, 1 μM) or PBS and measuring the frequency of $IFN_\gamma^+$-producing cells in CD4+ T cells by flow cytometry. n=3-6 and error bars indicate S.D. *P<0.05, P<0.01 and *P<0.001. N.A.: not activated, N.S.: not significant.

FIG. 49 shows a result of differentiating naive CD4⁺ T cells under Th1 condition with dNP2-LRR (Example 1) or dNP2-EGFP (Comparative Example 2) at various concentrations (0.2 μM, 0.5 μM, 1 μM) or PBS and measuring the frequency of IFN$_\gamma$⁺-producing cells in CD4⁺ T cells by flow cytometry. n=3-6 and error bars indicate S.D. *P<0.05, P<0.01 and *P<0.001. N.A.: not activated, N.S.: not significant.

From FIG. 48 and FIG. 49, it was confirmed that, when the naive CD4⁺ T cells treated with the dNP2-LRR fusion protein of Example 1 were differentiated into Th1 cells, the population of IFNγ-producing cells was decreased significantly.

Figure 50:
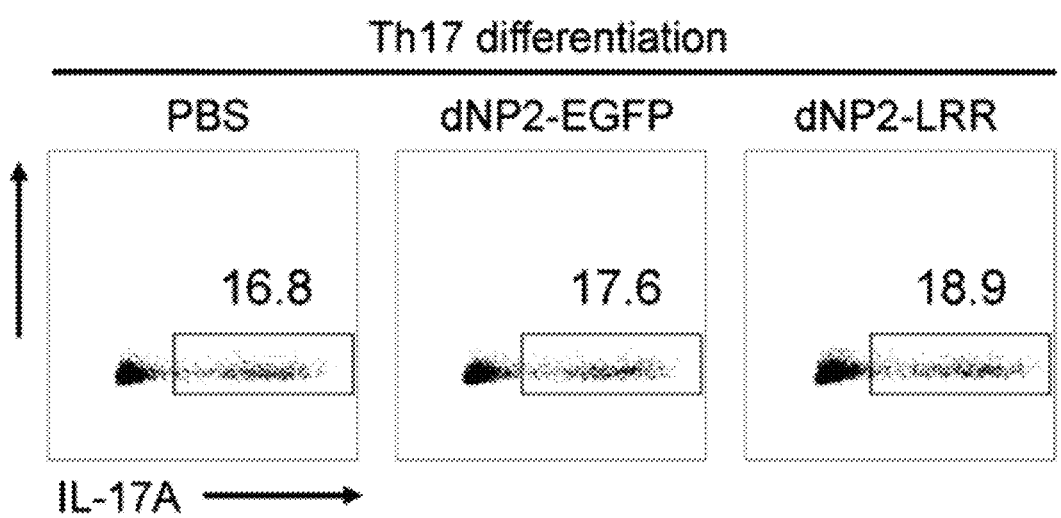
FIG. 50 shows a result of differentiating naive CD4+ T cells under Th17 condition with dNP2-LRR (Example 1) or dNP2-EGFP (Comparative Example 2) at various concentrations (0.2 μM, 0.5 μM, 1 μM) or PBS and analyzing the result by flow cytometry.

FIG. 50 shows a result of differentiating naive CD4⁺ T cells under Th17 condition with dNP2-LRR (Example 1) or dNP2-EGFP (Comparative Example 2) at various concentrations (0.2 μM, 0.5 μM, 1 μM) or PBS and analyzing the result by flow cytometry.

Figure 51:
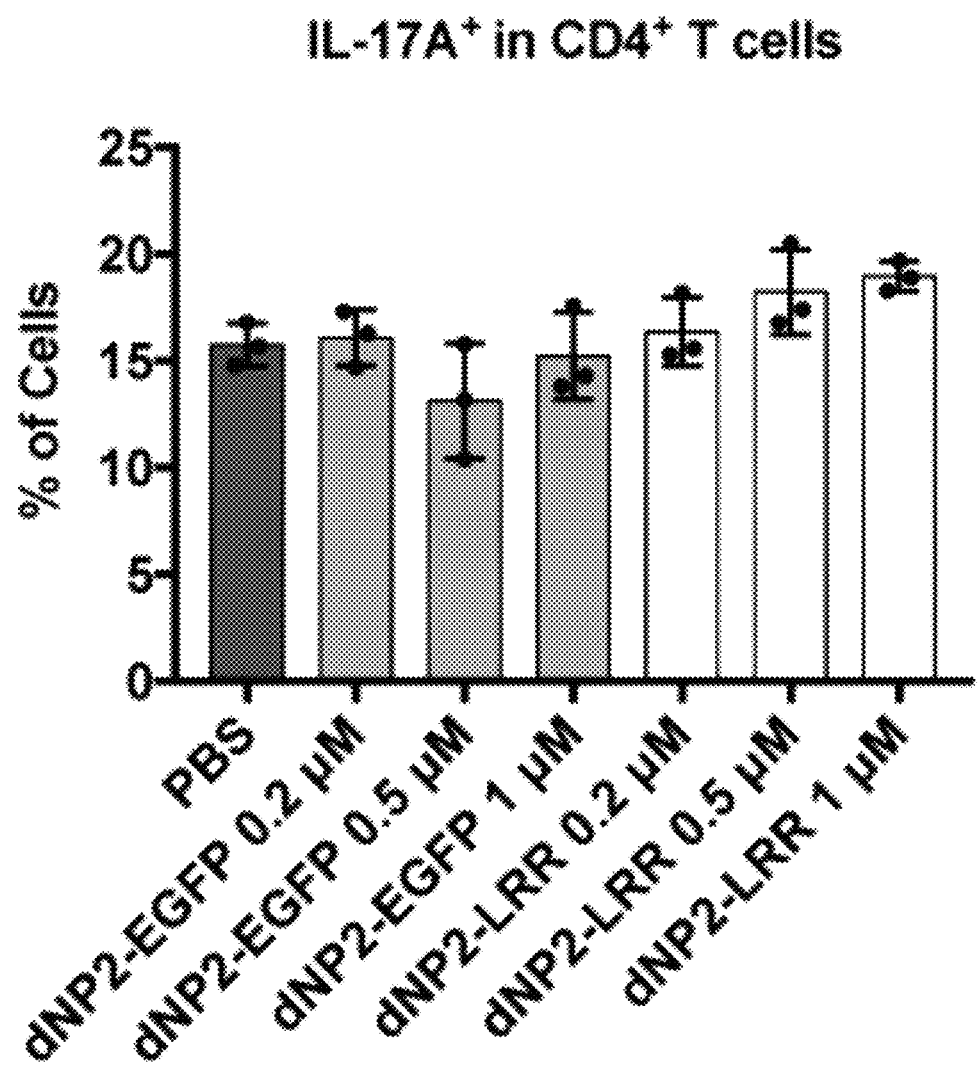
FIG. 51 shows a result of differentiating naive CD4+ T cells under Th17 condition with dNP2-LRR (Example 1) or dNP2-EGFP (Comparative Example 2) at various concentrations (0.2 μM, 0.5 μM, 1 μM) or PBS and measuring the frequency of IL-17A-producing cells in CD4+ T cells by flow cytometry. n=3-6 and error bars indicate S.D. *P<0.05, P<0.01 and *P<0.001. N.A.: not activated, N.S.: not significant.

FIG. 51 shows a result of differentiating naive CD4⁺ T cells under Th17 condition with dNP2-LRR (Example 1) or dNP2-EGFP (Comparative Example 2) at various concentrations (0.2 μM, 0.5 μM, 1 μM) or PBS and measuring the frequency of IL-17A-producing cells in CD4⁺ T cells by flow cytometry. n=3-6 and error bars indicate S.D. *P<0.05, P<0.01 and *P<0.001. N.A.: not activated, N.S.: not significant.

From FIG. 50 and FIG. 51, it was confirmed that there was no significant difference when the naive CD4⁺ T cells treated with the dNP2-LRR fusion protein of Example 1 were differentiated into Th17 cells.

Figure 52:
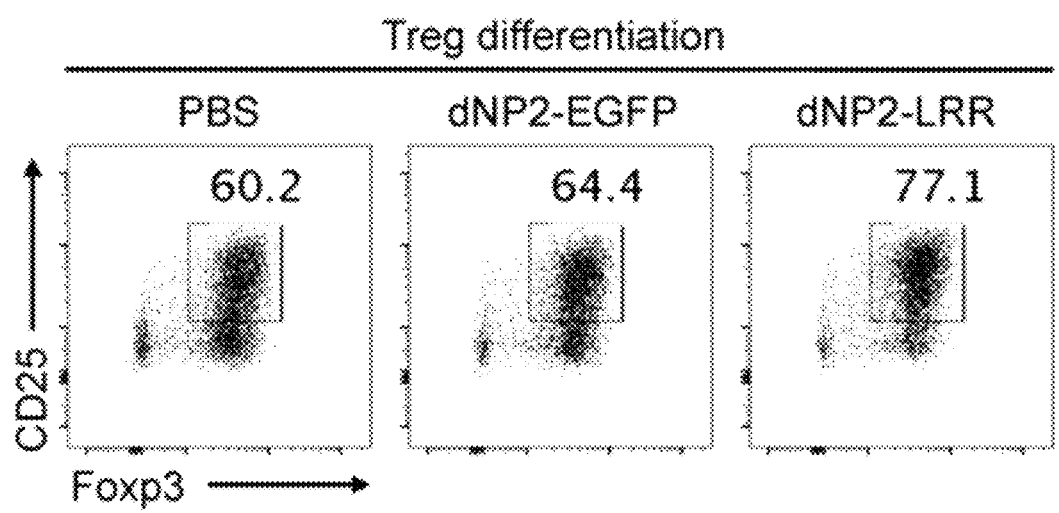
FIG. 52 shows a result of differentiating naive CD4+ T cells under iTreg condition with dNP2-LRR (Example 1) or dNP2-EGFP (Comparative Example 2) at various concentrations (0.2 μM, 0.5 μM, 1 μM) or PBS and analyzing the result by flow cytometry.

FIG. 52 shows a result of differentiating naive CD4⁺ T cells under iTreg condition with dNP2-LRR (Example 1) or dNP2-EGFP (Comparative Example 2) at various concentrations (0.2 μM, 0.5 μM, 1 μM) or PBS and analyzing the result by flow cytometry.

Figure 53:
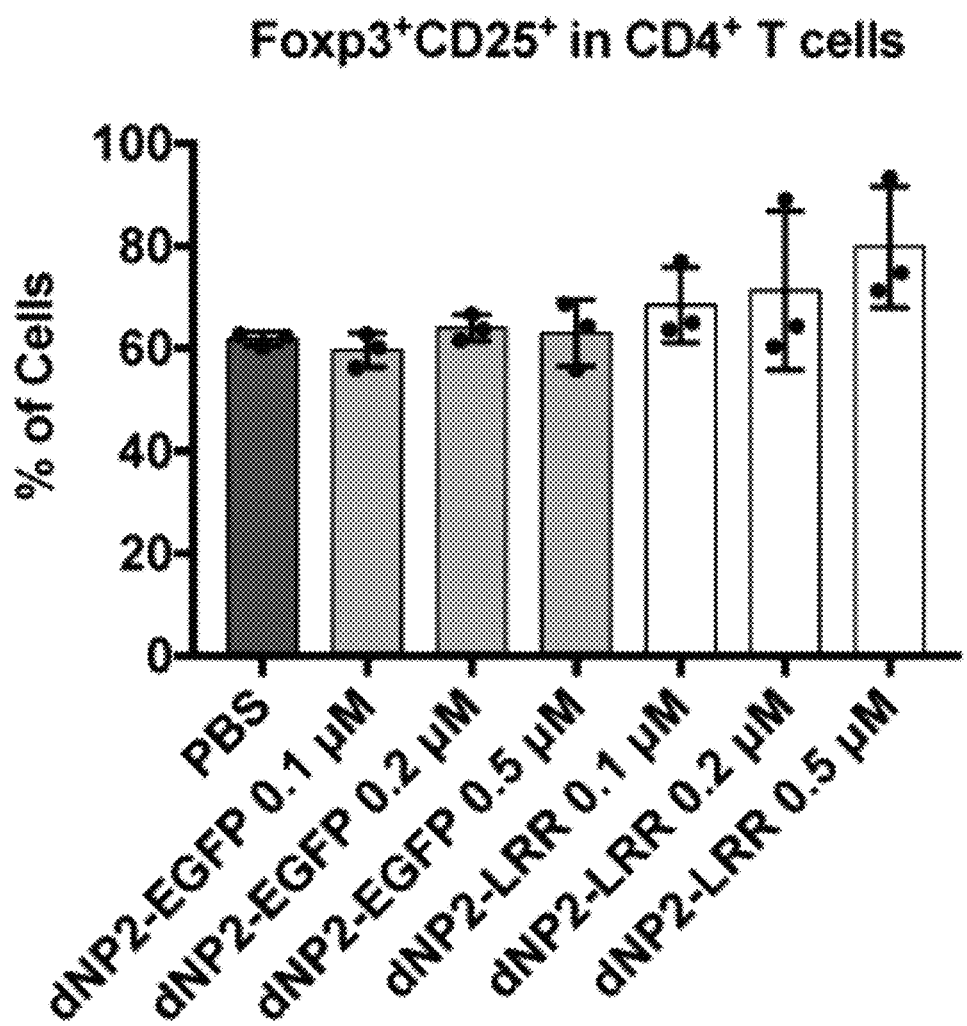
FIG. 53 shows a result of differentiating naive CD4+ T cells under Th17 condition with dNP2-LRR (Example 1) or dNP2-EGFP (Comparative Example 2) at various concentrations (0.2 μM, 0.5 μM, 1 μM) or PBS and measuring the frequency of Foxp3+CD25+ T cells in CD4+ T cells by flow cytometry. n=3-6 and error bars indicate S.D. *P<0.05, P<0.01 and *P<0.001. N.A.: not activated, N.S.: not significant.

FIG. 53 shows a result of differentiating naive CD4⁺ T cells under Th17 condition with dNP2-LRR (Example 1) or dNP2-EGFP (Comparative Example 2) at various concentrations (0.2 μM, 0.5 μM, 1 μM) or PBS and measuring the frequency of Foxp3⁺CD25⁺ T cells in CD4⁺ T cells by flow cytometry. n=3-6 and error bars indicate S.D. *P<0.05, P<0.01 and *P<0.001. N.A.: not activated, N.S.: not significant.

From FIG. 52 and FIG. 53, it was confirmed that the naive CD4⁺ T cells treated with the dNP2-LRR fusion protein of Example 1 showed no significant difference when they were differentiated into regulatory T cells (Foxp3⁺CD25⁺CD4⁺ cells).

Test Example 12 Analysis of Stability of Fusion Protein

It was investigated whether the dNP2-LRR fusion protein of Example 1 of the present disclosure exhibits cytotoxicity.

Naive CD4⁺ T cells were isolated using a mouse naive CD4⁺ T-cell isolation kit (Miltenyi Biotec, Bergisch Gladbach, Germany) according to the manufacturer's protocol. The purified naive T cells were activated with 1:5 of anti-CD3/CD28 Dynabeads (Gibco, Co Dublin, Ireland). After adding a fusion protein, the cells were cultured at 37° C. for 1 day. Then, the number of live cells was counted using a live/dead staining kit. In addition, the proportion of live T cells was analyzed by flow cytometry. The flow cytometry was performed in the same manner as in Test Example 10.

dNP2-LRR (Example 1) or dNP2-EGFP (Comparative Example 2) was used as the fusion protein, and PBS was used as a control group.

Figure 54:
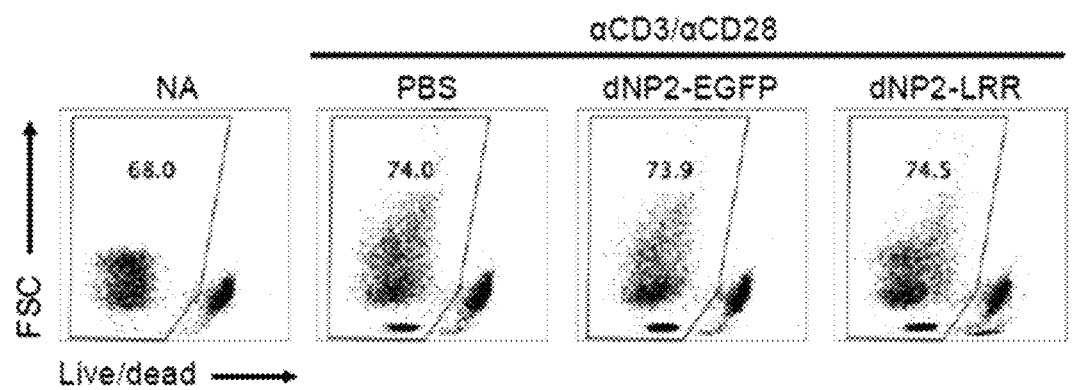
FIG. 54 shows a result of measuring the surface expression level of CD44 in activated CD4 T cells by flow cytometry after incubation with 1 μM dNP2-LRR (Example 1) or dNP2-EGFP (Comparative Example 2) or PBS.
Figure 55:
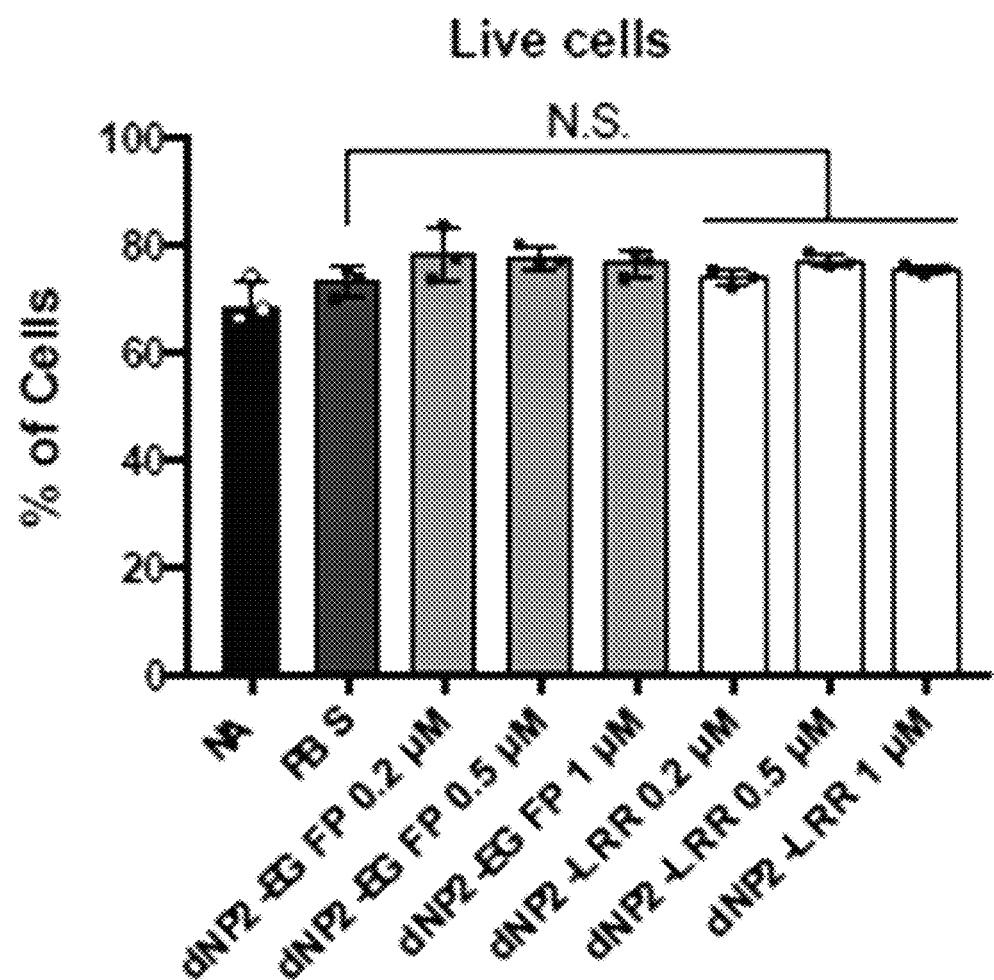
FIG. 55 shows a result of measuring the proportion of live T cells in activated CD4 T cells after incubation with dNP2-LRR (Example 1) or dNP2-EGFP (Comparative Example 2) at various concentrations (0.2 μM, 0.5 μM, 1 μM) or PBS. n=3 and error bars indicate S.D. N.A.: not activated, N.S.: not significant.

FIG. 54 shows a result of measuring the surface expression level of CD44 in activated CD4 T cells by flow cytometry after incubation with 1 μM dNP2-LRR (Example 1) or dNP2-EGFP (Comparative Example 2) or PBS, FIG. 55 shows a result of measuring the proportion of live T cells in activated CD4 T cells after incubation with dNP2-LRR (Example 1) or dNP2-EGFP (Comparative Example 2) at various concentrations (0.2 μM, 0.5 μM, 1 μM) or PBS. n=3 and error bars indicate S.D. N.A.: not activated, N.S.: not significant.

From FIG. 54 and FIG. 55, it was confirmed that the fusion proteins of Example 1 and Comparative Example 2 do not show toxicity for T cells. That is to say, it can be seen that the preventive or therapeutic effect of the dNP2-LRR fusion protein of Example 1, which specifically regulates the differentiation of T cells, is not due to toxicity.

While the specific exemplary embodiments of the present disclosure have been described in detail, it will be obvious to those having ordinary knowledge in the art that the detailed description merely describes preferred exemplary embodiments and the scope of the present disclosure is not limited thereby. Accordingly, the substantial scope of the present disclosure will be defined by the appended claims and their equivalents.

What is claimed is:

1. A fusion protein comprising (a) a cell-penetrating peptide comprising the amino acid sequence of SEQ ID NO: 1; and (b) an LRR domain peptide consisting of the amino acid sequence of SEQ ID NO: 3.

2. The fusion protein according to claim 1, comprising the amino acid sequence of SEQ ID NO: 4.

3. A pharmaceutical composition comprising the fusion protein according to claim 1 as an active ingredient, and a pharmaceutically acceptable carrier.

4. A method for treating a neurological autoimmune disease, comprising administering the pharmaceutical composition according to claim 3 to a patient with an autoimmune disease.

5. A gene encoding the fusion protein according to claim 1.

6. A recombinant vector comprising the gene according to claim 5.

7. A transformant transformed with the recombinant vector according to claim 6.

* * * * *

SEQUENCE LISTING

```
<160> NUMBER OF SEQ ID NOS: 27

<210> SEQ ID NO 1
<211> LENGTH: 24
<212> TYPE: PRT
<213> ORGANISM: Artificial Sequence
<220> FEATURE:
<223> OTHER INFORMATION: penetrating peptide; dNP2

<400> SEQUENCE: 1

Lys Ile Lys Lys Val Lys Lys Gly Arg Lys Gly Ser Lys Ile Lys
1               5                   10                  15

Lys Val Lys Lys Lys Gly Arg Lys
            20

<210> SEQ ID NO 2
<211> LENGTH: 975
<212> TYPE: PRT
<213> ORGANISM: Artificial Sequence
<220> FEATURE:
<223> OTHER INFORMATION: NLRX1 protein

<400> SEQUENCE: 2

Met Arg Trp Gly Cys His Leu Pro Arg Thr Ser Trp Gly Ser Gly Leu
1               5                   10                  15

Gly Arg Thr Pro Gln Leu Pro Asp Glu His Ile Ser Phe Leu Ile Gln
            20                  25                  30

Trp Ser Trp Pro Phe Lys Gly Val His Pro Leu Arg Pro Arg Ala
        35                  40                  45

Phe Ile Arg Tyr His Gly Asn Ser Ala Asp Ser Ala Pro Pro Gly
    50                  55                  60

Arg His Gly Gln Leu Phe Arg Ser Ile Ser Ala Thr Glu Ala Ile Gln
65                  70                  75                  80

Arg His Arg Arg Asn Leu Thr Glu Trp Phe Ser Arg Leu Pro Arg Glu
                85                  90                  95

Glu Arg Gln Phe Gly Pro Thr Phe Ala Leu Asp Thr Val His Val Asp
            100                 105                 110

Pro Val Ile Arg Glu Ser Thr Pro Asp Glu Leu Leu Arg Pro Ser Thr
        115                 120                 125

Glu Leu Ala Thr Gly His Gln Gln Thr Gln Ala Gly Leu Pro Pro Leu
    130                 135                 140

Ala Leu Ser Gln Leu Phe Asp Pro Asp Ser Cys Gly Arg Arg Val Gln
145                 150                 155                 160
```

```
Thr Val Val Leu Tyr Gly Thr Val Gly Thr Gly Lys Ser Thr Leu Val
                165                 170                 175
Arg Lys Met Val Leu Asp Trp Cys Tyr Gly Arg Leu Pro Ala Phe Glu
            180                 185                 190
Leu Leu Ile Pro Phe Ser Cys Glu Asp Leu Ser Ser Leu Gly Ser Thr
        195                 200                 205
Pro Ala Ser Leu Cys Gln Leu Val Thr Gln Arg Tyr Thr Pro Leu Lys
    210                 215                 220
Glu Val Leu Pro Leu Met Thr Ala Ala Gly Ser Arg Leu Leu Phe Val
225                 230                 235                 240
Leu His Gly Leu Glu Arg Leu Asn Leu Asp Phe Arg Leu Ala Gly Thr
                245                 250                 255
Gly Leu Cys Ser Asp Pro Glu Glu Pro Gly Pro Ala Ala Ile Ile
            260                 265                 270
Val Asn Leu Leu Arg Lys Tyr Met Leu Pro Glu Ala Ser Ile Leu Val
        275                 280                 285
Thr Thr Arg Pro Ser Thr Ile Ser Arg Ile Pro Ser Lys Tyr Val Gly
    290                 295                 300
Arg Tyr Gly Glu Ile Cys Gly Phe Ser Asp Thr Asn Leu Gln Lys Leu
305                 310                 315                 320
Tyr Phe Gln Leu Arg Leu Asn Gln Pro Asp Cys Gly Tyr Gly Ala Gly
                325                 330                 335
Gly Ala Ser Val Ser Val Thr Pro Ala Gln Arg Asp Asn Leu Ile Gln
            340                 345                 350
Met Leu Ser Arg Asn Leu Glu Gly His His Gln Ile Ala Ala Ala Cys
        355                 360                 365
Phe Leu Pro Ser Tyr Cys Trp Leu Val Cys Ala Thr Leu His Phe Leu
    370                 375                 380
His Ala Pro Thr Pro Ala Gly Gln Thr Leu Thr Ser Ile Tyr Thr Ser
385                 390                 395                 400
Phe Leu Arg Leu Asn Phe Ser Gly Glu Thr Leu Asp Ser Thr His Thr
                405                 410                 415
Ser Asn Leu Ser Leu Met Ser Tyr Ala Ala Arg Thr Met Gly Lys Leu
            420                 425                 430
Ala Tyr Glu Gly Val Ser Ser Arg Lys Thr Tyr Phe Ser Glu Glu Asp
        435                 440                 445
Val Arg Gly Cys Leu Glu Ala Gly Ile Lys Thr Glu Glu Phe Gln
    450                 455                 460
Leu Leu Gln Ile Phe Arg Arg Asp Ala Leu Arg Phe Leu Ala Pro
465                 470                 475                 480
Cys Val Glu Pro Gly His Leu Gly Thr Phe Val Phe Thr Val Pro Ala
                485                 490                 495
Met Gln Glu Tyr Leu Ala Ala Leu Tyr Ile Val Leu Gly Leu Arg Lys
            500                 505                 510
Thr Ala Leu Gln Arg Val Gly Lys Glu Val Val Glu Phe Val Gly Arg
        515                 520                 525
Val Gly Glu Asp Val Ser Leu Val Leu Gly Ile Val Ala Lys Leu Leu
    530                 535                 540
Pro Leu Arg Ile Leu Pro Leu Leu Phe Asn Leu Leu Lys Val Val Pro
545                 550                 555                 560
Arg Val Phe Gly Arg Met Val Ser Lys Ser Arg Glu Ala Val Ala Gln
                565                 570                 575
Ala Met Val Leu Glu Met Phe Arg Glu Glu Asp Tyr Tyr Asn Asp Asp
```

```
                580                 585                 590
Val Leu Asp Gln Met Gly Ala Ser Ile Leu Gly Val Glu Gly Pro Arg
            595                 600                 605

Arg His Pro Asp Glu Pro Ser Glu Asp Glu Val Phe Glu Leu Phe Pro
            610                 615                 620

Met Phe Met Gly Gly Leu Leu Ser Ala His Asn Arg Ala Val Leu Ala
625                 630                 635                 640

Gln Leu Gly Cys Pro Ile Lys Asn Leu Asp Ala Leu Glu Asn Ala Gln
            645                 650                 655

Ala Ile Lys Lys Lys Leu Gly Lys Leu Gly Arg Gln Val Leu Pro Pro
            660                 665                 670

Ser Glu Leu Leu Asp His Leu Phe Phe His Tyr Glu Phe Gln Asn Gln
            675                 680                 685

Arg Phe Ser Ala Glu Val Leu Gly Ser Leu Arg Gln Leu Asn Leu Ala
            690                 695                 700

Gly Val Arg Met Thr Pro Leu Lys Cys Thr Val Val Ala Ser Val Leu
705                 710                 715                 720

Gly Ser Gly Arg His Pro Leu Asp Glu Val Asn Leu Ala Ser Cys Gln
            725                 730                 735

Leu Asp Pro Ala Gly Leu His Thr Leu Met Pro Val Leu Leu Arg Ala
            740                 745                 750

Arg Lys Leu Gly Leu Gln Leu Asn Asn Leu Gly Pro Glu Ala Cys Arg
            755                 760                 765

Asp Leu Arg Asp Leu Leu Leu His Asp Gln Cys Gln Ile Thr Thr Leu
            770                 775                 780

Arg Leu Ser Asn Asn Pro Leu Thr Ala Ala Gly Val Gly Leu Leu Met
785                 790                 795                 800

Asp Gly Leu Ala Gly Asn Thr Ser Val Thr His Leu Ser Leu Leu His
            805                 810                 815

Thr Asp Leu Gly Asp Glu Gly Leu Glu Leu Leu Ala Ala Gln Leu Asp
            820                 825                 830

Arg Asn Lys Gln Leu Gln Glu Leu Asn Val Ala Tyr Asn Gly Ala Gly
            835                 840                 845

Asp Thr Val Ala Leu Ala Leu Ala Lys Ala Ala Arg Glu His Pro Ser
            850                 855                 860

Leu Glu Leu Leu His Leu Tyr Phe Asn Glu Leu Ser Ser Glu Gly Arg
865                 870                 875                 880

Gln Val Leu Arg Asp Leu Gly Gly Ser Gly Glu Gly Gly Ala Arg Val
            885                 890                 895

Val Ala Ser Leu Thr Glu Gly Thr Ala Val Ser Glu Tyr Trp Ser Val
            900                 905                 910

Ile Leu Ser Glu Val Gln Arg Asn Val His Ser Trp Asp Pro Leu Arg
            915                 920                 925

Val Gln Arg His Leu Lys Leu Leu Leu Arg Asp Leu Glu Asp Ser Arg
            930                 935                 940

Gly Ala Thr Leu Asn Pro Trp Arg Lys Ala Gln Leu Leu Arg Val Glu
945                 950                 955                 960

Gly Glu Val Lys Thr Leu Leu Glu Gln Leu Gly Gly Ser Gly His
            965                 970                 975

<210> SEQ ID NO 3
<211> LENGTH: 301
<212> TYPE: PRT
<213> ORGANISM: Artificial Sequence
```

<220> FEATURE:
<223> OTHER INFORMATION: LRR domain from NLRX1 protein

<400> SEQUENCE: 3

```
Leu Leu Asp His Leu Phe Phe His Tyr Glu Phe Gln Asn Gln Arg Phe
1               5                   10                  15

Ser Ala Glu Val Leu Gly Ser Leu Arg Gln Leu Asn Leu Ala Gly Val
            20                  25                  30

Arg Met Thr Pro Leu Lys Cys Thr Val Val Ala Ser Val Leu Gly Ser
        35                  40                  45

Gly Arg His Pro Leu Asp Glu Val Asn Leu Ala Ser Cys Gln Leu Asp
    50                  55                  60

Pro Ala Gly Leu His Thr Leu Met Pro Val Leu Leu Arg Ala Arg Lys
65                  70                  75                  80

Leu Gly Leu Gln Leu Asn Asn Leu Gly Pro Glu Ala Cys Arg Asp Leu
                85                  90                  95

Arg Asp Leu Leu Leu His Asp Gln Cys Gln Ile Thr Thr Leu Arg Leu
            100                 105                 110

Ser Asn Asn Pro Leu Thr Ala Ala Gly Val Gly Leu Leu Met Asp Gly
        115                 120                 125

Leu Ala Gly Asn Thr Ser Val Thr His Leu Ser Leu Leu His Thr Asp
    130                 135                 140

Leu Gly Asp Glu Gly Leu Glu Leu Leu Ala Ala Gln Leu Asp Arg Asn
145                 150                 155                 160

Lys Gln Leu Gln Glu Leu Asn Val Ala Tyr Asn Gly Ala Gly Asp Thr
                165                 170                 175

Val Ala Leu Ala Leu Ala Lys Ala Ala Arg Glu His Pro Ser Leu Glu
            180                 185                 190

Leu Leu His Leu Tyr Phe Asn Glu Leu Ser Ser Glu Gly Arg Gln Val
        195                 200                 205

Leu Arg Asp Leu Gly Gly Ser Gly Glu Gly Gly Ala Arg Val Val Ala
    210                 215                 220

Ser Leu Thr Glu Gly Thr Ala Val Ser Glu Tyr Trp Ser Val Ile Leu
225                 230                 235                 240

Ser Glu Val Gln Arg Asn Val His Ser Trp Asp Pro Leu Arg Val Gln
                245                 250                 255

Arg His Leu Lys Leu Leu Arg Asp Leu Glu Asp Ser Arg Gly Ala
            260                 265                 270

Thr Leu Asn Pro Trp Arg Lys Ala Gln Leu Leu Arg Val Glu Gly Glu
        275                 280                 285

Val Lys Thr Leu Leu Glu Gln Leu Gly Gly Ser Gly His
    290                 295                 300
```

<210> SEQ ID NO 4
<211> LENGTH: 368
<212> TYPE: PRT
<213> ORGANISM: Artificial Sequence
<220> FEATURE:
<223> OTHER INFORMATION: Fusion protein; dNP2-LRR

<400> SEQUENCE: 4

```
Met Gly Ser Ser His His His His His His Ser Ser Gly Leu Val Pro
1               5                   10                  15

Arg Gly Ser His Met Ala Ser Lys Ile Lys Lys Val Lys Lys Lys Gly
            20                  25                  30

Arg Lys Gly Ser Lys Ile Lys Lys Val Lys Lys Lys Gly Arg Lys Val
```

```
            35                  40                  45
Asp Leu Leu Asp His Leu Phe Phe His Tyr Glu Phe Gln Asn Gln Arg
 50                  55                  60

Phe Ser Ala Glu Val Leu Gly Ser Leu Arg Gln Leu Asn Leu Ala Gly
 65                  70                  75                  80

Val Arg Met Thr Pro Leu Lys Cys Thr Val Ala Ser Val Leu Gly
                 85                  90                  95

Ser Gly Arg His Pro Leu Asp Glu Val Asn Leu Ala Ser Cys Gln Leu
                100                 105                 110

Asp Pro Ala Gly Leu His Thr Leu Met Pro Val Leu Arg Ala Arg
                115                 120                 125

Lys Leu Gly Leu Gln Leu Asn Asn Leu Gly Pro Glu Ala Cys Arg Asp
130                 135                 140

Leu Arg Asp Leu Leu His Asp Gln Cys Gln Ile Thr Thr Leu Arg
145                 150                 155                 160

Leu Ser Asn Asn Pro Leu Thr Ala Ala Gly Val Gly Leu Leu Met Asp
                165                 170                 175

Gly Leu Ala Gly Asn Thr Ser Val Thr His Leu Ser Leu Leu His Thr
                180                 185                 190

Asp Leu Gly Asp Glu Gly Leu Glu Leu Leu Ala Ala Gln Leu Asp Arg
                195                 200                 205

Asn Lys Gln Leu Gln Glu Leu Asn Val Ala Tyr Asn Gly Ala Gly Asp
210                 215                 220

Thr Val Ala Leu Ala Leu Ala Lys Ala Ala Arg Glu His Pro Ser Leu
225                 230                 235                 240

Glu Leu Leu His Leu Tyr Phe Asn Glu Leu Ser Ser Glu Gly Arg Gln
                245                 250                 255

Val Leu Arg Asp Leu Gly Gly Ser Gly Glu Gly Ala Arg Val Val
                260                 265                 270

Ala Ser Leu Thr Glu Gly Thr Ala Val Ser Glu Tyr Trp Ser Val Ile
                275                 280                 285

Leu Ser Glu Val Gln Arg Asn Val His Ser Trp Asp Pro Leu Arg Val
290                 295                 300

Gln Arg His Leu Lys Leu Leu Leu Arg Asp Leu Glu Asp Ser Arg Gly
305                 310                 315                 320

Ala Thr Leu Asn Pro Trp Arg Lys Ala Gln Leu Leu Arg Val Glu Gly
                325                 330                 335

Glu Val Lys Thr Leu Leu Glu Gln Leu Gly Gly Ser Gly His Glu Phe
                340                 345                 350

Asp Tyr Lys Asp Asp Asp Asp Lys Leu Glu His His His His His His
                355                 360                 365
```

<210> SEQ ID NO 5
<211> LENGTH: 6313
<212> TYPE: DNA
<213> ORGANISM: Artificial Sequence
<220> FEATURE:
<223> OTHER INFORMATION: plasmid DNA of Fusion protein dNP2-LRR

<400> SEQUENCE: 5

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tccctttagg      180 gttccgattt agtgctttac ggcacctcga ccccaaaaaa cttgattagg gtgatggttc     240
```

```
acgtagtggg ccatcgccct gatagacggt ttttcgccct ttgacgttgg agtccacgtt      300
ctttaatagt ggactcttgt tccaaactgg aacaacactc aaccctatct cggtctattc      360
ttttgattta taagggatttt tgccgatttc ggcctattgg ttaaaaaatg agctgattta     420
acaaaatttt aacgcgaatt ttaacaaaat attaacgttt acaatttcag gtggcacttt      480
tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatattttt gaaaaagccg tttctgtaat gaaggagaaa     660
actcaccgag gcagttccat aggatggcaa gatcctggta tcggtctgcg attccgactc     720
gtccaacatc aatacaacct attaattttcc cctcgtcaaa ataaggtta tcaagtgaga    780 aatcaccatg agtgacgact gaatccggtg agaatggcaa aagtttatgc atttctttcc     840
agacttgttc aacaggccag ccattacgct cgtcatcaaa atcactcgca tcaaccaaac     900
cgttattcat tcgtgattgc gcctgagcga gacgaaatac gcgatcgctg ttaaaaggac     960
aattacaaac aggaatcgaa tgcaaccggc gcaggaacac tgccagcgca tcaacaatat     1020
tttcacctga atcaggatat tcttctaata cctggaatgc tgttttcccg gggatcgcag     1080
tggtgagtaa ccatgcatca tcaggagtac ggataaaatg cttgatggtc ggaagaggca     1140
taaattccgt cagccagttt agtctgacca tctcatctgt aacatcattg gcaacgctac     1200
ctttgccatg tttcagaaac aactctggcg catcgggctt cccatacaat cgatagattg     1260
tcgcacctga ttgcccgaca ttatcgcgag cccattttata cccatataaa tcagcatcca     1320
tgttggaatt taatcgcggc ctagagcaag acgtttcccg ttgaatatgg ctcataacac     1380
cccttgtatt actgtttatg taagcagaca gttttattgt tcatgaccaa aatcccttaa     1440
cgtgagtttt cgttccactg agcgtcagac cccgtagaaa agatcaaagg atcttcttga     1500
gatccttttt ttctgcgcgt aatctgctgc ttgcaaacaa aaaaaccacc gctaccagcg     1560
gtggtttgtt tgccggatca agagctacca actctttttc cgaaggtaac tggcttcagc     1620
agagcgcaga taccaaatac tgtccttcta gtgtagccgt agttaggcca ccacttcaag     1680
aactctgtag caccgcctac atacctcgct ctgctaatcc tgttaccagt ggctgctgcc     1740
agtggcgata gtcgtgtct taccgggttg gactcaagac gatagttacc ggataaggcg     1800
cagcggtcgg gctgaacggg gggttcgtgc acacagccca gcttggagcg aacgacctac     1860
accgaactga gatacctaca gcgtgagcta tgagaaagcg ccacgcttcc cgaagggaga     1920
aaggcggaca ggtatccggt aagcggcagg gtcggaacag gagagcgcac gagggagctt     1980
ccagggggaa acgcctggta tctttatagt cctgtcgggt ttcgccacct ctgacttgag     2040
cgtcgatttt tgtgatgctc gtcagggggg cggagcctat ggaaaaacgc cagcaacgcg     2100
gcctttttac ggttcctggc cttttgctgg ccttttgctc acatgttctt tcctgcgtta     2160
tcccctgatt ctgtggataa ccgtattacc gcctttgagt gagctgatac cgctcgccgc     2220
agccgaacga ccgagcgcag cgagtcagtg agcgaggaag cggaagagcg cctgatgcgg     2280
tattttctcc ttacgcatct gtgcggtatt tcacaccgca tatatggtgc actctcagta     2340
caatctgctc tgatgccgca tagttaagcc agtatacact ccgctatcgc tacgtgactg     2400
ggtcatggct gcgccccgac acccgccaac acccgctgac gcgccctgac gggcttgtct     2460
gctcccggca tccgcttaca gacaagctgt gaccgtctcc gggagctgca tgtgtcagag     2520
gttttcaccg tcatcaccga aacgcgcgag gcagctgcgg taaagctcat cagcgtggtc     2580
```

```
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttcccccatc ggtgatgtcg gcgatatagg cgccagcaac cgcacctgtg    4920
gcgccggtga tgccggccac gatgcgtccg gcgtagagga tcgagatctc gatcccgcga    4980
```

-continued

```
aattaatacg actcactata ggggaattgt gagcggataa caattcccct ctagaaataa      5040
ttttgtttaa ctttaagaag gagatatacc atgggcagca gccatcatca tcatcatcac      5100
agcagcggcc tggtgccgcg cggcagccat atggctagca agatcaagaa ggttaaaaaa      5160
aagggtcgca agggctctaa aattaaaaaa gtcaagaaga aggaagaaa agtcgacctt       5220
cttgaccatc tcttcttcca ctatgagttc cagaaccagc gcttctcagc tgaggtgctg      5280
ggctccctac gccagctcaa tttagcaggg gtgcgcatga caccctcaa gtgcacagtg       5340
gtagcctctg tactgggaag tggaaggcac ccctggatg aggtgaactt ggcctcctgc       5400
cagctggatc cgctgggct acacactctc atgcctgtcc tcctgcgtgc cggaaactg        5460
gggttgcaac tcaacaatct gggccccgag gcctgcagag acctccgaga cctgctctta      5520
cacgatcaat gccagatcac cactcttagg ctctccaaca acccactgac agcagctggt     5580
gtgggcttac tgatggacgg gctggcagga aacacttcgg tgacacacct gtctctgctg     5640
cacactgacc ttggagacga gggactggaa ctgctggctg cccagctgga ccgaaacaaa     5700
caactgcagg agctgaacgt ggcctacaac ggtgctggtg acacagtggc tctggccttg     5760
gctaaggctg ctcgggagca cccttccctg gagctgctgc acctctactt caatgagctg     5820
agttcagagg gccgccaggt cctgcgggat tggggggct ctggtgaagg tggtgcccgg      5880
gtcgtagcct cgctgacaga agggacggcg gtgtctgagt actggtcagt gatccttagt    5940
gaagtccagc gcaacgtcca cagctgggac ccgctccggg tccagaggca tctcaagctg     6000
ctgctccgtg atctggagga cagccggggc gccacccta atccctggcg caaggctcag      6060
cttctgcgag tggagggcga ggtcaagact cttctggagc agctgggagg ttctggacac     6120
gaattcgatt acaaggatga cgatgacaag ctcgagcacc accaccacca ccactgagat     6180
ccggctgcta acaaagcccg aaaggaagct gagttggctg ctgccaccgc tgagcaataa     6240
ctagcataac ccttggggc ctctaaacgg gtcttgaggg gttttttgct gaaaggagga     6300
actatatccg gat                                                       6313
```

<210> SEQ ID NO 6
<211> LENGTH: 981
<212> TYPE: PRT
<213> ORGANISM: Artificial Sequence
<220> FEATURE:
<223> OTHER INFORMATION: Fusion protein dNP2-LRR

<400> SEQUENCE: 6

```
Ala Ala Gly Ala Thr Cys Ala Ala Gly Ala Gly Gly Thr Thr Ala
1               5                   10                  15

Ala Ala Ala Ala Ala Ala Ala Gly Gly Gly Thr Cys Gly Cys Ala Ala
                20                  25                  30

Gly Gly Gly Cys Thr Cys Thr Ala Ala Ala Thr Thr Ala Ala Ala
            35                  40                  45

Ala Ala Ala Gly Thr Cys Ala Ala Gly Ala Ala Gly Ala Ala Gly
        50                  55                  60

Gly Ala Ala Gly Ala Ala Ala Gly Thr Cys Gly Ala Cys Cys Thr
65                  70                  75                  80

Thr Cys Thr Thr Gly Ala Cys Cys Ala Thr Cys Thr Cys Thr
                85                  90                  95

Thr Thr Cys Cys Ala Cys Thr Ala Thr Gly Ala Gly Thr Thr Cys
            100                 105                 110

Ala Gly Ala Ala Cys Cys Ala Gly Cys Gly Cys Thr Thr Cys Thr
```

-continued

```
        115                 120                 125

Ala Gly Cys Thr Gly Ala Gly Gly Thr Gly Cys Thr Gly Gly Gly Cys
    130                 135                 140

Thr Cys Cys Cys Thr Ala Cys Gly Cys Cys Ala Gly Cys Thr Cys Ala
145                 150                 155                 160

Ala Thr Thr Thr Ala Gly Cys Ala Gly Gly Gly Gly Thr Gly Cys Gly
                165                 170                 175

Cys Ala Thr Gly Ala Cys Ala Cys Cys Cys Cys Thr Cys Ala Ala Gly
            180                 185                 190
Thr Gly Cys Ala Cys Ala Gly Thr Gly Gly Thr Ala Gly Cys Cys Thr
        195                 200                 205

Cys Thr Gly Thr Ala Cys Thr Gly Gly Gly Ala Ala Gly Thr Gly Gly
    210                 215                 220

Ala Ala Gly Gly Cys Ala Cys Cys Cys Cys Cys Thr Gly Gly Ala Thr
225                 230                 235                 240
Gly Ala Gly Gly Thr Gly Ala Ala Cys Thr Thr Gly Gly Cys Cys Thr
                245                 250                 255
Cys Cys Thr Gly Cys Cys Ala Gly Cys Thr Gly Gly Ala Thr Cys Cys
            260                 265                 270

Cys Gly Cys Thr Gly Gly Gly Cys Thr Ala Cys Ala Cys Ala Cys Thr
        275                 280                 285
Cys Thr Cys Ala Thr Gly Cys Cys Thr Gly Thr Cys Cys Thr Cys Cys
    290                 295                 300

Thr Gly Cys Gly Thr Gly Cys Cys Cys Gly Gly Ala Ala Ala Cys Thr
305                 310                 315                 320
Gly Gly Gly Gly Thr Thr Gly Cys Ala Ala Cys Thr Cys Ala Ala Cys
                325                 330                 335

Ala Ala Thr Cys Thr Gly Gly Gly Cys Cys Cys Cys Gly Ala Gly Gly
            340                 345                 350

Cys Cys Thr Gly Cys Ala Gly Ala Gly Ala Cys Cys Thr Cys Cys Gly
        355                 360                 365

Ala Gly Ala Cys Cys Thr Gly Cys Thr Cys Thr Thr Ala Cys Ala Cys
    370                 375                 380

Gly Ala Thr Cys Ala Ala Thr Gly Cys Cys Ala Gly Ala Thr Cys Ala
385                 390                 395                 400

Cys Cys Ala Cys Thr Cys Thr Thr Ala Gly Gly Cys Thr Cys Thr Cys
                405                 410                 415
Cys Ala Ala Cys Ala Ala Cys Cys Cys Ala Cys Thr Gly Ala Cys Ala
            420                 425                 430

Gly Cys Ala Gly Cys Thr Gly Gly Thr Gly Thr Gly Gly Gly Cys Thr
        435                 440                 445

Thr Ala Cys Thr Gly Ala Thr Gly Gly Ala Cys Gly Gly Gly Cys Thr
    450                 455                 460
Gly Gly Cys Ala Gly Gly Ala Ala Ala Cys Ala Cys Thr Thr Cys Gly
465                 470                 475                 480
Gly Thr Gly Ala Cys Ala Cys Ala Cys Cys Thr Gly Thr Cys Thr Cys
                485                 490                 495
Thr Gly Cys Thr Gly Cys Ala Cys Ala Cys Thr Gly Ala Cys Cys Thr
            500                 505                 510

Thr Gly Gly Ala Gly Ala Cys Gly Ala Gly Gly Gly Ala Cys Thr Gly
        515                 520                 525

Gly Ala Ala Cys Thr Gly Cys Thr Gly Gly Cys Thr Gly Cys Cys Cys
    530                 535                 540
```

Ala Gly Cys Thr Gly Gly Ala Cys Cys Gly Ala Ala Ala Cys Ala Ala
545 550 555 560

Ala Cys Ala Ala Cys Thr Gly Cys Ala Gly Gly Ala Gly Cys Thr Gly
565 570 575

Ala Ala Cys Gly Thr Gly Gly Cys Cys Thr Ala Cys Ala Ala Cys Gly
580 585 590

Gly Thr Gly Cys Thr Gly Gly Thr Gly Ala Cys Ala Cys Ala Gly Thr
595 600 605

Gly Gly Cys Thr Cys Thr Gly Gly Cys Cys Thr Thr Gly Gly Cys Thr
610 615 620

Ala Ala Gly Gly Cys Thr Gly Cys Thr Cys Gly Gly Gly Ala Gly Cys
625 630 635 640

Ala Cys Cys Cys Thr Thr Cys Cys Cys Thr Gly Gly Ala Gly Cys Thr
645 650 655

Gly Cys Thr Gly Cys Ala Cys Cys Thr Cys Thr Ala Cys Thr Thr Cys
660 665 670

Ala Ala Thr Gly Ala Gly Cys Thr Gly Ala Gly Thr Thr Cys Ala Gly
675 680 685

Ala Gly Gly Gly Cys Cys Gly Cys Cys Ala Gly Gly Thr Cys Cys Thr
690 695 700

Gly Cys Gly Gly Gly Ala Thr Thr Thr Gly Gly Gly Gly Gly Gly Cys
705 710 715 720

Thr Cys Thr Gly Gly Thr Gly Ala Ala Gly Gly Thr Gly Gly Thr Gly
725 730 735

Cys Cys Cys Gly Gly Gly Thr Cys Gly Thr Ala Gly Cys Cys Thr Cys
740 745 750

Gly Cys Thr Gly Ala Cys Ala Gly Ala Ala Gly Gly Gly Ala Cys Gly
755 760 765

Gly Cys Gly Gly Thr Gly Thr Cys Thr Gly Ala Gly Thr Ala Cys Thr
770 775 780

Gly Gly Thr Cys Ala Gly Thr Gly Ala Thr Cys Cys Thr Thr Ala Gly
785 790 795 800

Thr Gly Ala Ala Gly Thr Cys Cys Ala Gly Cys Gly Cys Ala Ala Cys
805 810 815

Gly Thr Cys Cys Ala Cys Ala Gly Cys Thr Gly Gly Gly Ala Cys Cys
820 825 830

Cys Gly Cys Thr Cys Cys Gly Gly Gly Thr Cys Cys Ala Gly Ala Gly
835 840 845

Gly Cys Ala Thr Cys Thr Cys Ala Ala Gly Cys Thr Gly Cys Thr Gly
850 855 860

Cys Thr Cys Cys Gly Thr Gly Ala Thr Cys Thr Gly Gly Ala Gly Gly
865 870 875 880

Ala Cys Ala Gly Cys Cys Gly Gly Gly Gly Cys Gly Cys Cys Ala Cys
885 890 895

Cys Cys Thr Thr Ala Ala Thr Cys Cys Cys Thr Gly Gly Cys Gly Cys
900 905 910

Ala Ala Gly Gly Cys Thr Cys Ala Gly Cys Thr Thr Cys Thr Gly Cys
915 920 925

Gly Ala Gly Thr Gly Gly Ala Gly Gly Gly Cys Gly Ala Gly Gly Thr
930 935 940

Cys Ala Ala Gly Ala Cys Thr Cys Thr Thr Cys Thr Gly Gly Ala Gly
945 950 955 960

```
Cys Ala Gly Cys Thr Gly Gly Ala Gly Thr Thr Cys Thr Gly
                 965                 970                 975
Gly Ala Cys Ala Cys
            980

<210> SEQ ID NO 7
<211> LENGTH: 549
<212> TYPE: PRT
<213> ORGANISM: Artificial Sequence
<220> FEATURE:
<223> OTHER INFORMATION: Fusion protein; dNP2-NBD

<400> SEQUENCE: 7

Met Gly Ser Ser His His His His His Ser Ser Gly Leu Val Pro
1               5                   10                  15

Arg Gly Ser His Met Ala Ser Lys Ile Lys Lys Val Lys Lys Lys Gly
                20                  25                  30

Arg Lys Gly Ser Lys Ile Lys Lys Val Lys Lys Gly Arg Lys Val
            35                  40                  45

Asp Ala Thr Glu Ala Ile Gln Arg His Arg Arg Asn Leu Thr Glu Trp
        50                  55                  60

Phe Ser Arg Leu Pro Arg Glu Glu Arg Gln Phe Gly Pro Thr Phe Ala
65                  70                  75                  80

Leu Asp Thr Val His Val Asp Pro Val Ile Arg Glu Ser Thr Pro Asp
                85                  90                  95

Glu Leu Leu Arg Pro Ser Thr Glu Leu Ala Thr Gly His Gln Gln Thr
                100                 105                 110

Gln Ala Gly Leu Pro Pro Leu Ala Leu Ser Gln Leu Phe Asp Pro Asp
                115                 120                 125

Ser Cys Gly Arg Arg Val Gln Thr Val Val Leu Tyr Gly Thr Val Gly
            130                 135                 140

Thr Gly Lys Ser Thr Leu Val Arg Lys Met Val Leu Asp Trp Cys Tyr
145                 150                 155                 160

Gly Arg Leu Pro Ala Phe Glu Leu Leu Ile Pro Phe Ser Cys Glu Asp
                165                 170                 175

Leu Ser Ser Leu Gly Ser Thr Pro Ala Ser Leu Cys Gln Leu Val Thr
                180                 185                 190

Gln Arg Tyr Thr Pro Leu Lys Glu Val Leu Pro Leu Met Thr Ala Ala
            195                 200                 205

Gly Ser Arg Leu Leu Phe Val Leu His Gly Leu Glu Arg Leu Asn Leu
210                 215                 220

Asp Phe Arg Leu Ala Gly Thr Gly Leu Cys Ser Asp Pro Glu Glu Pro
225                 230                 235                 240

Gly Pro Pro Ala Ala Ile Ile Val Asn Leu Leu Arg Lys Tyr Met Leu
                245                 250                 255

Pro Glu Ala Ser Ile Leu Val Thr Thr Arg Pro Ser Thr Ile Ser Arg
                260                 265                 270

Ile Pro Ser Lys Tyr Val Gly Arg Tyr Gly Glu Ile Cys Gly Phe Ser
            275                 280                 285

Asp Thr Asn Leu Gln Lys Leu Tyr Phe Gln Leu Arg Leu Asn Gln Pro
        290                 295                 300

Asp Cys Gly Tyr Gly Ala Gly Ala Ser Val Ser Val Thr Pro Ala
305                 310                 315                 320

Gln Arg Asp Asn Leu Ile Gln Met Leu Ser Arg Asn Leu Glu Gly His
                325                 330                 335
```

His Gln Ile Ala Ala Ala Cys Phe Leu Pro Ser Tyr Cys Trp Leu Val
            340                 345                 350

Cys Ala Thr Leu His Phe Leu His Ala Pro Thr Pro Ala Gly Gln Thr
        355                 360                 365

Leu Thr Ser Ile Tyr Thr Ser Phe Leu Arg Leu Asn Phe Ser Gly Glu
    370                 375                 380

Thr Leu Asp Ser Thr His Thr Ser Asn Leu Ser Leu Met Ser Tyr Ala
385                 390                 395                 400

Ala Arg Thr Met Gly Lys Leu Ala Tyr Glu Gly Val Pro Ser Arg Lys
                405                 410                 415

Thr Tyr Phe Ser Glu Glu Asp Val Arg Gly Cys Leu Glu Ala Gly Ile
            420                 425                 430

Lys Thr Glu Glu Glu Phe Gln Leu Leu Gln Ile Phe Arg Arg Asp Ala
        435                 440                 445

Leu Arg Phe Phe Leu Ala Pro Cys Val Glu Pro Gly His Leu Gly Thr
    450                 455                 460

Phe Val Phe Thr Val Pro Ala Met Gln Gly Tyr Leu Ala Ala Leu Tyr
465                 470                 475                 480

Ser Val Leu Gly Leu Arg Lys Thr Ala Leu Gln Arg Val Gly Lys Glu
                485                 490                 495

Val Val Glu Phe Val Gly Arg Val Gly Glu Asp Val Ser Leu Val Leu
            500                 505                 510

Gly Ile Val Ala Lys Leu Leu Pro Leu Arg Ile Leu Pro Leu Leu Phe
        515                 520                 525

Asn Leu Leu Glu Phe Asp Tyr Lys Asp Asp Asp Lys Leu Glu His
    530                 535                 540

His His His His
545

<210> SEQ ID NO 8
<211> LENGTH: 355
<212> TYPE: PRT
<213> ORGANISM: Artificial Sequence
<220> FEATURE:
<223> OTHER INFORMATION: Fusion protein; TAT-LRR

<400> SEQUENCE: 8

Met Gly Ser Ser His His His His His Ser Ser Gly Leu Val Pro
1               5                   10                  15

Arg Gly Ser His Met Ala Ser Tyr Gly Arg Lys Lys Arg Arg Gln Arg
                20                  25                  30

Arg Arg Val Asp Leu Leu Asp His Leu Phe Phe His Tyr Glu Phe Gln
            35                  40                  45

Asn Gln Arg Phe Ser Ala Glu Val Leu Gly Ser Leu Arg Gln Leu Asn
        50                  55                  60

Leu Ala Gly Val Arg Met Thr Pro Leu Lys Cys Thr Val Val Ala Ser
65                  70                  75                  80

Val Leu Gly Ser Gly Arg His Pro Leu Asp Glu Val Asn Leu Ala Ser
                85                  90                  95

Cys Gln Leu Asp Pro Ala Gly Leu His Thr Leu Met Pro Val Leu Leu
            100                 105                 110

Arg Ala Arg Lys Leu Gly Leu Gln Leu Asn Asn Leu Gly Pro Glu Ala
        115                 120                 125

Cys Arg Asp Leu Arg Asp Leu Leu Leu His Asp Gln Cys Gln Ile Thr
    130                 135                 140

```
Thr Leu Arg Leu Ser Asn Asn Pro Leu Thr Ala Ala Gly Val Gly Leu
145                 150                 155                 160

Leu Met Asp Gly Leu Ala Gly Asn Thr Ser Val Thr His Leu Ser Leu
            165                 170                 175

Leu His Thr Asp Leu Gly Asp Glu Gly Leu Glu Leu Leu Ala Ala Gln
        180                 185                 190

Leu Asp Arg Asn Lys Gln Leu Gln Glu Leu Asn Val Ala Tyr Asn Gly
    195                 200                 205

Ala Gly Asp Thr Val Ala Leu Ala Leu Ala Lys Ala Arg Glu His
210                 215                 220

Pro Ser Leu Glu Leu Leu His Leu Tyr Phe Asn Glu Leu Ser Ser Glu
225                 230                 235                 240

Gly Arg Gln Val Leu Arg Asp Leu Gly Gly Ser Gly Glu Gly Ala
            245                 250                 255

Arg Val Val Ala Ser Leu Thr Glu Gly Thr Ala Val Ser Glu Tyr Trp
            260                 265                 270

Ser Val Ile Leu Ser Glu Val Gln Arg Asn Val His Ser Trp Asp Pro
            275                 280                 285

Leu Arg Val Gln Arg His Leu Lys Leu Leu Leu Arg Asp Leu Glu Asp
290                 295                 300

Ser Arg Gly Ala Thr Leu Asn Pro Trp Arg Lys Ala Gln Leu Leu Arg
305                 310                 315                 320

Val Glu Gly Glu Val Lys Thr Leu Leu Glu Gln Leu Gly Gly Ser Gly
            325                 330                 335

His Glu Phe Asp Tyr Lys Asp Asp Asp Lys Leu Glu His His His
        340                 345                 350

His His His
        355

<210> SEQ ID NO 9
<211> LENGTH: 27
<212> TYPE: DNA
<213> ORGANISM: Artificial Sequence
<220> FEATURE:
<223> OTHER INFORMATION: Forward primer of NLRX1

<400> SEQUENCE: 9
ctagtcgaca tgaggtgggg ctgccat                                      27

<210> SEQ ID NO 10
<211> LENGTH: 22
<212> TYPE: DNA
<213> ORGANISM: Artificial Sequence
<220> FEATURE:
<223> OTHER INFORMATION: Reverse primer of NLRX1

<400> SEQUENCE: 10
ccggaattcg tgtccagaac ct                                           22

<210> SEQ ID NO 11
<211> LENGTH: 62
<212> TYPE: DNA
<213> ORGANISM: Artificial Sequence
<220> FEATURE:
<223> OTHER INFORMATION: 1st Forward primer of dNP2-LRR insert

<400> SEQUENCE: 11
cggctagcaa aattaaaaaa gtcaagaaga aggaagaaa agtcgacctt cttgaccatc   60
tc                                                                 62
```

<210> SEQ ID NO 12
<211> LENGTH: 22
<212> TYPE: DNA
<213> ORGANISM: Artificial Sequence
<220> FEATURE:
<223> OTHER INFORMATION: 1st Reverse primer of dNP2-LRR insert

<400> SEQUENCE: 12
ccggaattcg tgtccagaac ct                                    22

<210> SEQ ID NO 13
<211> LENGTH: 66
<212> TYPE: DNA
<213> ORGANISM: Artificial Sequence
<220> FEATURE:
<223> OTHER INFORMATION: Secondary Forward primer of dNP2-LRR insert

<400> SEQUENCE: 13
ctagtcgaca agatcaagaa ggttaaaaaa aagggtcgca agggctctaa aattaaaaaa    60
gtcaag                                                              66

<210> SEQ ID NO 14
<211> LENGTH: 23
<212> TYPE: DNA
<213> ORGANISM: Artificial Sequence
<220> FEATURE:
<223> OTHER INFORMATION: Forward primer of mIl6

<400> SEQUENCE: 14
aggataccac tcccaacaga cct                                   23

<210> SEQ ID NO 15
<211> LENGTH: 24
<212> TYPE: DNA
<213> ORGANISM: Artificial Sequence
<220> FEATURE:
<223> OTHER INFORMATION: Reverse primer of mIl6

<400> SEQUENCE: 15
caagtgcatc atcgttgtta ctac                                  24

<210> SEQ ID NO 16
<211> LENGTH: 25
<212> TYPE: DNA
<213> ORGANISM: Artificial Sequence
<220> FEATURE:
<223> OTHER INFORMATION: Forward primer of mTnfa

<400> SEQUENCE: 16
catcttctca aaattcgagt gacaa                                 25

<210> SEQ ID NO 17
<211> LENGTH: 23
<212> TYPE: DNA
<213> ORGANISM: Artificial Sequence
<220> FEATURE:
<223> OTHER INFORMATION: Reverse primer of mTnfa

<400> SEQUENCE: 17
cccaacatgg aacagatgag ggt                                   23

<210> SEQ ID NO 18
<211> LENGTH: 22
<212> TYPE: DNA

```
<213> ORGANISM: Artificial Sequence
<220> FEATURE:
<223> OTHER INFORMATION: Forward primer of mIlb

<400> SEQUENCE: 18
gaaatgccac cttttgacag tg                                              22

<210> SEQ ID NO 19
<211> LENGTH: 21
<212> TYPE: DNA
<213> ORGANISM: Artificial Sequence
<220> FEATURE:
<223> OTHER INFORMATION: Reverse primer of mIlb

<400> SEQUENCE: 19
tggatgctct catcaggaca g                                               21

<210> SEQ ID NO 20
<211> LENGTH: 21
<212> TYPE: DNA
<213> ORGANISM: Artificial Sequence
<220> FEATURE:
<223> OTHER INFORMATION: Forward primer of mIfng

<400> SEQUENCE: 20
atgaacgcta cacactgcat c                                               21

<210> SEQ ID NO 21
<211> LENGTH: 21
<212> TYPE: DNA
<213> ORGANISM: Artificial Sequence
<220> FEATURE:
<223> OTHER INFORMATION: Reverse primer of mIfng

<400> SEQUENCE: 21
ccatcctttt gccagttcct c                                               21

<210> SEQ ID NO 22
<211> LENGTH: 21
<212> TYPE: DNA
<213> ORGANISM: Artificial Sequence
<220> FEATURE:
<223> OTHER INFORMATION: Forward primer of mI717a

<400> SEQUENCE: 22
tttaactccc ttggcgcaaa a                                               21

<210> SEQ ID NO 23
<211> LENGTH: 20
<212> TYPE: DNA
<213> ORGANISM: Artificial Sequence
<220> FEATURE:
<223> OTHER INFORMATION: Reverse primer of mI717a

<400> SEQUENCE: 23
ctttccctcc gcattgacac                                                 20

<210> SEQ ID NO 24
<211> LENGTH: 21
<212> TYPE: DNA
<213> ORGANISM: Artificial Sequence
<220> FEATURE:
<223> OTHER INFORMATION: Forward primer of mGmcsf

<400> SEQUENCE: 24
ggccttggaa gcatgtagag g                                               21
```

```
<210> SEQ ID NO 25
<211> LENGTH: 21
<212> TYPE: DNA
<213> ORGANISM: Artificial Sequence
<220> FEATURE:
<223> OTHER INFORMATION: Reverse primer of mGmcsf

<400> SEQUENCE: 25
ccatcctttt gccagttcct c                                              21

<210> SEQ ID NO 26
<211> LENGTH: 20
<212> TYPE: DNA
<213> ORGANISM: Artificial Sequence
<220> FEATURE:
<223> OTHER INFORMATION: Forward primer of mActb

<400> SEQUENCE: 26
tgtccctgta tgcctctggt                                                20

<210> SEQ ID NO 27
<211> LENGTH: 19
<212> TYPE: DNA
<213> ORGANISM: Artificial Sequence
<220> FEATURE:
<223> OTHER INFORMATION: Reverse primer of mActb

<400> SEQUENCE: 27
cacgcacgat ttccctctc                                                 19
```